US011026792B2

(12) United States Patent
Kislev et al.

(10) Patent No.: US 11,026,792 B2
(45) Date of Patent: Jun. 8, 2021

(54) LEAFLET-GROUPING SYSTEM

(71) Applicant: CARDIOVALVE LTD., Or Yehuda (IL)

(72) Inventors: Yonatan Kislev, Rosh Haayin (IL); Or Cohen, Tel Aviv (IL); Meni Iamberger, Kfar Saba (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/937,216

(22) Filed: Jul. 23, 2020

(65) Prior Publication Data
US 2020/0405486 A1   Dec. 31, 2020

Related U.S. Application Data

(63) Continuation-in-part of application No. PCT/IL2020/050315, filed on Mar. 17, 2020, and a continuation-in-part of application No. PCT/IL2019/051031, filed on Sep. 16, 2019, which is a continuation of application No. 16/132,937, filed on Sep. 17, 2018, now Pat. No. 10,779,946.

(51) Int. Cl.
*A61F 2/24* (2006.01)
(52) U.S. Cl.
CPC .......... *A61F 2/2472* (2013.01); *A61F 2/2415* (2013.01)
(58) Field of Classification Search
CPC ................................ A61F 2/2472; G01L 1/24
See application file for complete search history.

(56) References Cited

U.S. PATENT DOCUMENTS

| 4,972,494 A | * | 11/1990 | White .................... B65B 19/28 209/535 |
|---|---|---|---|
| 5,713,948 A | | 2/1998 | Uflacker |
| 5,776,140 A | | 7/1998 | Cottone |
| 5,957,949 A | | 9/1999 | Leonhardt et al. |
| 6,010,530 A | | 1/2000 | Goicoechea |

(Continued)

FOREIGN PATENT DOCUMENTS

| CN | 103974674 | 8/2014 |
| EA | 2019/077595 | 4/2019 |

(Continued)

OTHER PUBLICATIONS

Notice of Allowance dated Dec. 22, 2017, which issued during the prosecution of U.S. Appl. No. 15/788,407.

(Continued)

*Primary Examiner* — Joshua L Schwartz
(74) *Attorney, Agent, or Firm* — Dilworth IP, LLC

(57) ABSTRACT

A method for grouping prosthetic valve leaflets of an aggregate of prosthetic valve leaflets is provided. Using a computer processor, for each leaflet of the aggregate, in response to an image parameter of the leaflet, a leaflet-flexibility value is derived. A group size value is provided to the processor. Using the processor, at least some of the leaflets of the aggregate are designated into leaflet groups, based on similarity between the respective leaflet-flexibility value of each leaflet of the aggregate. Each of the leaflet groups includes a number of leaflets equal to the group size value. Using the processor, an indication of the designated leaflet groups is outputted. Other embodiments are also described.

21 Claims, 36 Drawing Sheets

(56) References Cited

U.S. PATENT DOCUMENTS

| | | |
|---|---|---|
| 6,245,105 B1 | 6/2001 | Nguyen et al. |
| 6,402,780 B2 | 6/2002 | Williamson, IV et al. |
| 6,413,275 B1 | 7/2002 | Nguyen et al. |
| 6,454,799 B1 | 9/2002 | Schreck |
| 6,837,902 B2 | 1/2005 | Nguyen et al. |
| 7,018,406 B2 | 3/2006 | Seguin et al. |
| 7,585,321 B2 | 9/2009 | Cribier |
| 8,361,144 B2 | 1/2013 | Fish et al. |
| 8,568,475 B2 | 10/2013 | Nguyen et al. |
| 8,628,571 B1 | 1/2014 | Hacohen et al. |
| 8,728,155 B2 | 5/2014 | Montorfano et al. |
| 8,850,898 B2 | 10/2014 | Johnsen |
| 8,852,272 B2 | 10/2014 | Gross et al. |
| 8,870,948 B1 | 10/2014 | Erzberger et al. |
| 8,870,950 B2 | 10/2014 | Hacohen |
| 8,998,982 B2 | 4/2015 | Richter et al. |
| 9,017,399 B2 | 4/2015 | Gross et al. |
| 9,023,100 B2 | 5/2015 | Quadri et al. |
| 9,095,434 B2 | 8/2015 | Rowe |
| 9,097,620 B2 | 8/2015 | Caron et al. |
| 9,180,009 B2 | 11/2015 | Majkrzak et al. |
| 9,232,995 B2 | 1/2016 | Kovalsky et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,387,078 B2 | 7/2016 | Gross et al. |
| 9,439,757 B2 | 9/2016 | Wallace et al. |
| 9,492,273 B2 | 11/2016 | Wallace et al. |
| 9,554,899 B2 | 1/2017 | Granada et al. |
| 9,561,103 B2 | 2/2017 | Granada et al. |
| 9,662,203 B2 | 5/2017 | Sheahan et al. |
| 9,681,952 B2 | 6/2017 | Hacohen et al. |
| 9,763,657 B2 | 9/2017 | Hacohen et al. |
| D800,908 S | 10/2017 | Hariton et al. |
| 9,788,941 B2 | 10/2017 | Hacohen |
| 9,895,226 B1 | 2/2018 | Harari et al. |
| 9,987,132 B1 | 6/2018 | Hariton et al. |
| 10,010,414 B2 | 7/2018 | Cooper et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz et al. |
| 10,226,341 B2 | 3/2019 | Gross et al. |
| 10,245,143 B2 | 4/2019 | Gross et al. |
| 10,258,471 B2 | 4/2019 | Lutter et al. |
| 10,321,995 B1 | 6/2019 | Christianson et al. |
| 10,327,895 B2 | 6/2019 | Lozonschi et al. |
| 10,376,361 B2 | 8/2019 | Gross et al. |
| 10,531,866 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,779,946 B2 | 9/2020 | Kislev et al. |
| 2002/0032481 A1 | 3/2002 | Gabbay et al. |
| 2002/0151970 A1 | 10/2002 | Garrison et al. |
| 2004/0186558 A1 | 9/2004 | Pavcnik et al. |
| 2004/0249433 A1 | 12/2004 | Freitag |
| 2005/0137690 A1 | 6/2005 | Salahieh et al. |
| 2005/0240200 A1 | 10/2005 | Bergheim |
| 2005/0251251 A1 | 11/2005 | Cribier |
| 2006/0004469 A1 | 1/2006 | Sokel |
| 2006/0020327 A1 | 1/2006 | Lashinski et al. |
| 2006/0052867 A1 | 3/2006 | Revuelta et al. |
| 2006/0195183 A1 | 8/2006 | Navia et al. |
| 2006/0259137 A1 | 11/2006 | Artof et al. |
| 2006/0282150 A1 | 12/2006 | Olson et al. |
| 2007/0056346 A1 | 3/2007 | Spenser et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2008/0071361 A1 | 3/2008 | Tuval et al. |
| 2008/0147182 A1 | 6/2008 | Righini et al. |
| 2008/0200980 A1 | 8/2008 | Robin et al. |
| 2008/0234814 A1 | 9/2008 | Salahieh et al. |
| 2008/0281411 A1 | 11/2008 | Berreklouw |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2010/0023120 A1 | 1/2010 | Holecek et al. |
| 2010/0100167 A1 | 4/2010 | Bortlein et al. |
| 2010/0161036 A1 | 6/2010 | Pintor et al. |
| 2010/0331971 A1 | 12/2010 | Keränen et al. |
| 2011/0004299 A1 | 1/2011 | Navia et al. |
| 2011/0021985 A1 | 1/2011 | Spargias |
| 2011/0029072 A1 | 2/2011 | Gabbay |
| 2011/0112632 A1 | 5/2011 | Chau et al. |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0208298 A1 | 8/2011 | Tuval et al. |
| 2011/0218620 A1 | 9/2011 | Meiri et al. |
| 2011/0224785 A1 | 9/2011 | Hacohen |
| 2011/0282439 A1 | 11/2011 | Thill et al. |
| 2011/0307049 A1 | 12/2011 | Kao |
| 2011/0319989 A1 | 12/2011 | Lane et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0022640 A1 | 1/2012 | Gross et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0089223 A1 | 4/2012 | Nguyen et al. |
| 2012/0300063 A1* | 11/2012 | Majkrzak ............. A61F 2/2472 348/135 |
| 2012/0310328 A1 | 12/2012 | Olson et al. |
| 2013/0018458 A1 | 1/2013 | Yohanan et al. |
| 2013/0035759 A1 | 2/2013 | Gross et al. |
| 2013/0150956 A1 | 6/2013 | Yohanan et al. |
| 2013/0261738 A1 | 10/2013 | Clague et al. |
| 2013/0304200 A1 | 11/2013 | Mclean et al. |
| 2014/0000112 A1 | 1/2014 | Braido et al. |
| 2014/0005778 A1 | 1/2014 | Buchbinder et al. |
| 2014/0018915 A1 | 1/2014 | Biadillah et al. |
| 2014/0142688 A1 | 5/2014 | Duffy et al. |
| 2014/0172077 A1 | 6/2014 | Bruchman et al. |
| 2014/0207231 A1 | 7/2014 | Hacohen et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0257467 A1 | 9/2014 | Lane et al. |
| 2014/0277409 A1 | 9/2014 | Börtlein et al. |
| 2014/0277411 A1 | 9/2014 | Börtlein et al. |
| 2014/0277418 A1 | 9/2014 | Miller |
| 2014/0358224 A1 | 12/2014 | Tegels et al. |
| 2015/0142100 A1 | 5/2015 | Morriss et al. |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0272734 A1 | 10/2015 | Sheps et al. |
| 2015/0320556 A1 | 11/2015 | Levi et al. |
| 2015/0327994 A1 | 11/2015 | Morriss et al. |
| 2015/0351903 A1 | 12/2015 | Morriss et al. |
| 2015/0351904 A1 | 12/2015 | Cooper et al. |
| 2016/0030169 A1 | 2/2016 | Shahriari |
| 2016/0317305 A1 | 11/2016 | Pelled et al. |
| 2016/0324635 A1 | 11/2016 | Vidlund et al. |
| 2016/0374801 A1 | 12/2016 | Jimenez et al. |
| 2016/0374802 A1 | 12/2016 | Levi et al. |
| 2017/0056166 A1 | 3/2017 | Ratz et al. |
| 2017/0135816 A1 | 5/2017 | Lashinski et al. |
| 2017/0189174 A1 | 7/2017 | Braido et al. |
| 2017/0333187 A1 | 11/2017 | Hariton et al. |
| 2018/0000580 A1 | 1/2018 | Wallace et al. |
| 2018/0021129 A1 | 1/2018 | Peterson et al. |
| 2018/0125644 A1 | 5/2018 | Conklin |
| 2018/0153687 A1 | 6/2018 | Hariton et al. |
| 2018/0206983 A1 | 7/2018 | Noe et al. |
| 2018/0250126 A1 | 9/2018 | O'connor et al. |
| 2018/0296336 A1 | 10/2018 | Cooper et al. |
| 2018/0344457 A1 | 12/2018 | Gross et al. |
| 2018/0353294 A1 | 12/2018 | Calomeni et al. |
| 2019/0053896 A1 | 2/2019 | Adamek-bowers et al. |

(56) References Cited

U.S. PATENT DOCUMENTS

| | | |
|---|---|---|
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Raz et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0183639 A1 | 6/2019 | Moore |
| 2019/0216602 A1 | 7/2019 | Lozonschi |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000579 A1 | 1/2020 | Manash et al. |
| 2020/0015964 A1 | 1/2020 | Noe et al. |
| 2020/0060818 A1 | 2/2020 | Geist et al. |
| 2020/0085578 A1 | 3/2020 | Kislev et al. |
| 2020/0281723 A1 | 9/2020 | Harari et al. |

FOREIGN PATENT DOCUMENTS

| | | |
|---|---|---|
| EP | 0170262 | 2/1986 |
| EP | 1264582 | 12/2002 |
| GB | 844190 | 8/1960 |
| JP | S53152790 | 12/1978 |
| KR | 20010046894 | 6/2001 |
| WO | 1998/043557 | 10/1998 |
| WO | 01/82832 | 11/2001 |
| WO | 2010/006627 | 1/2010 |
| WO | 2010/057262 | 5/2010 |
| WO | 2012/048035 | 4/2012 |
| WO | 2013/021374 | 2/2013 |
| WO | 2013/021375 | 2/2013 |
| WO | 2013/059747 | 4/2013 |
| WO | 2013/072496 | 5/2013 |
| WO | 2013/078497 | 6/2013 |
| WO | 2013/175468 | 11/2013 |
| WO | 2014/076696 | 5/2014 |
| WO | 2014/115149 | 7/2014 |
| WO | 2014/164364 | 10/2014 |
| WO | 2016/016899 | 2/2016 |
| WO | 2016/125160 | 8/2016 |
| WO | 2018/025263 | 2/2018 |
| WO | 2018/029680 | 2/2018 |
| WO | 2018/039631 | 3/2018 |
| WO | 2019/026059 | 2/2019 |
| WO | 2019/030753 | 2/2019 |
| WO | 2019116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/165889 | 8/2020 |

OTHER PUBLICATIONS

An International Search Report and a Written Opinion both dated Jun. 20, 2018, which issued during the prosecution of Applicant's PCT/IL2018/050024.

An International Preliminary Report on Patentability dated Apr. 21, 2020, which issued during the prosecution of Applicant's PCT/IL2018/050024.

An International Search Report and a Written Opinion both dated Nov. 9, 2018, which issued during the prosecution of Applicant's PCT/IL2018/050869.

An International Search Report and a Written Opinion both dated May 13, 2019, which issued during the prosecution of Applicant's PCT/IL2018/051350.

An International Search Report and a Written Opinion both dated Apr. 25, 2019, which issued during the prosecution of Applicant's PCT/IL2019/050142.

An International Search Report and a Written Opinion both dated Jan. 25, 2019, which issued during the prosecution of Applicant's PCT/IL2018/051122.

An International Search Report and a Written Opinion both dated Dec. 5, 2018, which issued during the prosecution of Applicant's PCT/IL2018/050725.

An International Preliminary Report on Patentability dated Feb. 12, 2019, which issued during the prosecution of Applicant's PCT/IL2017/050873.

An International Preliminary Report on Patentability dated Feb. 5, 2019, which issued during the prosecution of Applicant's PCT/IL2017/050849.

An Office Action dated Mar. 25, 2019, which issued during the prosecution of European Patent Application No. 14710060.6.

An Office Action dated Oct. 25, 2018, which issued during the prosecution of U.S. Appl. No. 14/763,004.

An Office Action dated Mar. 4, 2019, which issued during the prosecution of U.S. Appl. No. 14/763,004.

An Office Action dated Jan. 9, 2019, which issued during the prosecution of U.S. Appl. No. 15/329,920.

An Office Action dated Jan. 30, 2019, which issued during the prosecution of U.S. Appl. No. 15/872,501.

An Office Action dated May 14, 2020, which issued during the prosecution of U.S. Appl. No. 16/132,937.

An Office Action dated Feb. 5, 2019. which issued during the prosecution of U.S. Appl. No. 15/899,858.

An Office Action dated May 23, 2019, which issued during the prosecution of U.S. Appl. No. 15/668,659.

An Office Action dated May 1, 2019, which issued during the prosecution of U.S. Appl. No. 15/691,032.

An Office Action dated May 16, 2019. which issued during the prosecution of U.S. Appl. No. 15/433,547.

An Office Action dated Aug. 1, 2019, which issued during the prosecution of U.S. Appl. No. 15/668,559.

An Office Action dated Jun. 25, 2019, which issued during the prosecution of U.S. Appl. No. 15/329,920.

An Office Action dated Nov. 1, 2010 which issued during the prosecution of U.S. Appl. No. 15/872,501.

An Office Action dated Aug. 16, 2019, which issued during the prosecution of U.S. Appl. No. 15/668,659.

An Office Action dated Jun. 19, 2019. which issued during the prosecution of U.S. Appl. No. 15/682,789.

An Office Action dated Jun. 14, 2019, which issied during the prosecution of U.S. Appl. No. 15/703,385.

An Office Action dated Oct. 4, 2019 which issued during the prosecution of U.S. Appl. No. 16/183,140.

An Office Action dated Sep. 13, 2019, which issued during the prosecution of U.S. Appl. No. 16/460,313.

An Office Action dated Nov. 26, 2019, which issued during the prosecution of U.S. Appl. No. 16/532,945.

An Office Action dated Jun. 13, 2019, which issued during the prosecution of U.S. Appl. No. 16/388,038.

An Office Action dated Jan. 6, 2020, which issued during the prosecution U.S. Appl. No. 16/660,231.

Notice of Allowance dated Oct. 19, 2020, which issued during the prosecution of U.S. Appl. No. 16/937,216.

An Office Action dated Aug. 13, :2019 which issued during the prosecution of UK Patent Application No. 1901887.8.

An Office Action dated Dec. 31, 2019, which issued during the prosecution of U.S. Appl. No. 16/183,140.

An Office Action dated Jan.14, 2020, which issued during the prosecution of U.S. Appl. No. 16/284,331.

Notice of Allowance dated Jan. 13, 2020, which issued during the prosecution of U.S. Appl. No. 15/956,956.

European Search Report dated dated Mar. 5, 2020 which issued during the prosecution of Applicant's European App No. 17752184.6.

European Search Report dated Mar. 4, 2020 which issued during the prosecution of Applicant's Europeam App No. 16706913.7.

Notice of Allowance dated Mar. 12, 2020, which issued during the prosecution of U.S. Appl. No. 16/460,313.

An Office Action dated Jan. 9. 2020, which issued during the prosecution of U.S. Appl. No. 15/600,190.

(56) References Cited

OTHER PUBLICATIONS

An Office Action dated Jan. 3 2020, which issued during the prosecution of U.S. Appl. No. 16/678,355.
An Office Action dated Feb. 6, 2020, which issued during the prosecution of U.S. Appl. No. 15/668,659.
An Office Action dated Sep. 24, 2020, which issued during the prosecution of U.S. Appl. No. 16/811,732.
Symetis S.A.: "ACURATE neo™ Aortic Bioprosthesis for Implantation using the ACURATE neo™ TA Transapical Delivery System in Patients with Severe Aortic Stenosis," Clinical Investigation Plan, Protocol Number: Jan. 2015, Vs. No. 2, 2015:1-76:.
An Office Action dated Nov. 30, 2020, which issued during the prosecution of U.S. Appl. No. 16/138,129.
Notice of Allowance dated Nov. 19, 2020, which issued during the prosecution of U.S. Appl. No. 16/318,025.
An Office Action dated Oct. 5. 2020, which issued during the prosecution of Canadian Patent Application No. 2,973,940.
An International Preliminary Report on Patentability dated Oct. 20, 2020, which issued during the prosecution of Applicant's PCT/IL2019/050142.
An Office Action summarized English translation and Search Report dated Nov. 25, 2020, which issued during the prosecution of Chinese Patent Application No. 201910449820.1.
An International Search Report and a Written Opinion both dated Jan. 28, 2020, which issued during the prosecution of Applicant's PCT/IL2019/051031.
Sündermann, Simon H., et al. "Feasibility of the Engager™ aortic transcatheter valve system using a flexible over-the-wire design." European Journal of Cardio-Thoracic Surgery 42.4 (2012): e48-e52.

Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dq=%20%22Edwards%20SAPIEN%22&lr&pg=PA20#v=onepage&q=%22Edwards%20SAPIEN%22&f=false; Downloaded on Jun. 18, 2020.
Notice of Allowance dated May 7, 2020, which issued during the prosecution of U.S. Appl. No. 16/637,166.
An Office Action dated Aug. 7, 2020, which issued during the prosecution of U.S. Appl. No. 15/688,659.
Notice of Allowance dated Jul. 29, 2020, which issued during the prosecution of U.S. Appl. No. 16/132,937.
Notice of Allowance dated Sep. 10, 2020, which issued during the prosecution of U.S. Appl. No. 15/610,190.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
An Office Action summarized English translation and Search Report dated Jul. 3, 2020, which issued during the prosecution of Chinese Patent Application No. 201780061210.3.
Tchetche, D. and Nicolas M. Van Mieghe: "New-generation TAVI devices: description and specifications" EuroIntervention, 2014, No. 10:U90-U100.
An International Search Report and a Written Opinion both dated Jun. 24, 2020, which issued during the prosecution of Applicant's PCT/IL2019/051398.

* cited by examiner

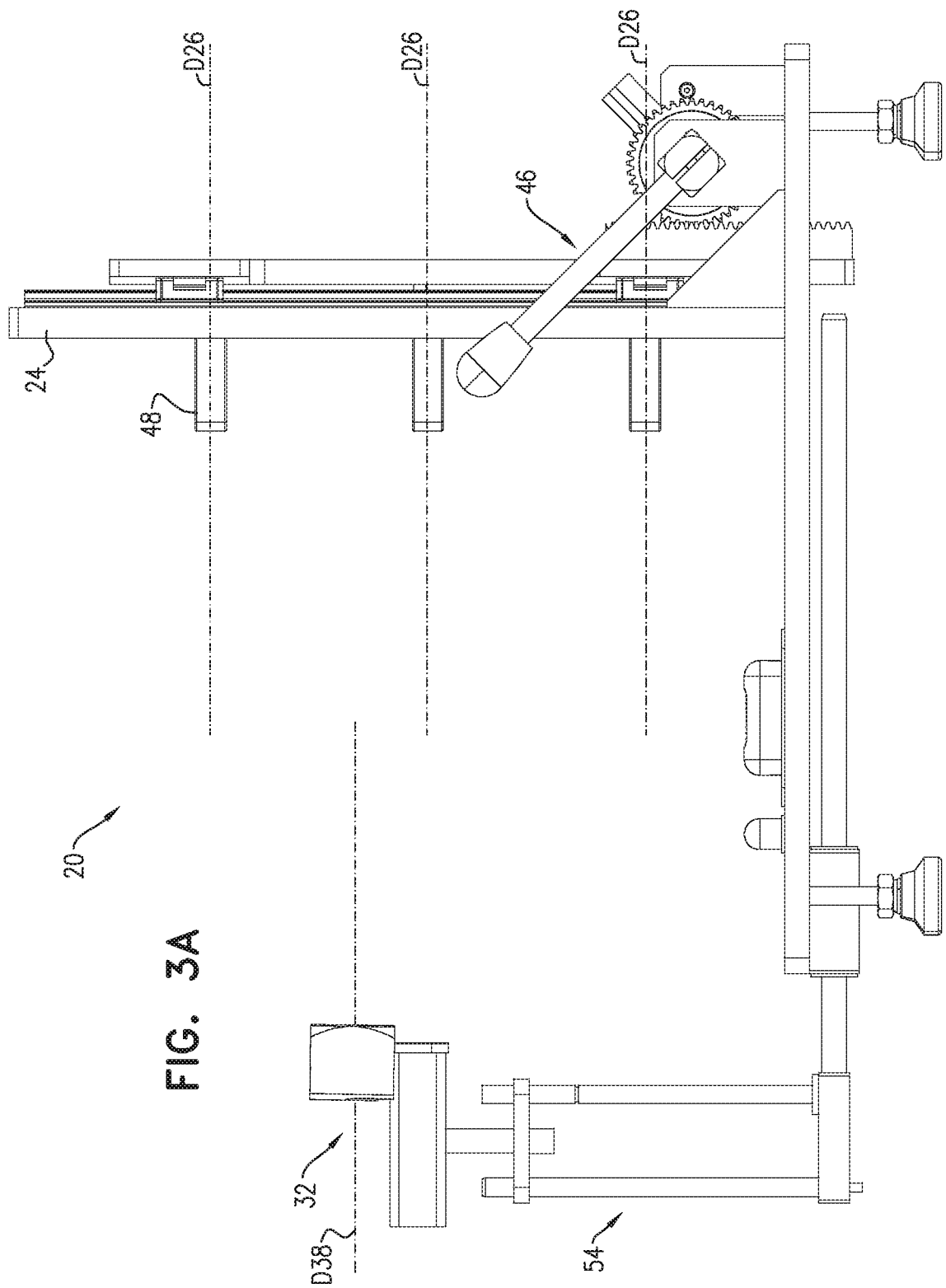

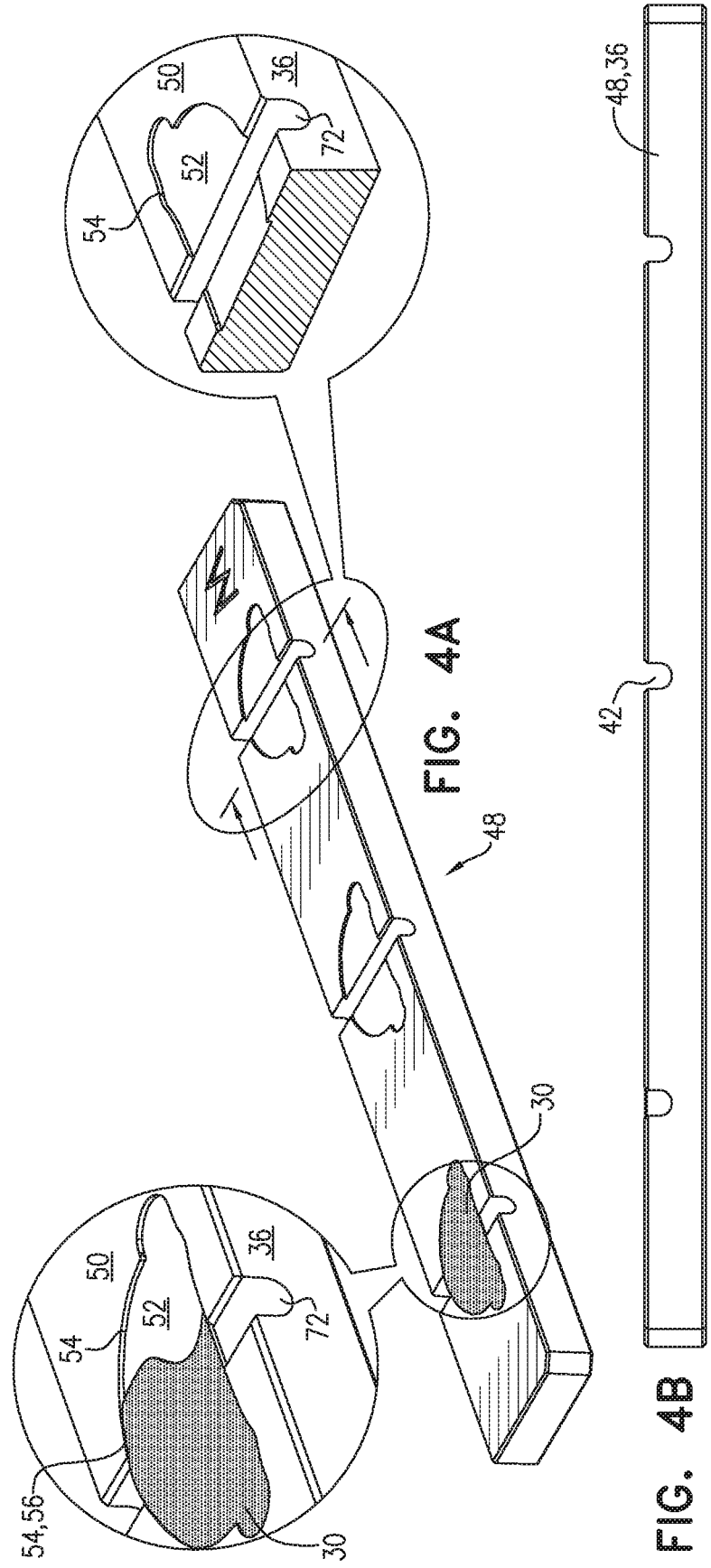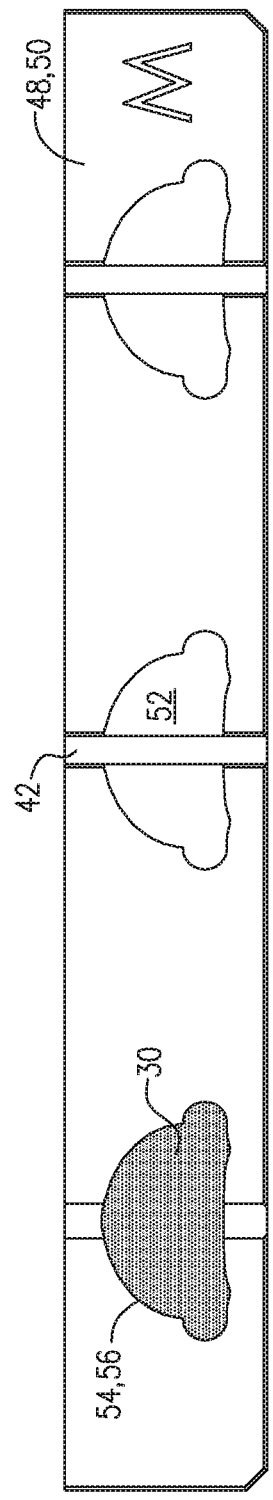
FIG. 4A
FIG. 4B
FIG. 4C

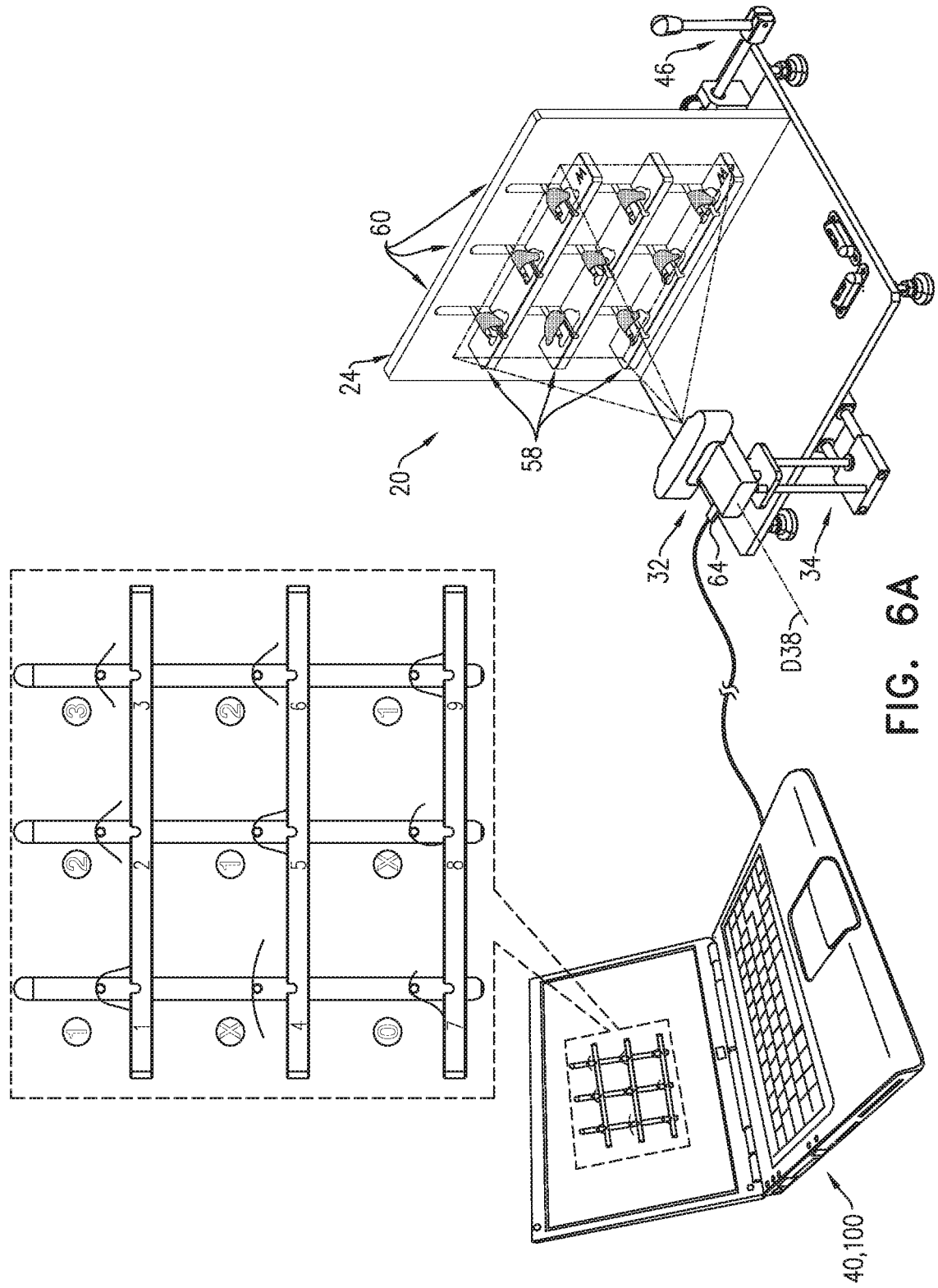

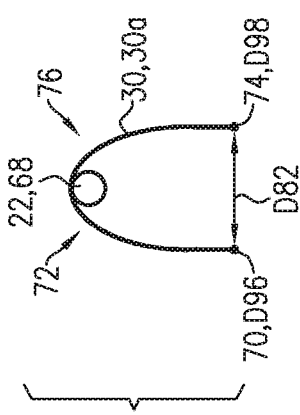
FIG. 7A
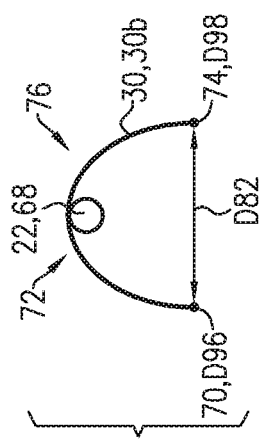
FIG. 7B
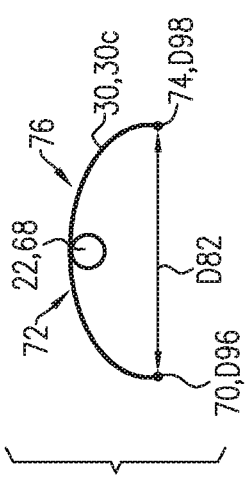
FIG. 7C
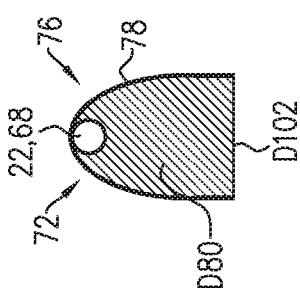
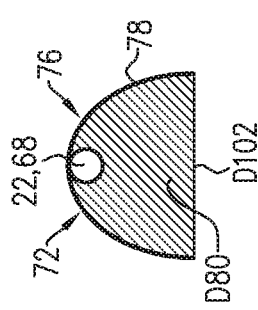
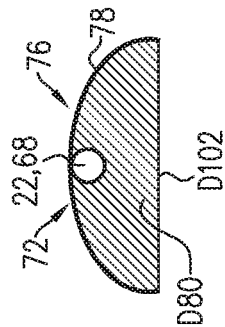
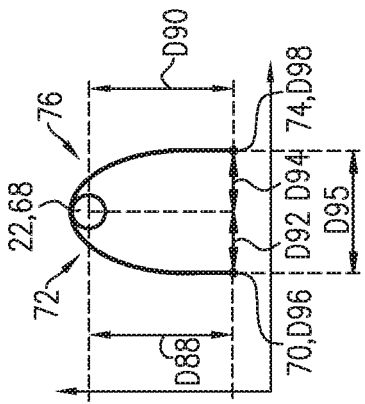
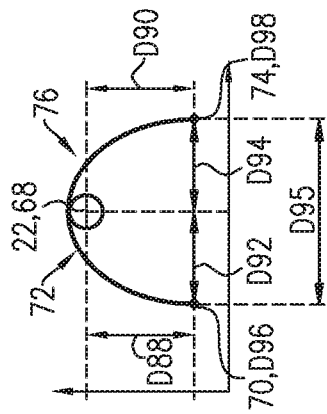
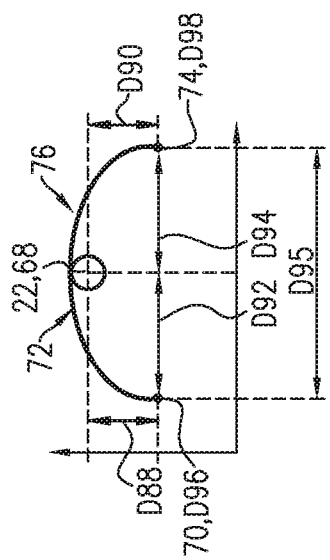

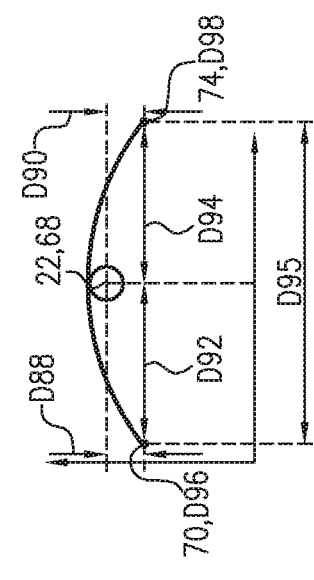
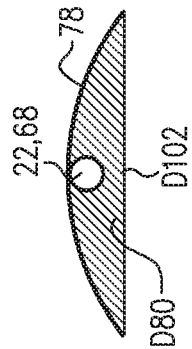
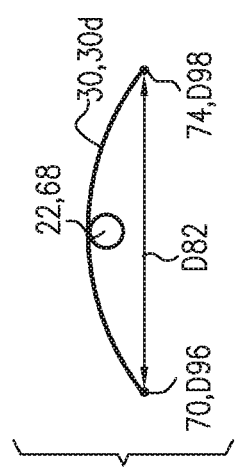
FIG. 8A
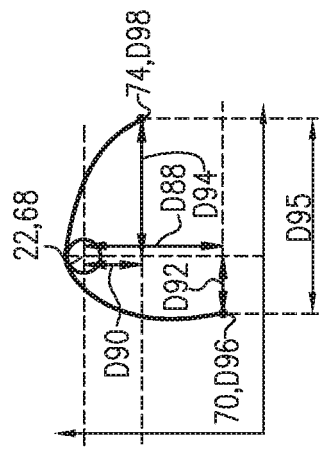
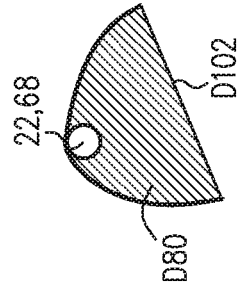
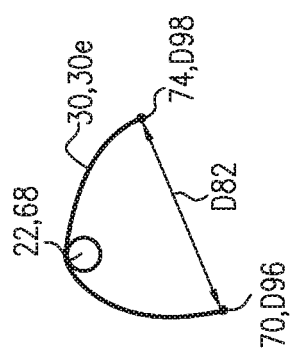
FIG. 8B

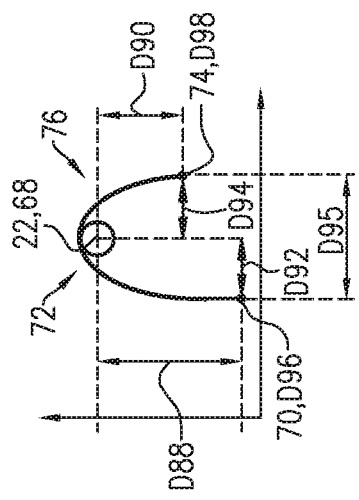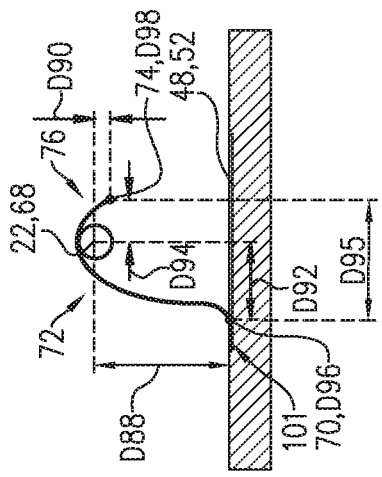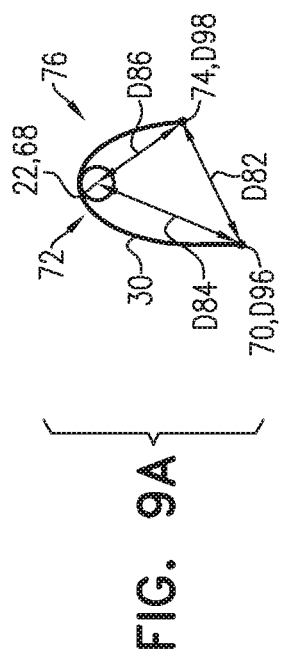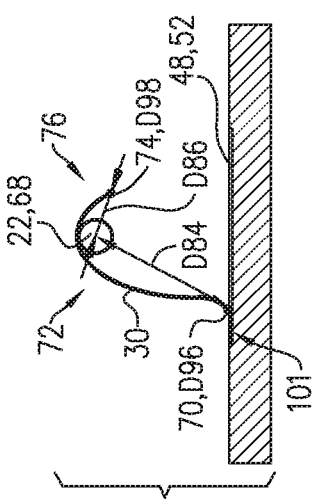
FIG. 9A
FIG. 9B

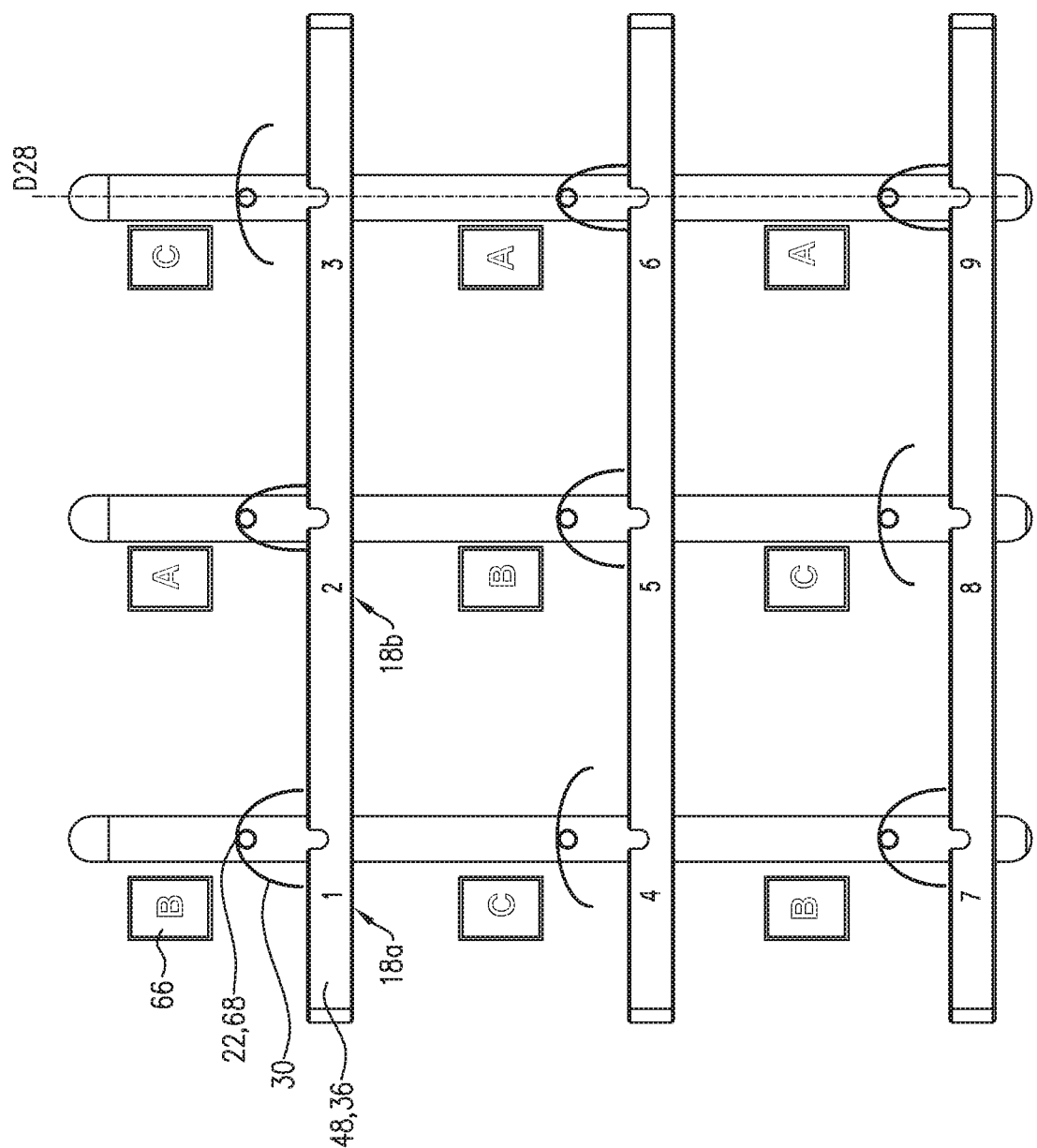

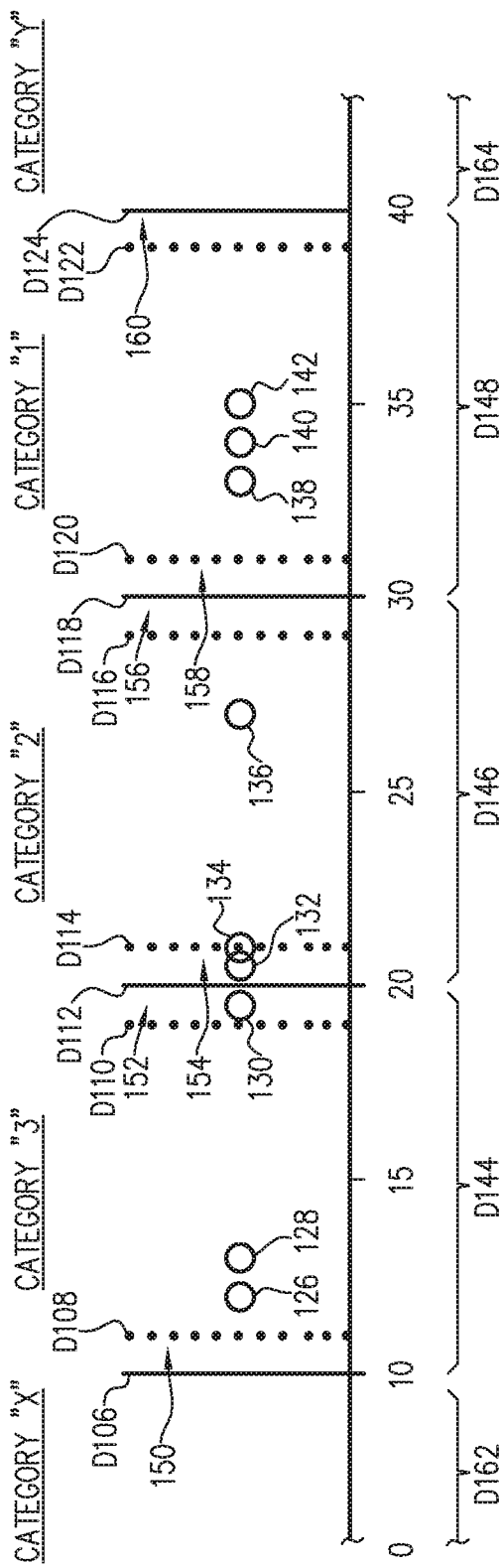
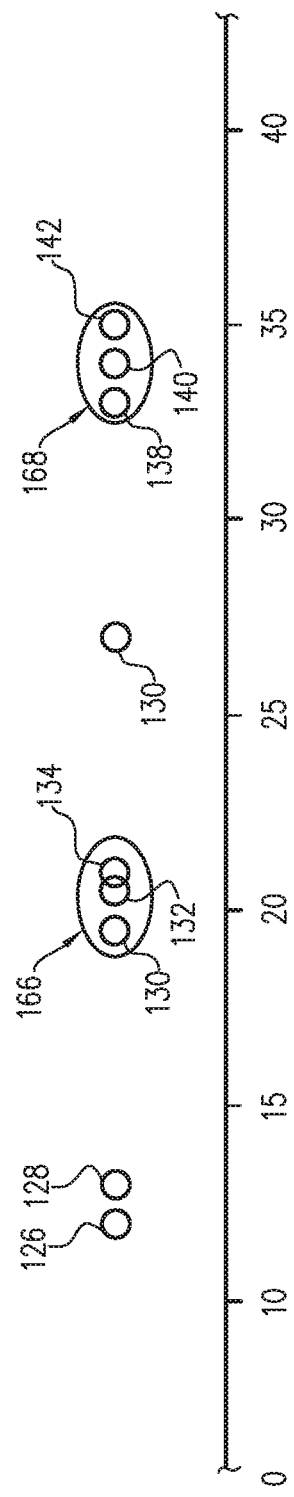
FIG. 12A
FIG. 12B

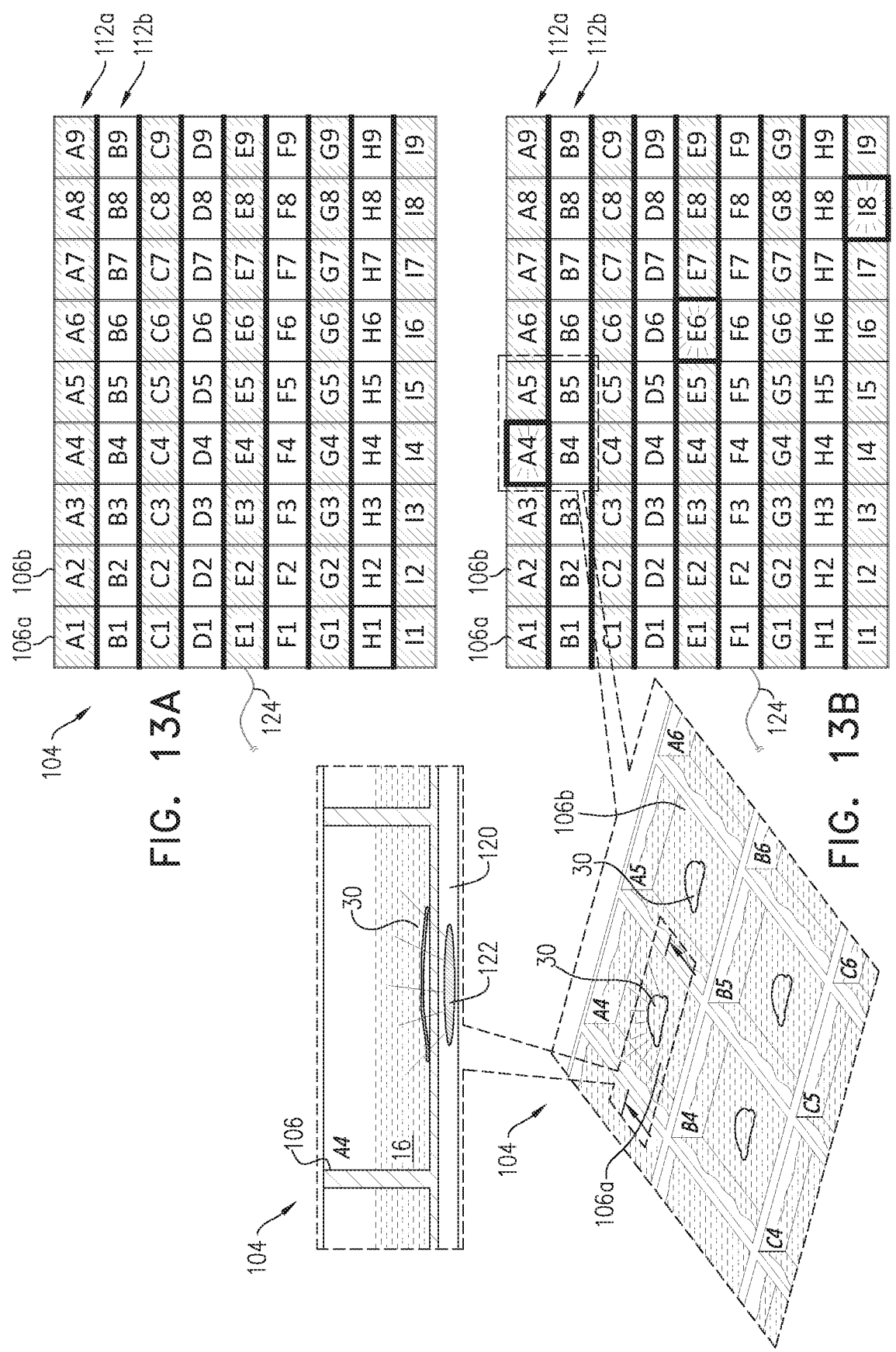

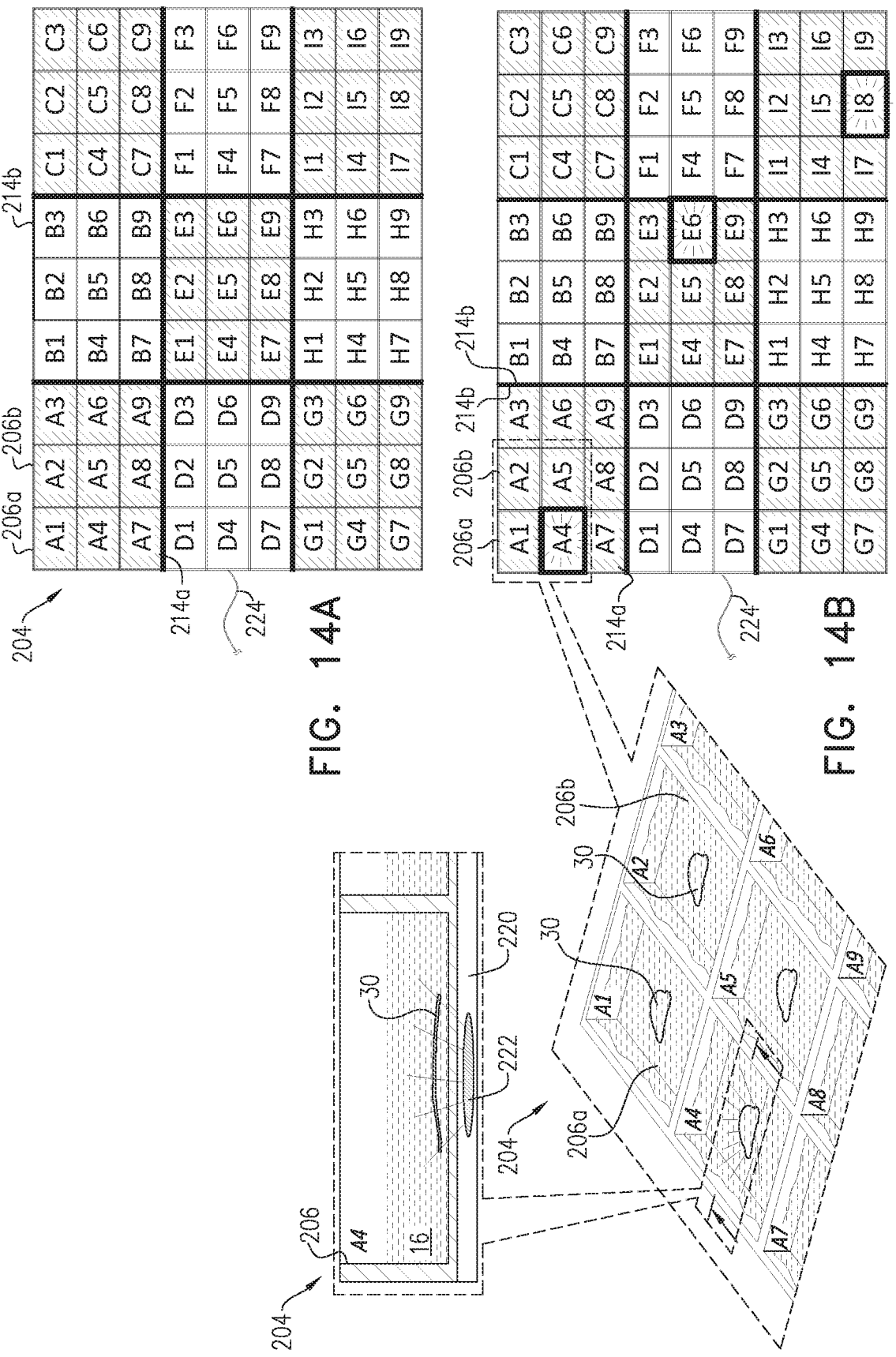

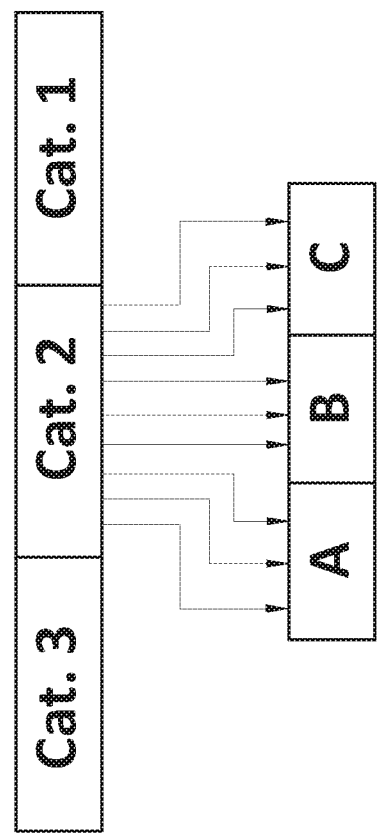

FIG. 19

$\Delta t_1 = (i_3 - i_1) = 25 - 21 = 4$ $i_1\ i_2\ i_3\ i_4\ i_5\ i_6\ i_7\ i_8\ i_9\ i_{10}\ i_{11}\ i_{12}\ i_{13}\ i_{14}\ i_{15}\ i_{16}\ i_{17}\ i_{18}\ i_{19}\ i_{20}\ i_{21}\ i_{22}\ i_{23}$
21 22 [25 26] 27 28 28 29 30 31 32 32 32 35 38 38 39 40 41 44 45 46 49

T1

FIG. 20A $\Delta t_2 = (i_4 - i_2) = 26 - 22 = 4$ $i_1\ i_2\ i_3\ i_4\ i_5\ i_6\ i_7\ i_8\ i_9\ i_{10}\ i_{11}\ i_{12}\ i_{13}\ i_{14}\ i_{15}\ i_{16}\ i_{17}\ i_{18}\ i_{19}\ i_{20}\ i_{21}\ i_{22}\ i_{23}$
21 [22 25 26] 27 28 28 29 30 31 32 32 32 35 38 38 39 40 41 44 45 46 49

T2

FIG. 20B $\Delta t_3 = (i_5 - i_3) = 27 - 25 = 2$ $i_1\ i_2\ i_3\ i_4\ i_5\ i_6\ i_7\ i_8\ i_9\ i_{10}\ i_{11}\ i_{12}\ i_{13}\ i_{14}\ i_{15}\ i_{16}\ i_{17}\ i_{18}\ i_{19}\ i_{20}\ i_{21}\ i_{22}\ i_{23}$
21 22 [25 26 27] 28 28 29 30 31 32 32 32 35 38 38 39 40 41 44 45 46 49

FIG. 20D $$\Delta t_1 = (i_3 - i_1) = 25 - 21 = 4 \quad \begin{Bmatrix} i_1 & i_2 & i_3 & i_4 & i_5 & i_6 & i_7 & i_8 & i_9 & i_{10} & i_{11} & i_{12} & i_{13} & i_{14} & i_{15} & i_{16} & i_{17} & i_{18} & i_{19} & i_{20} & i_{21} & i_{22} & i_{23} \\ 21 & 22 & \boxed{25} & 26 & 27 & 28 & 28 & 29 & 30 & 31 & 32 & 32 & 32 & 35 & 38 & 38 & 39 & 40 & 41 & 44 & 45 & 46 & 49 \end{Bmatrix}$$

FIG. 21A $$\Delta t_2 = (i_4 - i_2) = 26 - 22 = 4 \quad \begin{Bmatrix} i_1 & i_2 & i_3 & i_4 & i_5 & i_6 & i_7 & i_8 & i_9 & i_{10} & i_{11} & i_{12} & i_{13} & i_{14} & i_{15} & i_{16} & i_{17} & i_{18} & i_{19} & i_{20} & i_{21} & i_{22} & i_{23} \\ 21 & \boxed{22 \; 25 \; 26} & 27 & 28 & 28 & 29 & 30 & 31 & 32 & 32 & 32 & 35 & 38 & 38 & 39 & 40 & 41 & 44 & 45 & 46 & 49 \end{Bmatrix}$$

FIG. 21B $$\Delta t_3 = (i_5 - i_3) = 27 - 25 = 2 \quad \begin{Bmatrix} i_1 & i_2 & i_3 & i_4 & i_5 & i_6 & i_7 & i_8 & i_9 & i_{10} & i_{11} & i_{12} & i_{13} & i_{14} & i_{15} & i_{16} & i_{17} & i_{18} & i_{19} & i_{20} & i_{21} & i_{22} & i_{23} \\ 21 & 22 & \boxed{25 \; 26 \; 27} & 28 & 28 & 29 & 30 & 31 & 32 & 32 & 32 & 35 & 38 & 38 & 39 & 40 & 41 & 44 & 45 & 46 & 49 \end{Bmatrix}$$

FIG. 21C

|  | $i_1$ | $i_2$ | $i_3$ | $i_4$ | $i_5$ | $i_6$ | $i_7$ | $i_8$ | $i_9$ | $i_{10}$ | $i_{11}$ | $i_{12}$ | $i_{13}$ | $i_{14}$ | $i_{15}$ | $i_{16}$ | $i_{17}$ | $i_{18}$ | $i_{19}$ | $i_{20}$ | $i_{21}$ | $i_{22}$ | $i_{23}$ |
|---|---|---|---|---|---|---|---|---|---|---|---|---|---|---|---|---|---|---|---|---|---|---|---|
| | 21 | 22 | 25 | 26 | 27 | 28 | 28 | 29 | 30 | 31 | 32 | 32 | 35 | 38 | 39 | 40 | 41 | 44 | 45 | 46 | 49 |
| $\Delta t_8 = (i_{10} - i_8) = 31-29=2$ | 21 | 22 | 25 | 26 | 27 | 28 | 28 | 29 | 30 | 31 | 32 | 32 | 35 | 38 | 39 | 40 | 41 | 44 | 45 | 46 | 49 |
| $\Delta t_{11} = (i_{13} - i_{11}) = 32-32=0$ | 21 | 22 | 25 | 26 | 27 | 28 | 28 | 29 | 30 | 31 | 32 | 32 | 35 | 38 | 39 | 40 | 41 | 44 | 45 | 46 | 49 |
| $\Delta t_{14} = (i_{16} - i_{14}) = 38-35=3$ | 21 | 22 | 25 | 26 | 27 | 28 | 28 | 29 | 30 | 31 | 32 | 32 | 35 | 38 | 39 | 40 | 41 | 44 | 45 | 46 | 49 |
| $\Delta t_{15} = (i_{17} - i_{15}) = 39-38=1$ | 21 | 22 | 25 | 26 | 27 | 28 | 28 | 29 | 30 | 31 | 32 | 32 | 35 | 38 | 39 | 40 | 41 | 44 | 45 | 46 | 49 |
| $\Delta t_{18} = (i_{20} - i_{18}) = 44-40=4$ | 21 | 22 | 25 | 26 | 27 | 28 | 28 | 29 | 30 | 31 | 32 | 32 | 35 | 38 | 39 | 40 | 41 | 44 | 45 | 46 | 49 |
| $\Delta t_{19} = (i_{21} - i_{19}) = 45-41=4$ | 21 | 22 | 25 | 26 | 27 | 28 | 28 | 29 | 30 | 31 | 32 | 32 | 35 | 38 | 39 | 40 | 41 | 44 | 45 | 46 | 49 |
| $\Delta t_{20} = (i_{22} - i_{20}) = 46-44=2$ | 21 | 22 | 25 | 26 | 27 | 28 | 28 | 29 | 30 | 31 | 32 | 32 | 35 | 38 | 39 | 40 | 41 | 44 | 45 | 46 | 49 |

FIG. 21E

| $i_1$ | $i_2$ | $i_3$ | $i_4$ | $i_5$ | $i_6$ | $i_7$ | $i_8$ | $i_9$ | $i_{10}$ | $i_{11}$ | $i_{12}$ | $i_{13}$ | $i_{14}$ | $i_{15}$ | $i_{16}$ | $i_{17}$ | $i_{18}$ | $i_{19}$ | $i_{20}$ | $i_{21}$ | $i_{22}$ | $i_{23}$ |
|---|---|---|---|---|---|---|---|---|---|---|---|---|---|---|---|---|---|---|---|---|---|---|
| 21 | 22 | 25 | 26 | ⎡27 28 28⎤ | | | 29 | 30 | 31 | 32 | 32 | 32 | 35 | 38 | 38 | 39 | 40 | 41 | 44 | 45 | 46 | 49 |

$$\underbrace{\phantom{i_8 \; i_9 \; i_{10} \; i_{11} \; i_{12}}}_{C8}$$

$$\Delta i_8^\dagger = (i_{10} - i_8) = 31 - 29 = 2$$

| 21 | 22 | 25 | 26 | 27 | 28 | 28 | ⎡29 30 31⎤ | | | 32 | 32 | 32 | 35 | 38 | 38 | 39 | 40 | 41 | 44 | 45 | 46 | 49 |

$$\Delta i_9^\dagger = (i_{11} - i_9) = 32 - 30 = 2$$

| 21 | 22 | 25 | 26 | 27 | 28 | 28 | 29 | ⎡30 31 32⎤ | | | 32 | 32 | 35 | 38 | 38 | 39 | 40 | 41 | 44 | 45 | 46 | 49 |

$$\Delta i_{10}^\dagger = (i_{12} - i_{10}) = 32 - 31 = 1$$

| 21 | 22 | 25 | 26 | 27 | 28 | 28 | 29 | 30 | ⎡31 32 32⎤ | | | 32 | 35 | 38 | 38 | 39 | 40 | 41 | 44 | 45 | 46 | 49 |

FIG. 21G

|  | $i_1$ | $i_2$ | $i_3$ | $i_4$ | $i_5$ | $i_6$ | $i_7$ | $i_8$ | $i_9$ | $i_{10}$ | $i_{11}$ | $i_{12}$ | $i_{13}$ | $i_{14}$ | $i_{15}$ | $i_{16}$ | $i_{17}$ | $i_{18}$ | $i_{19}$ | $i_{20}$ | $i_{21}$ | $i_{22}$ | $i_{23}$ |
|---|---|---|---|---|---|---|---|---|---|---|---|---|---|---|---|---|---|---|---|---|---|---|---|
| | 21 | 22 | 25 | 26 | [27 | 28 | 28] | 29 | 30 | 31 | 32 | 32 | 32 | 35 | 38 | 38 | 39 | 40 | 41 | 44 | 45 | 46 | 49 |
| | 21 | 22 | 25 | 26 | 27 | 28 | 28 | [29 | 30 | 31] | 32 | 32 | 32 | 35 | 38 | 38 | 39 | 40 | 41 | 44 | 45 | 46 | 49 |
| | 21 | 22 | 25 | 26 | 27 | 28 | 28 | 29 | 30 | 31 | 32 | 32 | [32 | 35 | 38] | 38 | 39 | 40 | 41 | 44 | 45 | 46 | 49 |
| | 21 | 22 | 25 | 26 | 27 | 28 | 28 | 29 | 30 | 31 | 32 | 32 | 32 | 35 | [38 | 38 | 39] | 40 | 41 | 44 | 45 | 46 | 49 |
| | 21 | 22 | 25 | 26 | 27 | 28 | 28 | 29 | 30 | 31 | 32 | 32 | 32 | 35 | 38 | 38 | 39 | 40 | 41 | [44 | 45 | 46] | 49 |

FIG. 22

LEAFLET-GROUPING SYSTEM

CROSS-REFERENCES TO RELATED APPLICATIONS

This application is a Continuation in Part of (i) PCT application IL2020/050315, to Kislev et al., filed on Mar. 17, 2020, and entitled "LEAFLET-GROUPING SYSTEM", and (ii) PCT application IL2019/051031, to Kislev et al., filed on Sep. 16, 2019, and entitled "LEAFLET-TESTING APPARATUS", which claims priority from, and is a Continuation of, U.S. patent application Ser. No. 16/132,937 filed Sep. 17, 2018, and entitled "LEAFLET-TESTING APPARATUS".

Each of the above applications is incorporated herein by reference.

FIELD OF THE INVENTION

Some applications of the present invention relate in general to prosthetic heart valves. More specifically, some applications of the present invention relate to techniques for appropriately grouping prosthetic leaflets for use in prosthetic heart valves.

BACKGROUND

Prosthetic heart valves may be constructed of a frame to which prosthetic leaflets are attached, the leaflets providing check-valve functionality by opening in response to blood flow in a first direction, and closing in response to blood flow in a second direction. In order to inhibit leakage ("regurgitation") of blood between the closed leaflets in the second direction, it is important that the leaflets coapt well against each other. One factor facilitating coaptation of leaflets in a prosthetic heart valve is flexibility of leaflets.

SUMMARY OF THE INVENTION

Some applications of the present invention are directed to appropriately grouping prosthetic leaflets, for use in prosthetic heart valves. Leaflet groups may be designated based on flexibility of the leaflets, e.g., such that leaflets are grouped with other leaflets that have similar flexibility. Leaflet groups typically include a fixed number of leaflets, e.g., according to the number of leaflets required for a given heart valve.

Aspects of the present invention include apparatus and methods for computationally assigning leaflet-flexibility values to leaflets, e.g., by digital analysis of one or more images of one or more pluralities of leaflets.

For some applications, an aggregate of leaflets including a first batch of leaflets and a second batch of leaflets is generated, and the groups are designated from leaflets of the aggregate based on similarity between the leaflet-flexibility values of the leaflets of the aggregate. For some such applications, the aggregate of leaflets is generated by testing each batch of leaflets, and storing each batch in a storage array in a manner that retains the individual identity of each leaflet. For some applications, the array is associated with a plurality of indicators that are activated in a manner that indicates the designated groups. For example, the array may define a plurality of cells, one cell for each leaflet of the aggregate, and one indicator for each cell.

There is therefore provided, in accordance with an application of the present invention, a method for grouping prosthetic valve leaflets of an aggregate of prosthetic valve leaflets, the method including, using a computer processor:

for each leaflet of the aggregate, in response to an image parameter of the leaflet, deriving a leaflet-flexibility value;
receiving a group size value;
designating at least some of the leaflets of the aggregate into designated leaflet groups, (i) based on similarity between the respective leaflet-flexibility value of each leaflet of the aggregate, and (ii) such that each of the designated leaflet groups includes a number of leaflets equal to the group size value; and
outputting an indication of the designated leaflet groups.

In an application, the method includes receiving an intra-group tolerance, the intra-group tolerance representing a maximum allowable difference between the leaflet-flexibility values of any two leaflets in a given leaflet group; and
designating at least some of the leaflets of the aggregate into designated leaflet groups includes designating at least some of the leaflets of the aggregate into designated leaflet groups, such that, for each of the designated leaflet groups, the flexibility value of each leaflet in the designated leaflet group is within the intra-group tolerance with respect to the leaflet-flexibility value of each other leaflet in the designated leaflet group.

In an application, outputting the indication of the designated leaflet groups includes, using at least one indicator in communication with the computer processor, indicating the designated leaflet groups.

In an application, the group size value is three, and receiving the group size value includes receiving the group size value that is three.

In an application, group size value is two, and receiving the group size value includes receiving the group size value that is two.

In an application, group size value is four, and receiving the group size value includes receiving the group size value that is four.

In an application, designating at least some of the leaflets of the aggregate into designated leaflet groups includes designating fewer than 80 percent of the leaflets of the aggregate into designated leaflet groups.

In an application, designating fewer than 80 percent of the leaflets of the aggregate into designated leaflet groups includes designating 10-80 percent of the leaflets of the aggregate into designated leaflet groups.

In an application, designating fewer than 80 percent of the leaflets of the aggregate into designated leaflet groups includes designating fewer than 50 percent of the leaflets of the aggregate into designated leaflet groups.

In an application, designating fewer than 50 percent of the leaflets of the aggregate into designated leaflet groups includes designating 10-50 percent of the leaflets of the aggregate into designated leaflet groups.

In an application, designating fewer than 50 percent of the leaflets of the aggregate into designated leaflet groups includes designating fewer than 30 percent of the leaflets of the aggregate into designated leaflet groups.

In an application, the method includes, prior to deriving the leaflet-flexibility value for each leaflet of the aggregate of leaflets, calculating the image parameter for each leaflet of the aggregate by digitally analyzing one or more digital images that include the leaflets of the aggregate.

In an application, the method includes, prior to deriving the leaflet-flexibility value for each leaflet of the aggregate of leaflets, performing an image-quality check routine, and performing the image-quality check routine includes:
comparing, for each leaflet of the aggregate, the image parameter to a predetermined threshold;

and deriving the leaflet-flexibility value for each leaflet of the aggregate of leaflets includes selectively deriving the leaflet-flexibility value for each leaflet, such that:

if the image parameter for a given leaflet is found to fit the predetermined threshold, the leaflet-flexibility value is derived for that leaflet, and if the image parameter for a given leaflet is found to not fit the predetermined threshold, the leaflet-flexibility value is not derived for that leaflet.

In an application:

calculating the image parameter for each leaflet of the aggregate includes:

calculating, for each leaflet of the aggregate:
a direct distance between a position of a first leaflet-tip and a position of a second leaflet-tip, and
an axial distance along a horizontal axis between the position of the first leaflet-tip and the position of the second leaflet-tip, and
comparing, for each leaflet of the aggregate, the direct distance to the axial distance.

In an application, calculating the image parameter for each leaflet of the aggregate includes calculating, for each leaflet of the aggregate, a direct distance between a position of a first leaflet-tip and a position of a second leaflet-tip.

In an application, calculating the image parameter for each leaflet of the aggregate includes calculating, for each leaflet of the aggregate, an axial distance along a horizontal axis between a position of a first leaflet-tip and a position of a second leaflet-tip.

In an application, the method includes, prior to calculating the image parameter for each leaflet of the aggregate, using an image sensor to acquire the one or more digital images.

In an application, the aggregate of leaflets includes a first batch of leaflets and a second batch of leaflets, and acquiring the one or more digital images includes:

acquiring a first digital image that includes leaflets of the first batch of leaflets; and acquiring a second digital image that includes leaflets of the second batch of leaflets.

In an application:

the first digital image includes all of the leaflets of the first batch of leaflets, and acquiring the first digital image includes acquiring the digital image that includes all of the leaflets of the first batch of leaflets; and the second digital image includes all of the leaflets of the second batch of leaflets, and acquiring the second digital image includes acquiring a digital image that includes all of the leaflets of the second batch of leaflets.

In an application, the method includes, subsequently to acquiring the first digital image, for each leaflet of the first batch of leaflets, indicating a respective portion of a storage array in which to temporarily store the leaflet of the first batch of leaflets.

In an application, outputting the indication of the designated leaflet groups includes indicating the respective portion of the storage array from which to group leaflets of the first batch of leaflets into the designated leaflet groups.

In an application, the method includes, prior to the step of designating:

assigning a respective index to each of the leaflet-flexibility values, each of the indices representing a respective one of the leaflets and having the leaflet-flexibility value of the respective one of the leaflets;

receiving an intra-group tolerance, the intra-group tolerance representing a maximum allowable difference between the leaflet-flexibility values of any two leaflets in a given leaflet group;

subsequently, determining a maximum number of within-tolerance index groups attainable from the indices, a within-tolerance index group being an index group (i) that includes a number of indices that is equal to the group size value, and (ii) for which the flexibility value of each index in the index group is within the intra-group tolerance with respect to the leaflet-flexibility value of each other index in the index group; and subsequently, storing the maximum number, and designating at least some of the leaflets of the aggregate into designated leaflet groups includes designating at least some of the leaflets of the aggregate into designated leaflet groups, such that:

for each of the designated leaflet groups, the flexibility value of each index in the designated index group is within the intra-group tolerance with respect to the leaflet-flexibility value of each other index in the designated index group, and a total number of the designated index groups is at least half of the stored maximum number.

In an application:

assigning the respective index to each of the leaflet-flexibility values includes arranging the indices in an ordered series in which the indices are ordered according to an order of magnitude of the respective leaflet-flexibility values; and determining the maximum number includes iteratively:

counting a number of successive remaining indices, a successive remaining index being defined as an index that (i) has not yet been counted as an index of a within-tolerance index group, and (ii) being positioned later in the ordered series than any index that has already been counted as an index of a within-tolerance index group selecting a potential index group from among the successive remaining indices, such that:

a lowest index of a potential index group is the index of the potential index group that has a lowest leaflet-flexibility value of the indices of the potential index group, and a highest index of the potential index group is the index of the potential index group that has a highest leaflet-flexibility value of the indices of the potential index group, the potential index group includes a number of successive indices equal to the group size, and the lowest index of the potential index group is the lowest remaining index;

calculating a group-differential of the potential index group, the group-differential being a difference between (i) the leaflet-flexibility value of the highest index of the potential index group, and (ii) the leaflet-flexibility value of the lowest index of the potential index group;

determining whether the group-differential of the potential index group is greater than, or no greater than, the intra-group tolerance, and responsively:

if the group-differential of the potential index group is no greater than the intra-group tolerance, counting the potential index group as a within-tolerance index group, and if the group-differential of the potential index group is greater than the intra-group tolerance, not counting the potential index group as a within-tolerance index group;

responsively to (i) the step of counting the potential index group, and (ii) the identifying the number of successive remaining indices, selectively selecting a successive potential index group including a remaining index, and selectively selecting the successive potential index group includes:
- if a preceding potential index group is counted as a within-tolerance index group, and the number of successive remaining indices is at least equal to the group size value, selecting the successive potential index group, the lowest index of the successive potential index group immediately succeeding the highest index of the preceding potential index group,
- if the preceding potential index group is counted as a within-tolerance index group, and the number of successive remaining indices is less than the group size value, concluding the determining the maximum number,
- if the preceding potential index group is not counted as a within-tolerance index group, and the number of successive remaining indices is at least equal to the group size value, selecting the successive potential index group, the lowest index of the successive potential index group immediately succeeding the lowest index of the preceding potential index group,
- if the preceding potential index group is not counted as a within-tolerance index group, and no remaining index is identified, concluding the determining the maximum number, until the number of successive remaining indices is less than the group size value.

In an application, organizing the indices according to an order of magnitude of the values includes organizing the indices according to an ascending order of magnitude of the values.

In an application, organizing the indices according to an order of magnitude of the values includes organizing the indices according to a descending order of magnitude of the values.

In an application:
an average differential value, of a given index group, is calculated by averaging differences between leaflet-flexibility values assigned to each pair of indices including that index group,
designating the at least some of the leaflets of the aggregate into designated leaflet groups includes designating the at least some of the leaflets of the aggregate into designated leaflet groups such that:
- a cumulative average differential value of the designated index groups, calculated by averaging the average differential values of each of the designated index groups, is less than:
- the cumulative average differential value of the within-tolerance index groups, calculated by averaging the average differential values of each of the within-tolerance index group.

In an application, designating the at least some of the leaflets of the aggregate into designated leaflet groups includes designating the at least some of the leaflets of the aggregate into designated leaflet groups, such that a total number of the designated index groups is:
- at least half of the stored maximum number, and
- no greater than the stored maximum number.

In an application, designating the at least some of the leaflets of the aggregate into designated leaflet groups includes designating the at least some of the leaflets of the aggregate into designated leaflet groups, such that a total number of the designated index groups is at least sixty percent of the stored maximum number.

In an application, designating the at least some of the leaflets of the aggregate into designated leaflet groups includes designating the at least some of the leaflets of the aggregate into designated leaflet groups, such that a total number of the designated index groups is at least seventy percent of the stored maximum number.

In an application, designating the at least some of the leaflets of the aggregate into designated leaflet groups includes designating the at least some of the leaflets of the aggregate into designated leaflet groups, such that a total number of the designated index groups is at least eighty percent of the stored maximum number.

In an application, designating the at least some of the leaflets of the aggregate into designated leaflet groups includes designating the at least some of the leaflets of the aggregate into designated leaflet groups, such that a total number of the designated index groups is at least ninety percent of the stored maximum number.

In an application, designating the at least some of the leaflets of the aggregate into designated leaflet groups includes designating the at least some of the leaflets of the aggregate into designated leaflet groups, such that a total number of the designated index groups is equal to the stored maximum number.

In an application, designating at least some of the leaflets of the aggregate into designated leaflet groups includes designating the at least some of the leaflets of the aggregate into designated leaflet groups, such that a total number of designated leaflet groups is at least sixty percent of the stored maximum number.

In an application, designating at least some of the leaflets of the aggregate into designated leaflet groups includes designating the at least some of the leaflets of the aggregate into designated leaflet groups, such that the total number of designated leaflet groups is at least seventy percent of the stored maximum number.

In an application, designating at least some of the leaflets of the aggregate into designated leaflet groups includes designating the at least some of the leaflets of the aggregate into designated leaflet groups, such that the total number of designated leaflet groups is at least eighty percent of the stored maximum number.

In an application, designating at least some of the leaflets of the aggregate into designated leaflet groups includes designating the at least some of the leaflets of the aggregate into designated leaflet groups, such that the total number of designated leaflet groups is at least ninety percent of the stored maximum number.

In an application, designating at least some of the leaflets of the aggregate into designated leaflet groups includes designating the at least some of the leaflets of the aggregate into designated leaflet groups, such that the total number of designated leaflet groups is equal to the stored maximum number.

In an application:
assigning the respective index to each of the leaflet-flexibility values includes arranging the indices in an ordered series in which the indices are ordered according to an order of magnitude of the respective leaflet-flexibility values; and
designating at least some of the leaflets of the aggregate into designated leaflet groups includes, starting at the beginning of the ordered series, iteratively:
(a) selecting a preliminary index group from among remaining indices, a remaining index being defined as an index that is positioned later, in the ordered series, than any index that has previously been selected as an index of a preliminary index group, and selecting of the preliminary index group is such that:
  a lowest index of the preliminary index group is the index of the preliminary index group that has a lowest leaflet-flexibility value of the indices of the preliminary index group, and a highest index of the preliminary index group is the index of the preliminary index group that has a highest leaflet-flexibility value of the indices of the preliminary index group,
  the preliminary index group includes a number of successive indices equal to the group size, and
  the lowest index of the preliminary index group is the lowest remaining index;
(b) determining if the leaflet-flexibility value of each index of the preliminary index group is within the intra-group tolerance with respect to the leaflet-flexibility value of each other index of the preliminary index group;
(c) counting a number of remaining indices;
(d) responsively to the step of the determining, and to the step of the counting, selectively selecting an index group from a cluster of indices, the cluster of indices including the preliminary index group and a predetermined number of successive indices, the lowest index of the preliminary index group is the lowest index of the cluster, and selectively selecting the index group from the cluster of indices includes:
if the flexibility value of each index of the preliminary index group is determined to be within the intra-group tolerance with respect to the leaflet-flexibility value of each other index of the preliminary index group, iteratively:
  (1) selecting, from the indices of the cluster, an index group that (i) has not previously been selected from the indices of the cluster, and (ii) has a group-differential that is no greater than the group-differential of any other index group that has not previously been selected from the cluster, a group-differential being a value that represents a difference between the leaflet-flexibility values of the indices of the index group,
  (2) determining whether designating the selected index group would reduce a total number of within-tolerance index groups that may be attained from the indices, compared to the maximum number;
  (3) in response to the determining whether designating the selected index group would reduce the total number of within-tolerance index groups attainable from the indices, selectively designating the selected index group, selectively designating the selected index group including:
    if designating the selected index group is determined to not reduce the total number of within-tolerance index groups attainable from the indices, designating the selected index group, and
    if designating the selected index group is determined to reduce the total number of within-tolerance index groups attainable from the indices, not designating the selected index group,
  until the selected index group of a given iteration of step (d) is designated, and
if the flexibility value of each index of the preliminary index group is
determined to not be within the intra-group tolerance with respect to the leaflet-flexibility value of each other index of the preliminary index group, repeating steps a-d;
until the counted number of remaining indices is less than the group size value.

In an application, determining whether designating the selected index group would reduce the total number of within-tolerance index groups that may be attained from the indices, compared to the maximum number, includes:
calculating a number of within-tolerance index groups that may be attained from the indices, should the selected index group be designated, by:
  (a) selecting a first potential index group from among successive indices, such that:
    the first potential index group includes a number of indices equal to the group size, and
    the lowest index of the first potential index group is the lowest remaining index;
  with regard to the first potential index group:
    (b) calculating the group-differential, the group-differential being a difference between (i) the leaflet-flexibility value of the highest index, and (ii) the leaflet-flexibility value of the lowest index;
    (c) determining whether the group-differential is greater than, or no greater than, the intra-group tolerance, and responsively:
      (d) if the group-differential is no greater than the intra-group tolerance, counting the potential index group as a within-tolerance index group that may be attained from the indices, and
      (e) if the group-differential is greater than the intra-group tolerance, not counting the potential index group as a within-tolerance index group that may be attained from the indices;
  (f) responsively to the counting the number of successive remaining indices, iteratively:
    selectively selecting a successive potential index group including a remaining index, such that:
      the successive potential index group includes a number of indices equal to the group size, and
      the lowest index of the successive potential index group is the lowest remaining index,
    selectively selecting the successive potential index group including:
      if a preceding potential index group is counted as a within-tolerance index group that may be attained from the indices should the best-matching index group be designated, and the number of successive remaining indices is at least equal to the group size value:
        selecting the successive potential index group, the lowest index of the successive potential index group immediately succeeding the highest index of the preceding potential index group, and
        repeating, with respect to the successive potential index group, steps b-e,
      if the preceding potential index group is not counted as a within-tolerance index group that may be attained from the indices, should the best-matching index group be designated, and the number of successive remaining indices is at least equal to the group size value:
        selecting the successive potential index group, the lowest index of the successive potential index group immediately succeeding the lowest index of the preceding potential index group, and
        repeating, with respect to the successive potential index group, steps b-e,
    until the number of successive remaining indices is less than the group size value;

comparing the number of within-tolerance index groups that may be attained from the indices, should the best-matching index group be designated, to the maximum number of within-tolerance groups; and responsively to the step of comparing:
if the number of within-tolerance index groups that may be attained from the indices, should the best-matching index group be designated, is no less than the maximum number of within-tolerance groups, determining that the selected index group would not reduce the total number of within-tolerance index groups attainable from the indices, and if the number of within-tolerance index groups that may be attained from the indices, should the best-matching index group be designated, is less than the maximum number of within-tolerance groups, determining that the selected index group would reduce the total number of within-tolerance index groups attainable from the indices.

In an application, identifying the best-matching index group from the cluster of indices includes:
calculating, for each index group including a number of indices equal to the group size value, attainable from the cluster of indices, a parameter;
identifying the one index group of the index groups having a lowest parameter value as the best-matching index group.

In an application, calculating, for each index group, the parameter, includes calculating, for each index group, a group-differential, the group-differential being a difference between (i) the leaflet-flexibility value of the highest index of the potential index group, and (ii) the leaflet-flexibility value of the lowest index of the potential index group.

In an application, calculating, for each index group, the parameter, includes calculating, for each index group, an average differential value by averaging differences between leaflet-flexibility values assigned to each pair of indices including that index group.

In an application, calculating, for each index group, the parameter, includes calculating, for each index group, a sum of a square of a difference between leaflet-flexibility values assigned to respective pairs of indices of each of a plurality of pairs of indices including the index group.

There is further provided, in accordance with an application of the present invention, a system for use with a plurality of prosthetic heart valve leaflets, the system including:
a storage array, the storage array including:
a plurality of cells, each cell configured to contain exactly one of the leaflets; and
a plurality of indicators, each of the indicators associated with a corresponding one of the cells; and
circuitry, in communication with the plurality of indicators, and configured to:
receive a group size value,
using one or more leaflet-flexibility values that each corresponds to a respective one of the leaflets, designate at least some of the leaflets into leaflet groups, each of the leaflet groups including a number of leaflets equal to the group size value, and
for each of the leaflet groups, drive the indicators to indicate which of the cells contain leaflets designated the leaflet group.

In an application, the circuitry is configured to, for each respective one of the leaflets: receive a digital image, by digitally analyzing the digital image, calculate an image parameter for the leaflet, and
from the image parameter, derive the one or more leaflet-flexibility values that corresponds to the leaflet.

In an application, the apparatus includes an image sensor in communication with the circuitry, the image sensor configured to acquire, for each respective one of the leaflets, the digital image, and to communicate the digital image to the circuitry.

In an application, the plurality of indicators include a user-interface, the user-interface configured to facilitate switching from indicating which of the cells contain leaflets designated to a first leaflet group, to indicating which of the cells contain leaflets designated to a second leaflet group.

In an application, each cell is fillable with a sterile liquid.

In an application, the plurality of indicators include a user-interface, the user-interface configured to facilitate switching from indicating the designation of at least some of the leaflets into a first leaflet group, to indicating the designation of at least some of the leaflets into a second leaflet group.

In an application, the plurality of indicators includes a respective indicator for each cell, each respective indicator an integral component of the storage array.

In an application:
the plurality of indicators include a respective indicator for each cell,
each indicator is configured to provide a respective visual cue, with respect to each leaflet, and
the storage array is configured to be juxtaposed with the plurality of indicators, and the storage array is at least partially transparent, such that the visual cue indicated by each indicator, with respect to each leaflet, is visible through the storage array.

In an application, each cell is labelled with a unique identifier, each unique identifier corresponding to:
a given batch of leaflets, and
a given leaflet of that batch.

In an application, the storage array includes a plurality of zones, each zone:
corresponding to a given batch of leaflets, and
including a number of cells equal to a number of leaflets including that batch.

In an application, the storage array is configured to be placed on the plurality of indicators, such that the visual cue provided by each indicator, with respect to each leaflet, is visible through a floor of the storage array.

In an application, the plurality of indicators and the storage array are complimentarily dimensioned in a manner that facilitates integration of the storage array with the plurality of indicators, such that the visual cue provided by each indicator, with respect to each leaflet, is visible through the cell containing that respective leaflet.

There is further provided, in accordance with an application of the present invention, a method for sorting leaflets for use in prosthetic heart valves, the method including:
positioning, opposite an image sensor, each leaflet of a first batch of multiple leaflets;
subsequently, initiating acquisition, by the image sensor, of a first digital image that includes all of the leaflets of the first batch;
subsequently, positioning, opposite the image sensor, each leaflet of a second batch of multiple leaflets;
subsequently, initiating acquisition, by the image sensor, of a second digital image that includes all of the leaflets of the second batch;
for each leaflet of the first batch and each leaflet of the second batch:

obtaining a leaflet-flexibility value for the leaflet, the leaflet-flexibility value being derived by digital analysis of the first digital image or the second digital image, assigning the leaflet to a leaflet-flexibility category such that the leaflet-flexibility value of the leaflet fits within a range defined between an upper flexibility-value threshold of the leaflet-flexibility category, and a lower flexibility-value threshold of the leaflet-flexibility category, the leaflet-flexibility category being one of multiple leaflet-flexibility categories;

placing the leaflet into a storage unit according to the leaflet-flexibility category of the leaflet, in a manner that facilitates:
- separation of the leaflet from leaflets assigned to other leaflet-flexibility categories, and
- maintenance of one or more attributes selected from the group consisting of:
  - moisture content of the leaflet, and
  - sterility of the leaflet.

In an application, the method includes:

selecting, from the storage unit, a group of leaflets including a number of leaflets equal to the number of leaflets required for a prosthetic heart valve, each leaflet of the group having been assigned to the same leaflet-flexibility category; and sewing the group of leaflets into the prosthetic heart valve.

In an application, the method includes:

selecting, from the storage unit, a first categorized batch of multiple categorized leaflets, each categorized leaflet of the first categorized batch having been assigned to the same leaflet-flexibility category as the other categorized leaflets of the first categorized batch;

positioning each categorized leaflet of the first categorized batch opposite the image sensor;

subsequently, initiating acquisition, by the image sensor, of a third digital image that includes all of the categorized leaflets of the first categorized batch;

subsequently, removing each categorized leaflet of the first categorized batch to a storage array in a manner that facilitates tracking of an individual identity of each categorized leaflet of the first categorized batch;

subsequently selecting, from the storage unit, a second categorized batch of multiple categorized leaflets, each categorized leaflet of the second categorized batch being assigned to the same leaflet-flexibility category as the categorized leaflets of the first categorized batch;

positioning each categorized leaflet of the second categorized batch of categorized leaflets opposite the image sensor;

subsequently, initiating acquisition, by the image sensor, of a fourth digital image that includes all of the categorized leaflets of the second categorized batch;

subsequently, removing the categorized leaflets of the second categorized batch to the storage array in a manner that facilitates tracking of the individual identity of each categorized leaflet of the second categorized batch, thereby assembling the categorized leaflets of the first categorized batch and the categorized leaflets of the second categorized batch into an aggregate of categorized leaflets;

subsequently, operating software to:
- receive the third digital image and the fourth digital image,
- by digitally analyzing the third digital image and the fourth digital image, for each of the categorized leaflets included in the third digital image and the fourth digital image:
  - calculate an image parameter for the categorized leaflet, and
  - from the image parameter, derive a leaflet-flexibility value for the categorized leaflet,
- receive a group size value,
- designate at least some of the categorized leaflets of the aggregate of categorized leaflets into one or more designated leaflet groups:
  - based on similarity between the respective leaflet-flexibility values of each of the categorized leaflets of the aggregate, and
  - such that each of the designated leaflet groups includes a number of categorized leaflets equal to the group size value, and
- output an indication of the one or more designated leaflet groups; and in response to the indication, grouping the at least some categorized leaflets of the aggregate of categorized leaflets into the one or more designated leaflet groups.

In an application:

positioning each leaflet of a first batch of leaflets opposite an image sensor;

subsequently, initiating acquisition, by the image sensor, of a first digital image that includes all of the leaflets of the first batch;

subsequently, removing each leaflet of the first batch to a storage array in a manner that facilitates tracking of an individual identity of each leaflet of the first batch;

positioning each leaflet of a second batch of leaflets opposite the image sensor;

subsequently, initiating acquisition, by the image sensor, of a second digital image that includes all of the leaflets of the second batch;

subsequently, removing the leaflets of the second batch to the storage array in a manner that facilitates tracking of the individual identity of each leaflet of the second batch, thereby assembling the leaflets of the first batch and the leaflets of the second batch into an aggregate of leaflets;

subsequently, operating software to:
- receive the first digital image and the second digital image,
- by digitally analyzing the first digital image and the second digital image, for each of the leaflets included in the first digital image and the second digital image:
  - calculate an image parameter for the leaflet, and
  - from the image parameter, derive a leaflet-flexibility value for the leaflet, receive a group size value,
- designate at least some of the leaflets of the aggregate of leaflets into one or more designated leaflet groups:
  - based on similarity between the respective leaflet-flexibility values of each of the leaflets of the aggregate, and
  - such that each of the leaflet groups includes a number of leaflets equal to the group size value, and
- output an indication of the one or more designated leaflet groups; and in response to the indication, grouping the at least some leaflets of the aggregate of leaflets into the one or more designated leaflet groups.

In an application, the method includes, subsequently to grouping the at least some leaflets of the aggregate of leaflets into the one or more designated leaflet groups, sewing the leaflets of each designated leaflet group into a respective prosthetic heart valve.

In an application, the method includes, prior to positioning each leaflet of the first batch of leaflets opposite the image sensor:

classifying leaflets of a stock of leaflets, according to thickness, into thickness classes; and selecting the first batch of leaflets and the second batch of leaflets from a single one of the thickness classes.

In an application, the method includes, prior to positioning each leaflet of the first batch of leaflets opposite the image sensor:

assigning leaflets of a stock of leaflets, according to the leaflet-flexibility value of each respective leaflet, to leaflet-flexibility categories; and selecting the first batch of leaflets and the second batch of leaflets from a single one of the leaflet-flexibility categories.

In an application:

operating the software to designate the at least some of the leaflets of the aggregate of leaflets into one or more designated leaflet groups, based on similarity between the respective leaflet-flexibility values of each of the leaflets of the aggregate, includes operating the software to designate the at least some of the leaflets of the aggregate of leaflets into one or more designated leaflet groups, based on an intra-group tolerance that represents a maximum allowable difference between leaflet-flexibility values of indices of a leaflet group; and operating the software includes operating the software to, prior to outputting the indication of the one or more designated leaflet groups, display a preview relating to the one or more designated leaflet groups, and the method includes, prior to grouping the at least some leaflets of the aggregate of leaflets into the one or more designated leaflet groups, adjusting the intra-group tolerance responsively to the preview relating to the one or more designated leaflet groups.

In an application:

operating the software to display the preview relating to the one or more designated leaflet groups includes operating the software to display the preview relating to a yield of preliminary leaflet groups; and adjusting the intra-group tolerance responsively to the preview relating to the designated leaflet groups includes adjusting the intra-group tolerance responsively to the preview relating to the yield of the preliminary leaflet groups.

In an application:

operating the software to display the preview relating to the one or more designated leaflet groups includes operating the software to display the preview relating to a closeness of fit of preliminary leaflet groups; and adjusting the intra-group tolerance responsively to the preview relating to the designated leaflet groups includes adjusting the intra-group tolerance responsively to the preview relating to the closeness of fit of the preliminary leaflet groups.

In an application, assembling the leaflets of the first batch and the leaflets of the second batch into the aggregate of leaflets includes temporarily storing each leaflet of the aggregate in the storage array in a manner that facilitates maintenance of one or more attributes selected from the group consisting of: moisture content of the leaflets, and sterility of each leaflet.

In an application, the method includes operating the software to indicate, on at least one indicator, a respective portion of the storage array in which each leaflet of the aggregate is to be temporarily stored; and temporarily storing each leaflet of the aggregate in the storage array includes temporarily storing the leaflet in the respective portion of the storage array.

In an application:

the storage array includes a plurality of storage cells, operating the software to indicate, on at least one indicator, the respective portion of the storage array in which each leaflet of the aggregate is to be temporarily stored includes operating the software to indicate a respective storage cell of the plurality of storage cells in which each leaflet of the aggregate is to be temporarily stored; and temporarily storing each leaflet of the aggregate in the respective portion of the storage array includes temporarily storing each leaflet of the aggregate in the respective storage cell.

In an application, assembling the leaflets of the first batch and the leaflets of the second batch into the aggregate of leaflets includes assembling more than forty leaflets and fewer than four hundred leaflets into the aggregate of leaflets.

In an application, assembling the leaflets of the first batch and the leaflets of the second batch into the aggregate of leaflets includes assembling more than forty leaflets and fewer than one hundred leaflets into the aggregate of leaflets.

In an application, assembling the leaflets of the first batch and the leaflets of the second batch into the aggregate of leaflets includes assembling eighty-one leaflets into the aggregate of leaflets.

In an application, operating software to output the indication of the one or more designated leaflet groups includes operating software to output the indication of the one or more designated leaflet groups on at least one indicator.

In an application, operating software to output the indication of the one or more designated leaflet groups on at least one indicator includes operating software to switch between indicating leaflets designated to a first of the designated leaflet groups, and indicating leaflets designated to a second of the leaflet groups.

In an application, operating software to output the indication of the one or more designated leaflet groups on at least one indicator, includes using a respective indicator for each leaflet of the aggregate of leaflets, operating software to output the indication of the designated leaflet group to which each leaflet of the aggregate of leaflets is designated.

In an application, using the respective indicator for each leaflet of the aggregate of leaflets, operating software to output the indication of the designated leaflet group to which each leaflet of the aggregate of leaflets is designated includes using the respective indicator for each leaflet of the aggregate of leaflets, providing a visual cue indicating the respective designated leaflet group to which each leaflet of the aggregate of leaflets is designated.

In an application, grouping the at least some leaflets of the aggregate of leaflets into the one or more designated leaflet groups, includes grouping the at least some leaflets of the aggregate of leaflets, from the storage array, into the one or more designated leaflet groups, responsively to the indication of the designated leaflet group to which each leaflet of the aggregate of leaflets is designated.

In an application:

positioning each leaflet of the first batch of leaflets opposite the image sensor includes draping each leaflet of the first batch of leaflets over a respective bar of a plurality of bars, opposite the image sensor; and positioning each leaflet of the second batch of leaflets opposite the image sensor includes draping each leaflet of the second batch of leaflets over a respective bar of the plurality of bars, opposite the image sensor.

In an application:

draping each leaflet of the batch of leaflets over the respective bar of the plurality of bars includes draping each leaflet of the first batch of leaflets, in a first orientation, over the respective bar of the plurality of bars;

draping each leaflet of the second batch of leaflets over a respective bar of the plurality of bars includes draping each leaflet of the second batch of leaflets, in the first orientation, over the respective bar of the plurality of bars;

operating the software to receive the first digital image and the second digital image includes operating the software to receive a first first-orientation digital image of the first batch of leaflets, in the first orientation, over the respective bar of the plurality of bars and a second first-orientation digital image of the second batch of leaflets, in the first orientation, over the respective bar of the plurality of bars;

operating the software to calculate an image parameter for each leaflet, by digitally analyzing the first digital image and the second digital image, includes operating the software to calculate a first-orientation image parameter for each leaflet by digitally analyzing the first first-orientation digital image and the second first-orientation digital image;

operating the software to derive a leaflet-flexibility value for each leaflet, from the image parameter, includes operating the software to derive a first-orientation leaflet-flexibility value for each leaflet, from the first-orientation image parameter; and the method includes, subsequently to grouping the at least some leaflets of the aggregate of leaflets into the leaflet groups, validating the leaflets, by:
 draping each leaflet of the at least some leaflets, in a second orientation that is inverted with respect to the first orientation, over a respective bar of the plurality of bars;
 operating the software to:
  receive a second-orientation digital image of the at least some leaflets draped, in the second orientation, over the respective bars;
  calculate a second-orientation image parameter for each leaflet of the at least some leaflets by digitally analyzing the second-orientation digital image;
  derive a second-orientation leaflet-flexibility value for each leaflet of the at least some leaflets, from the second-orientation image parameter;
 comparing, for each leaflet of the at least some leaflets, the first-orientation leaflet-flexibility value and the second-orientation leaflet-flexibility value;
 responsively to the comparing, selectively counting a given leaflet of the at least some leaflets as a validated leaflet, the selectively counting including:
  if, for the given leaflet, a difference between the first-orientation leaflet-flexibility value and the second-orientation leaflet-flexibility value is below a predetermined threshold, counting the leaflet as a validated leaflet, and
  if, regarding the given leaflet, the difference between the first-orientation leaflet-flexibility value and the second-orientation leaflet-flexibility value exceeds the predetermined threshold, discarding the leaflet.

In an application:
 draping each leaflet of the first batch of leaflets, in the first orientation, over the respective bar of the plurality of bars, includes draping each leaflet of the first batch of leaflets over the respective bar of the plurality of bars with a rough side of the leaflet face-up;
 draping each leaflet of the second batch of leaflets, in the first orientation, over the respective bar of the plurality of bars, includes draping each leaflet of the second batch of leaflets over the respective bar of the plurality of bars with the rough side of the leaflet face-up; and
 draping each leaflet of the at least some leaflets, in the second orientation that is inverted with respect to the first orientation, over the respective bar of the plurality of bars, includes draping each leaflet of the at least some leaflets over the respective bar of the plurality of bars with a smooth side of the leaflet face-up.

There is further provided, in accordance with an application of the present invention, a method for grouping prosthetic valve leaflets of an aggregate of prosthetic valve leaflets including a first batch of prosthetic valve leaflets and a second batch of prosthetic valve leaflets, the method including:
 acquiring a first digital image that includes all of the leaflets of the first batch;
 acquiring a second digital image that includes all of the leaflets of the second batch;
 calculating an image parameter for each leaflet of the aggregate by digitally analyzing the first digital image and the second digital image;
 in response to the image parameter, deriving, for each leaflet of the aggregate, a leaflet-flexibility value;
 receiving a group size value;
 designating at least some of the leaflets of the aggregate into leaflet groups, (i) based on similarity between the respective leaflet-flexibility value of each leaflet of the aggregate, and (ii) such that each of the leaflet groups includes a number of leaflets equal to the group size value; and
 outputting an indication of the designated leaflet groups.

There is further provided, in accordance with an application of the present invention, an apparatus for grouping prosthetic valve leaflets of an aggregate of prosthetic valve leaflets, the apparatus including a computer processor configured to:
 receive a plurality of leaflet-flexibility values, each of the leaflet-flexibility values corresponding to a respective leaflet of the aggregate;
 receive a group size value;
 assign a respective index to each of the leaflet-flexibility values, each index representing a respective one of the leaflets and having the leaflet-flexibility value of the respective one of the leaflets;
 receive an intra-group tolerance, the intra-group tolerance representing a maximum allowable difference between the leaflet-flexibility values of any two leaflets in a given leaflet group;
 subsequently, determine a maximum number of within-tolerance index groups attainable from the indices, a within-tolerance index group being an index group (i) that includes a number of indices that is equal to the group size value, and (ii) for which the flexibility value of each index in the index group is within the intra-group tolerance with respect to the leaflet-flexibility value of each other index in the index group; and
 subsequently, store the maximum number,
 designate at least some of the leaflets of the aggregate into designated leaflet groups, (i) based on similarity between the respective leaflet-flexibility value of each leaflet of the aggregate, (ii) such that:
  each of the designated leaflet groups includes a number of leaflets equal to the group size value, and
  the flexibility value of each index in a given designated index group is within the intra-group tolerance with respect to the leaflet-flexibility value of each other index in the designated index group; and
 output an indication of the designated leaflet groups.

There is further provided, in accordance with an application of the present invention, a computer software product including a non-transitory computer-readable medium in which program instructions are stored, which instructions, when read by a computer cause the computer to:

receive a plurality of leaflet-flexibility values, each leaflet-flexibility value corresponding to a respective leaflet of the aggregate;

receive a group size value;

assign a respective index to each of the leaflet-flexibility values, each index representing a respective one of the leaflets and having the leaflet-flexibility value of the respective one of the leaflets;

receive an intra-group tolerance, the intra-group tolerance representing a maximum allowable difference between the leaflet-flexibility values of any two leaflets in a given leaflet group;

subsequently, determine a maximum number of within-tolerance index groups attainable from the indices, a within-tolerance index group being an index group (i) that includes a number of indices that is equal to the group size value, and (ii) for which the flexibility value of each index in the index group is within the intra-group tolerance with respect to the leaflet-flexibility value of each other index in the index group; and subsequently, store the maximum number, designate at least some of the leaflets of the aggregate into designated leaflet groups, (i) based on similarity between the respective leaflet-flexibility value of each leaflet of the aggregate, (ii) such that:

each of the designated leaflet groups includes a number of leaflets equal to the group size value, and the flexibility value of each index in a given designated index group is within the intra-group tolerance with respect to the leaflet-flexibility value of each other index in the designated index group; and output an indication of the designated leaflet groups.

The present invention will be more fully understood from the following detailed description of applications thereof, taken together with the drawings, in which:

BRIEF DESCRIPTION OF THE DRAWINGS

FIGS. 3A-C are schematic illustrations of side, front, and top views, respectively, of the tester in the first state, in accordance with some applications of the invention;

FIGS. 4A-C are schematic illustrations showing an arrangement of a platform having a plurality of guides, with respect to a leaflet, in accordance with some applications of the invention;

FIGS. 6A-C are schematic illustrations showing use of the tester, in accordance with some applications of the invention;

FIGS. 7A-C are schematic illustrations showing image parameters that may be calculated by circuitry in order to derive a leaflet-flexibility value, in accordance with some applications of the invention;

FIGS. 8A-B are schematic illustrations of unsuitable leaflets, in accordance with some applications of the invention;

FIGS. 9A-B are schematic illustrations of leaflets whose image parameters and/or leaflet-flexibility values may not enable circuitry to accurately assign leaflets to a leaflet flexibility category, in accordance with some applications of the invention;

FIG. 11 is a schematic illustration of the use of the tester to designate the leaflets to leaflet groups according to leaflet-flexibility values of the leaflets, in accordance with some applications of the invention;

FIGS. 12A-B are graphs representing relationships between leaflet-flexibility values of a set of leaflets, and the leaflet-flexibility categories or leaflet groups to which the same leaflets are assigned, in accordance with some applications of the invention;

FIGS. 13A-B and 14A-B are schematic illustrations showing use of leaflet storage arrays to indicate individual leaflets as being designated to a particular leaflet group, in accordance with some applications of the invention;

FIG. 15 is a schematic illustration showing a process wherein the leaflets are sorted into categories, and subsequently designated to leaflet groups, in accordance with some applications of the invention FIGS. 17, 18, 19, 20A-D, 21A-J, 22 and 23A-B are flowcharts and schematic illustrations that illustrate techniques for designating groups of leaflets, in accordance with some applications of the invention.

DETAILED DESCRIPTION OF EMBODIMENTS

Reference is made to FIGS. 1A-B, 2, and 3A-C, which are schematic illustrations showing a tester 20 for testing flexibility of a plurality of prosthetic heart valve leaflets 30, in accordance with some applications of the invention.

Figure 1A:
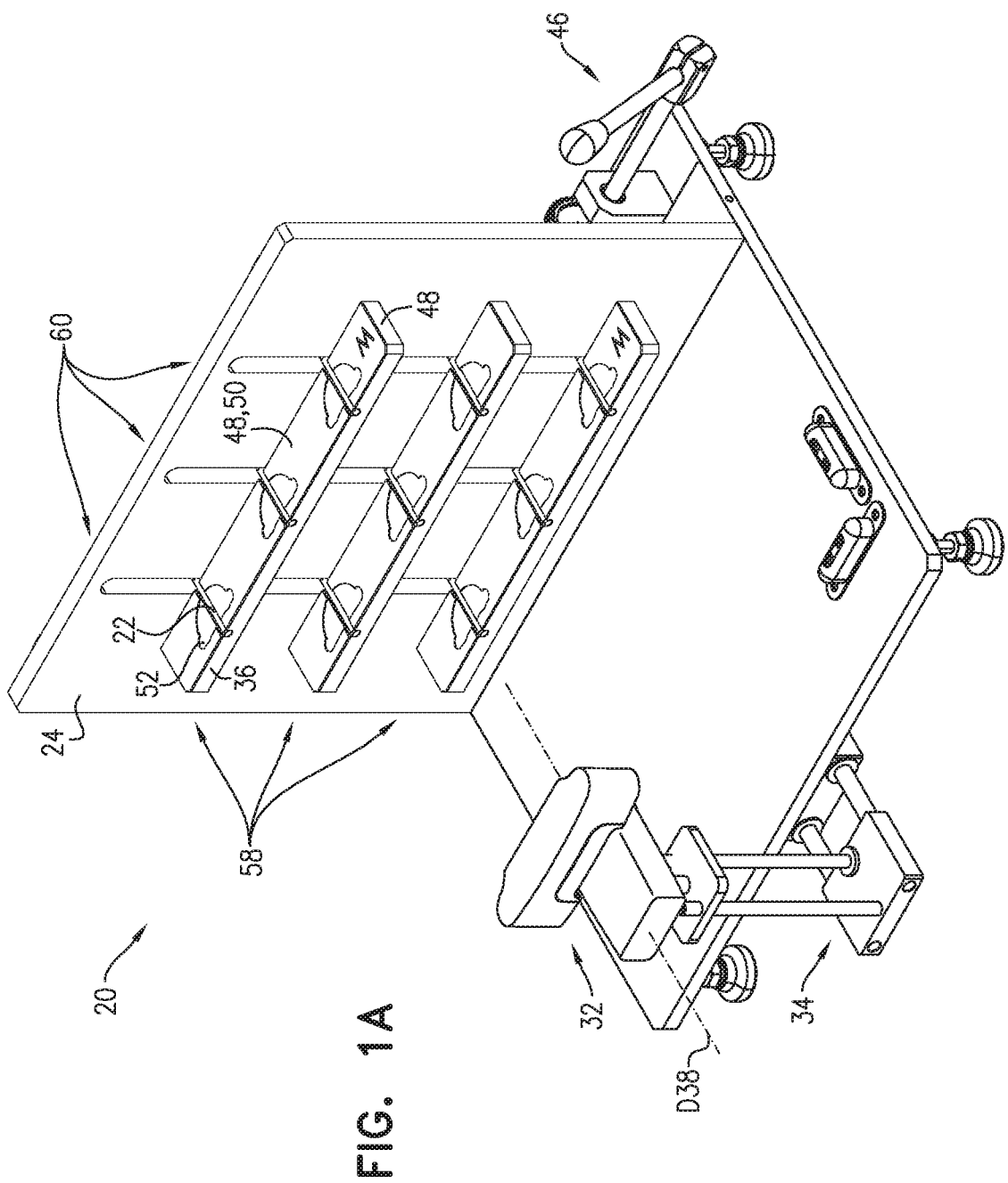
FIGS. 1A-B are schematic illustrations of a tester for testing flexibility of a plurality of prosthetic heart valve leaflets, in a first state and an elevated state, respectively, in accordance with some applications of the invention.
Figure 1B:
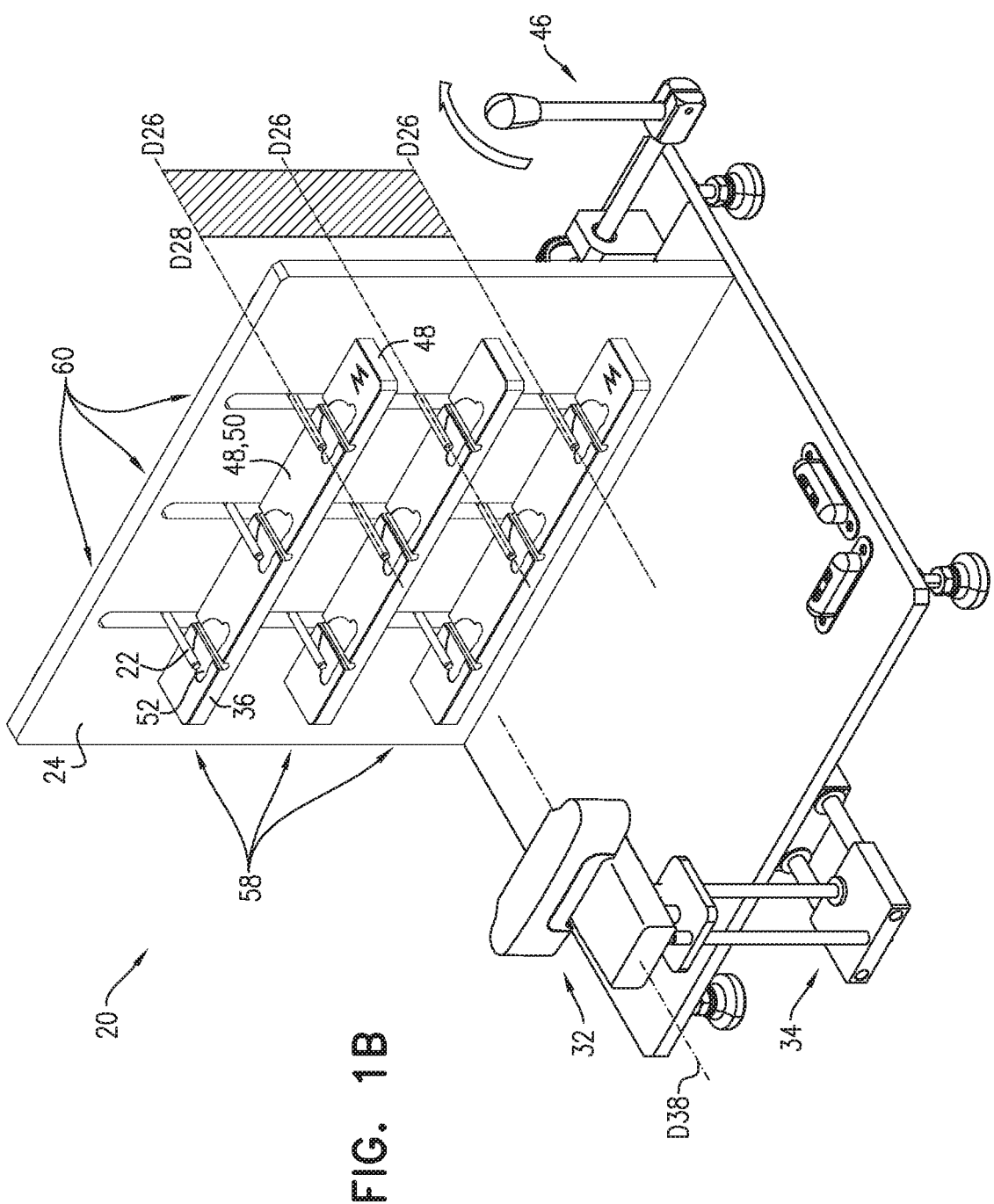
Figure 2:
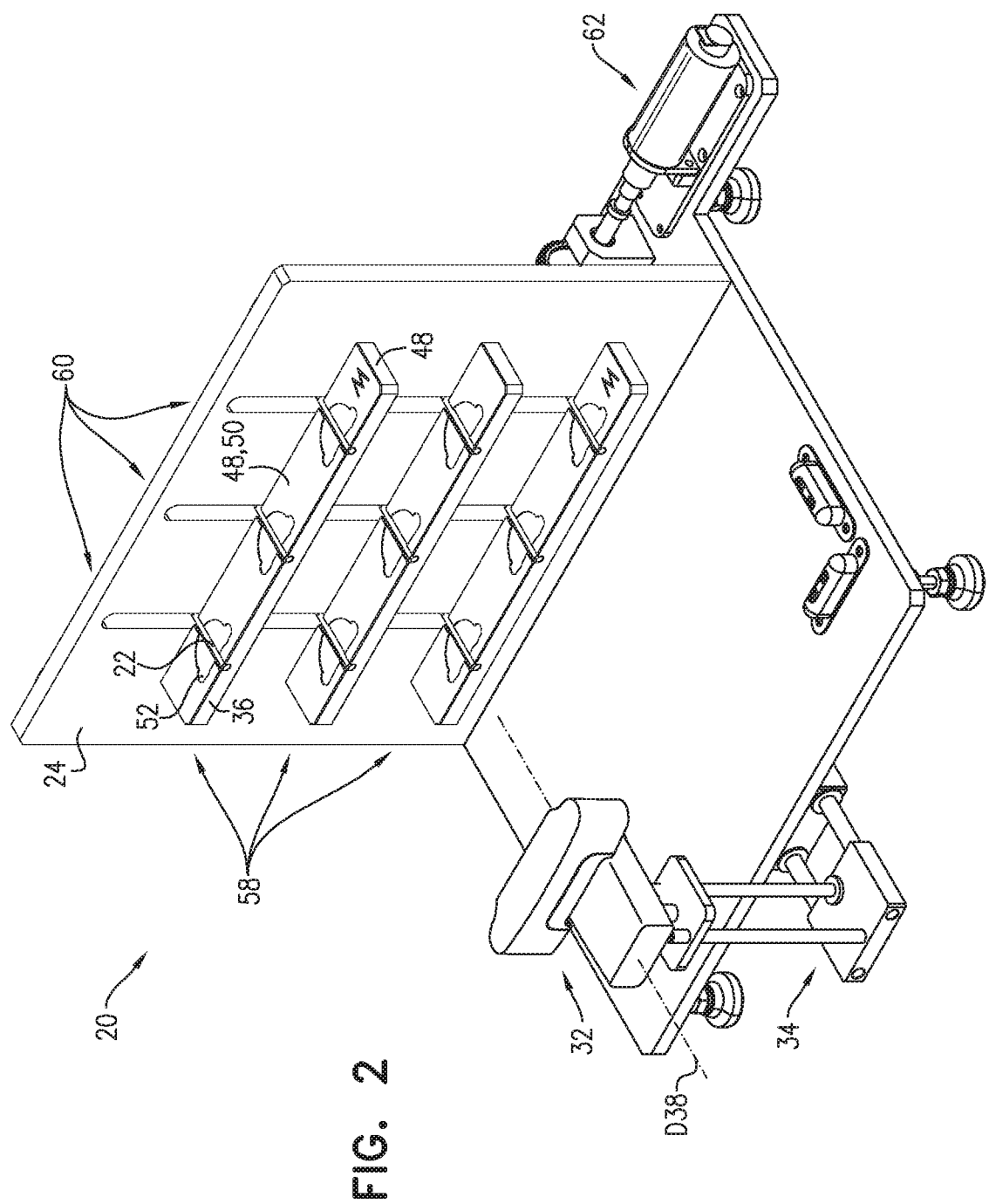
FIG. 2 is a schematic illustration of an alternative embodiment of the tester, in accordance with some applications of the invention.
Figure 3B:
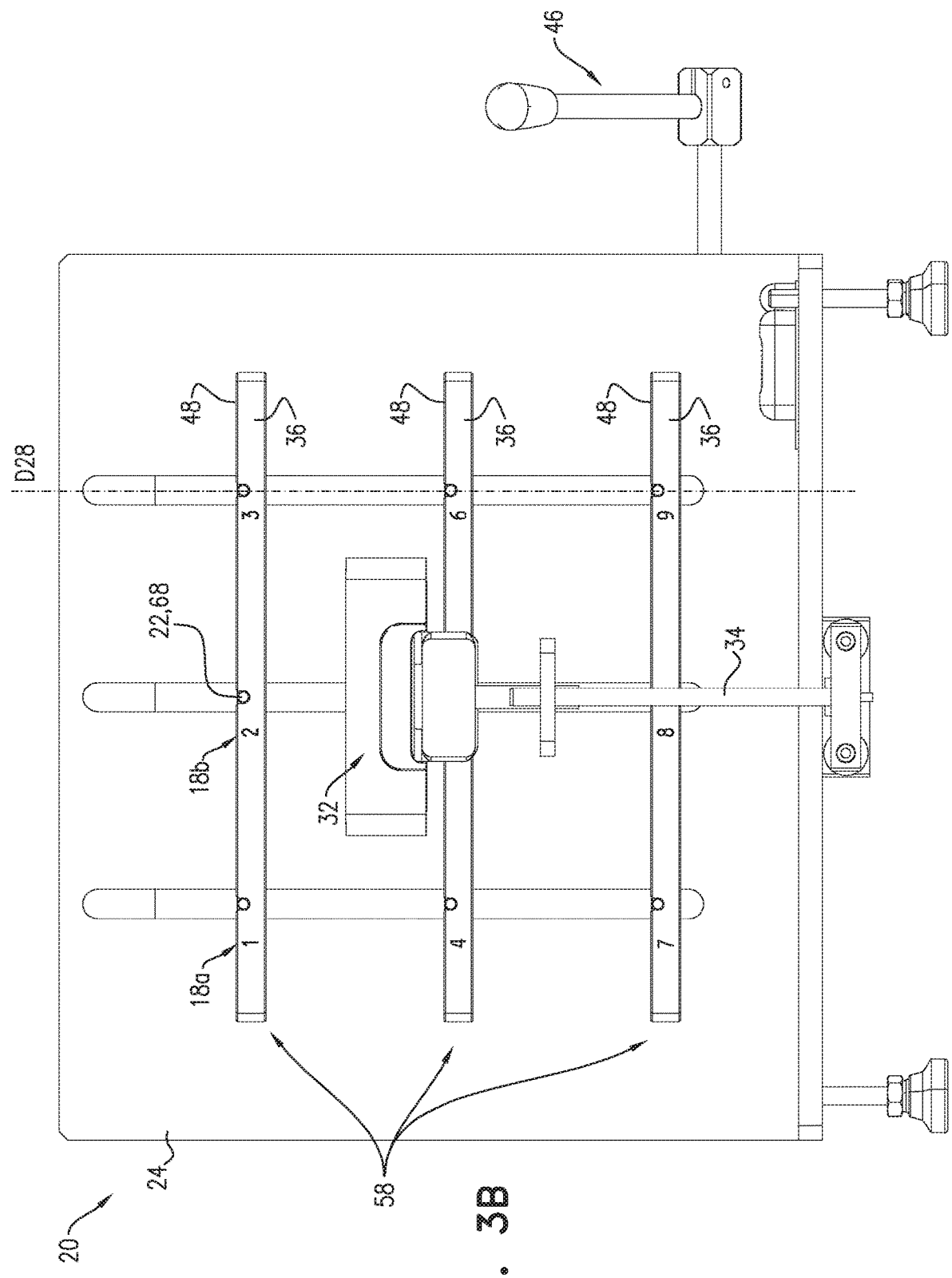
Figure 3C:
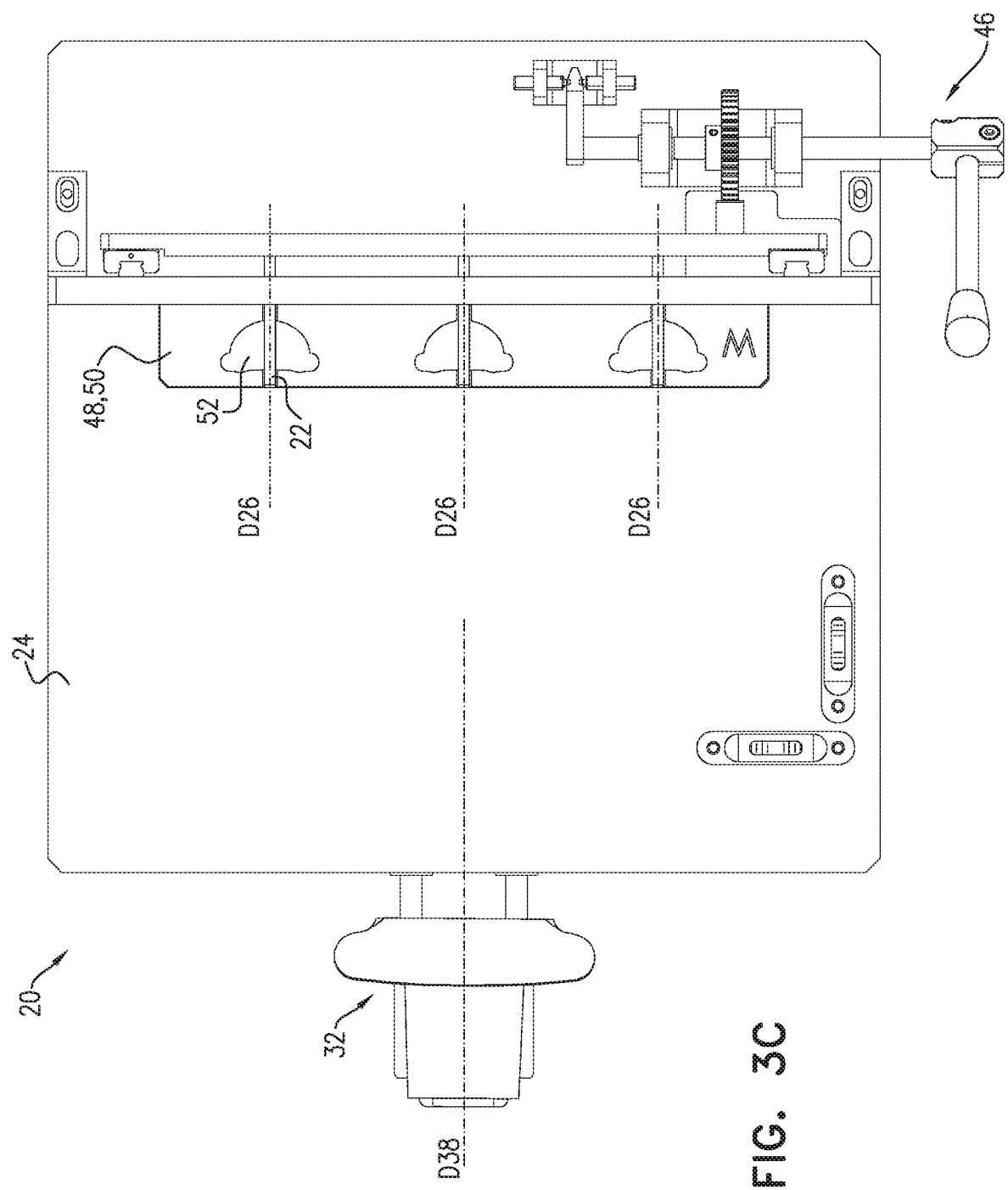

FIGS. 1A-B are perspective views of tester 20 in a first state and an elevated state, respectively. FIG. 2 is a perspective view of an alternative embodiment of tester 20. FIGS. 3A-C are side, front, and top views, respectively, of tester 20 in the first state.

Tester 20 comprises a plurality of horizontal bars 22 movably coupled to a vertical mount 24, in accordance with some applications of the invention. Typically, and as shown, each bar 22 extends away from mount 24 (e.g., perpendicularly from the mount) along a respective bar-axis D26, each bar-axis lying on a respective vertical bar-plane D28.

Tester 20 has a first state (FIG. 1A, 3A-C) and an elevated state (FIG. 1B). For some applications, and as shown, bars 22 are cylindrically shaped. For other applications, bars 22 may be of an alternate shape (e.g., rectangular prism, hexagonal prism or octagonal prism). Typically, actuation of an actuator 46 reversibly transitions tester 20 between the first state and the elevated state. Actuator 46 is shown as a manually-operated (e.g., mechanical) actuator. For some applications (FIG. 2), an electrical (e.g., motorized) actuator 62 may be used instead.

As shown in FIGS. 1A-B, transitioning of tester 20 between the first and elevated states includes vertical motion of each bars 22 along its vertical bar-plane D28 with respect to a platform 48. Typically, actuator 46 moves bars 22 upward with respect to the rest of tester 20, and platform 48 remains stationary. However, the scope of the invention includes actuator 46 moving platform 48 downward with respect to the rest of tester 20, while bars 22 remain stationary. Typically, and as shown, the platform is coupled to mount 24 such that each bar-plane D28 intersects the platform.

Tester 20 further comprises an image sensor 32, the image sensor positioned opposite mount 24, facing bars 22 and the mount. Orientation of image sensor 32 facing mount 24 and bars 22 facilitates the image sensor acquiring an image that includes leaflets 30 (e.g., all of the leaflets) draped over bars 22. Typically, and as shown, tester 20 further comprises a sensor-bracket 34, the sensor-bracket movably coupling image sensor 32 to the rest of tester 20 (e.g., to mount 24). Typically, sensor-bracket facilitates movement of image sensor 32 along a sensor-axis D38, moving the image sensor toward and away from mount 24. Sensor-bracket 34 typically facilitates movement of image sensor 32 (e.g., along sensor-axis D38) between (i) a position in which the image sensor can acquire an image that includes all of leaflets 30, and (ii) a position in which tester 20 is more compact—e.g., for when the tester is not in use. Typically, tester 20 is operated such that sensor 32 acquires an image that includes the multiple leaflets draped over bars 22. It is hypothesized by the inventors that acquiring and processing an image that includes multiple leaflets increases work throughput and/or improves accuracy of leaflet flexibility testing.

Typically, and as shown, mount 24 is generally flat, and bars 22 are generally parallel with each other. For some applications, mount 24 may be concave toward sensor 32, and bar-tips are arranged correspondingly to the concave surface of the mount, e.g., pointing toward the sensor. It is hypothesized by the inventors that, for some applications, mount 24 being concave may facilitate visualization of all leaflets 30 and bar-tips 68, from a single point of view—i.e., by sensor 32.

Some embodiments of the invention may comprise a plurality of image sensors 32. For example, the number of image sensors 32 may correspond to the number of bars 22.

Reference is made to FIGS. 4A-C, which are schematic illustrations showing the arrangement of platform 48 with respect to bars 22 and mount 24, in accordance with some applications of the invention. Typically, and as shown, bars 22 extend away from mount 24 in parallel with each other. For some applications, and as shown, bars 22 are arranged, with respect to the mount, in multiple rows 58 and multiple columns 60. For some applications in which bars 22 are arranged in multiple rows (i.e., such that bars 22 are stacked in at least one column), bars 22 may be arranged with respect to mount 24 such that the bar-planes D28 of the bars in a given column are coplanar—i.e., are disposed in a common bar-plane D28—as shown.

Although the Figures referred to herein depict an embodiment of tester 20 with bars 22 arranged in three rows 58 and three columns 60, this depiction is not intended to exclude other possible arrangements with either a smaller or greater number of rows 58 or columns 60 of bars 22. For some applications, and as shown, nine bars 22 may be arranged in rows 58 and columns 60 such that image sensor 32 may acquire an image including nine leaflets 30 tested simultaneously in a batch, each leaflet draped over a respective bar.

For other applications, a greater or lesser number of bars 22 may be arranged with respect to mount 24 of tester 20, facilitating increasing or decreasing the number of leaflets 30 tested simultaneously in the batch, mutatis mutandis. For some applications, the number of bars 22 (i.e. a maximum batch size) is a multiple of 3, e.g., such that all of the leaflets being tested in a single batch may be designated to leaflet groups of 3 matching leaflets, each group being used in a respective tri-leaflet prosthetic valve.

Typically, and as shown, platform 48 has an upper surface 50, the upper surface including a guide 52 that defines a guide-outline 54 corresponding to a leaflet-outline 56 of leaflet 30. In some applications, upper surface 50 at guide 52 may comprise a low-friction material. For example, the low-friction material may comprise polytetrafluoroethylene (e.g., Teflon™). Alternatively or additionally, the texture of upper surface 50 may be modified at guide 52. For example, the texture of upper surface 50 may be made to be more smooth (e.g., polished) at guide 52. The use of low-friction material and/or texture for upper surface 50 of guide 52 is hypothesized by the inventors to facilitate release of leaflet 30 from the surface as bar 22 lifts the leaflet away from the surface, thereby facilitating use of tester 20.

Figure 5B:
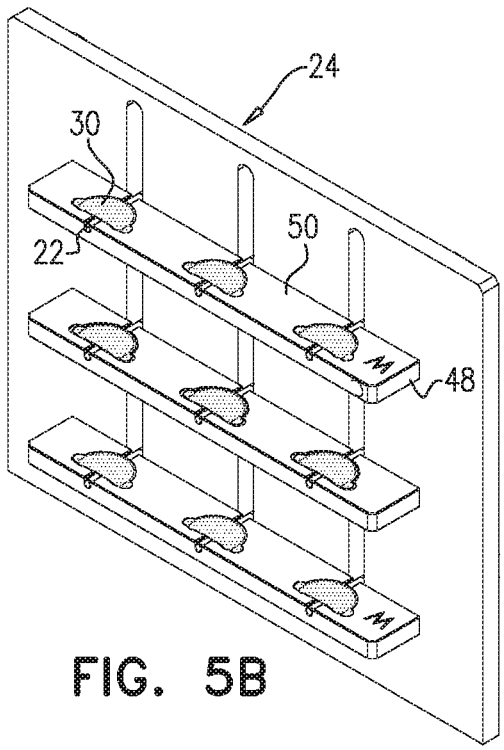
FIGS. 5A-C are schematic illustrations showing the arrangement of platforms with respect to bars and a mount, showing lifting of bars such that each bar supports a leaflet, with the leaflet draped over the bar, in accordance with some applications of the invention.
Figure 5A:
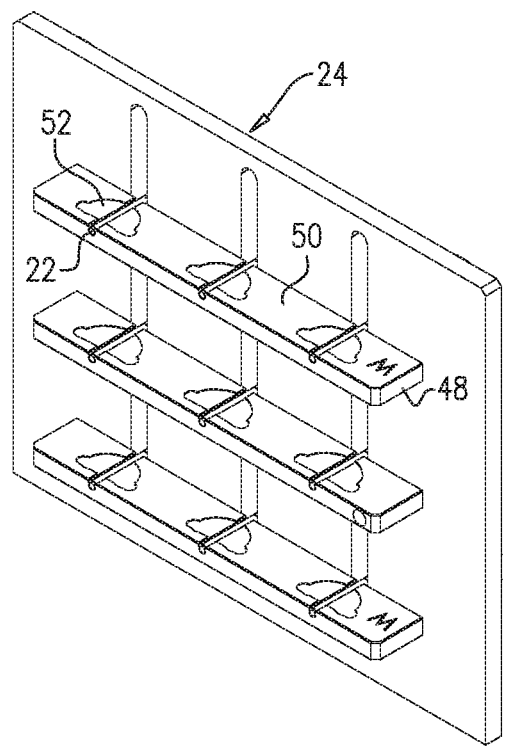
Figure 5C:
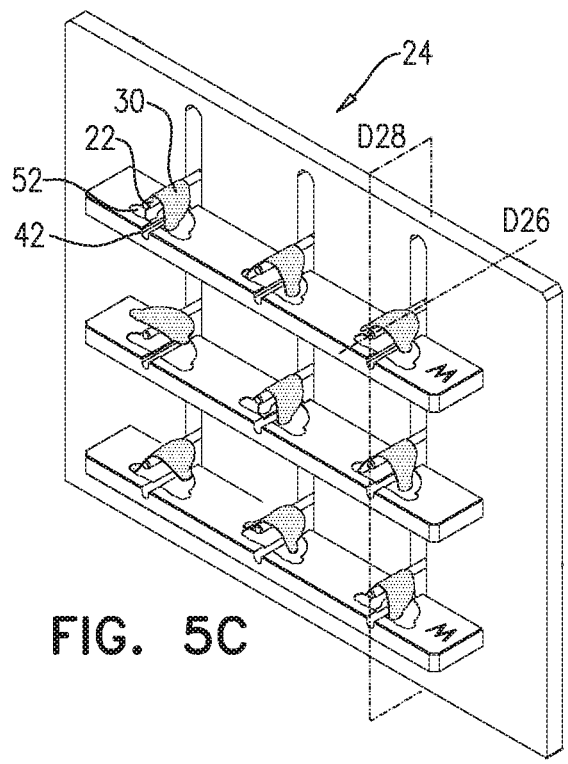

Reference is further made to FIGS. 5A-5C, which are schematic illustrations showing lifting of bars 22 such that each bar supports leaflet 30, with the leaflet draped over the bar, in accordance with some applications of the invention. Typically, and as shown, bar 22 has an initial position (FIG. 5A) with respect to platform 48, in which leaflet 30 may be placeable across the bar such that the leaflet is in contact with upper surface 50, and surface 50 supports the leaflet, e.g., in a flat configuration (FIG. 5B). For example, in the initial position, bar 22 may be disposed below upper surface 50.

For some applications, leaflets 30 are non-isotropically flexible. For example, a leaflet may have a first flexibility when draped over bar 22 with a first side of the leaflet facing up, and a different flexibility when draped over the bar with the opposite side of the leaflet facing up. For such applications, leaflets 30 are typically draped over bars 22 such that they bend in the orientation in which they will bend when in use. Typically, the side of the leaflet that faces up on tester 20 is the side of the leaflet that will face upstream in the functioning prosthetic valve.

For example, leaflets 30 may comprise pericardium that has distinct sides (e.g., a rough side (e.g., a fibrous side) and a smooth side (e.g., a parietal side)). For such applications, the rough side typically faces upstream in the functioning prosthetic valve. Therefore, for such applications, it may be desirable to orient leaflets 30 upon respective guides 52 with the rough side facing upwards, such that, upon actuation of actuator, each leaflet will drape over respective bar 22 with the rough side facing upwards.

Alternatively, it may be desirable to orient leaflets 30 upon respective guides 52 with the smooth side facing upwards, such that, upon actuation of actuator, each leaflet will drape over respective bar 22 with the smooth side facing upwards. It is hypothesized by the inventors that uniform orientation of leaflets 30 upon guide 52 may increase the relevance of leaflet flexibility testing to the performance of the leaflets in the prosthetic valve.

Typically, platform 48 is disposed with respect to bar 22 such that bar-plane D28 bisects guide-outline 54 (FIG. 4B-C). Further typically, and as shown, platform 48 is disposed with respect to bar 22 such that bar-plane D28 bisects guide-outline 54 symmetrically. As shown in FIG. 5C, in the elevated state of tester 20, each bar 22 supports the respective leaflet 30 along the respective bar-axis D26 such that the leaflet drapes over the bar.

For some applications, mount 24 may have a strong color. For some applications, bar-tip 68 may have a second strong color. For some applications, platform 48 may have a third strong color. For example, a platform face 36 of platform 48 may have the third strong color. It is to be noted that the term "strong color" (including the specification and the claims) relates to color saturation. For example, primary colors may serve as the strong colors. The use of respective strong colors for mount 24, bar-tip 68 and/or platform face 36 is hypothesized to facilitate analysis of the image by facilitating distinction between these components and leaflet 30, and between these components and each other.

Figure 6B:
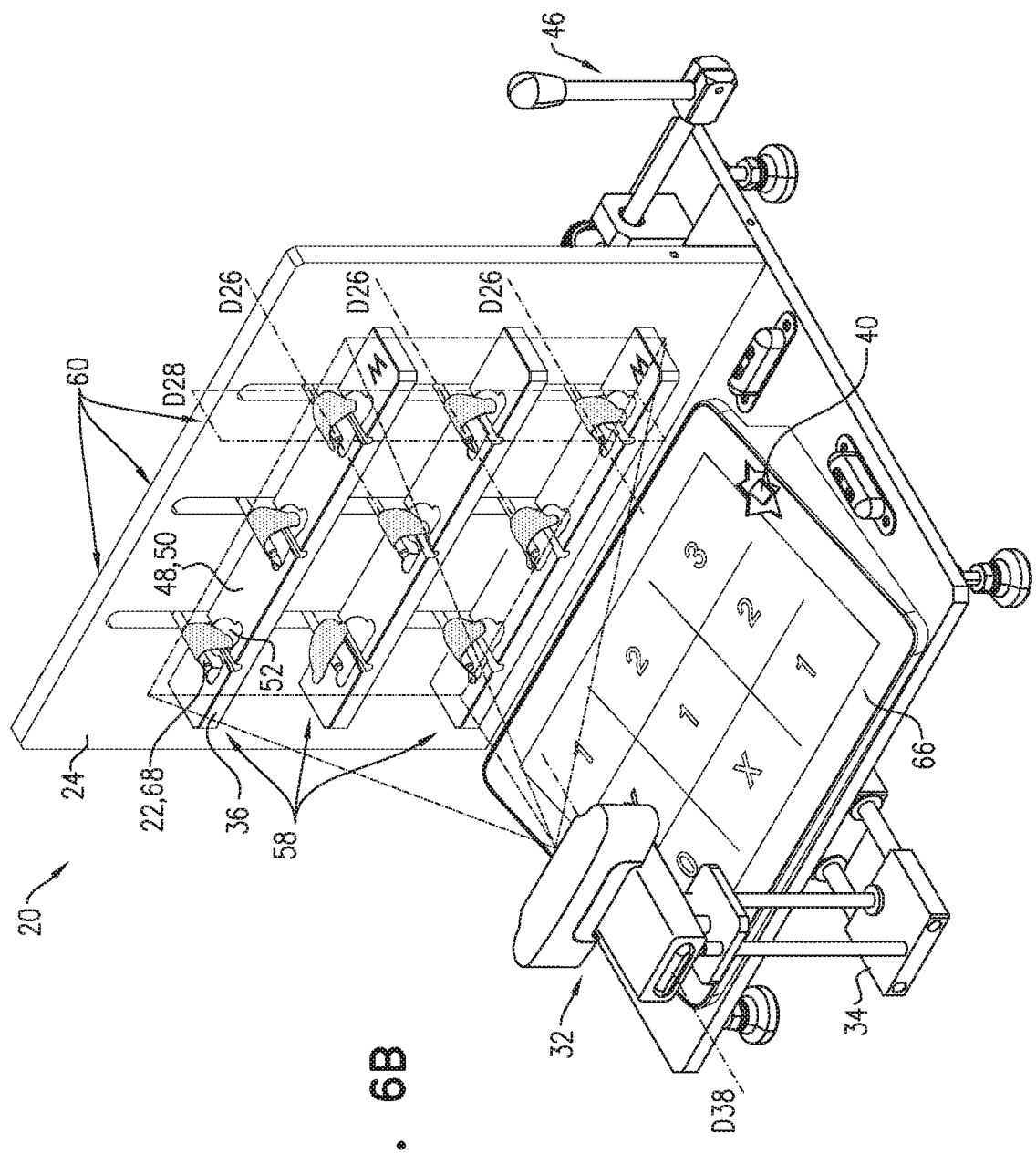
Figure 6C:
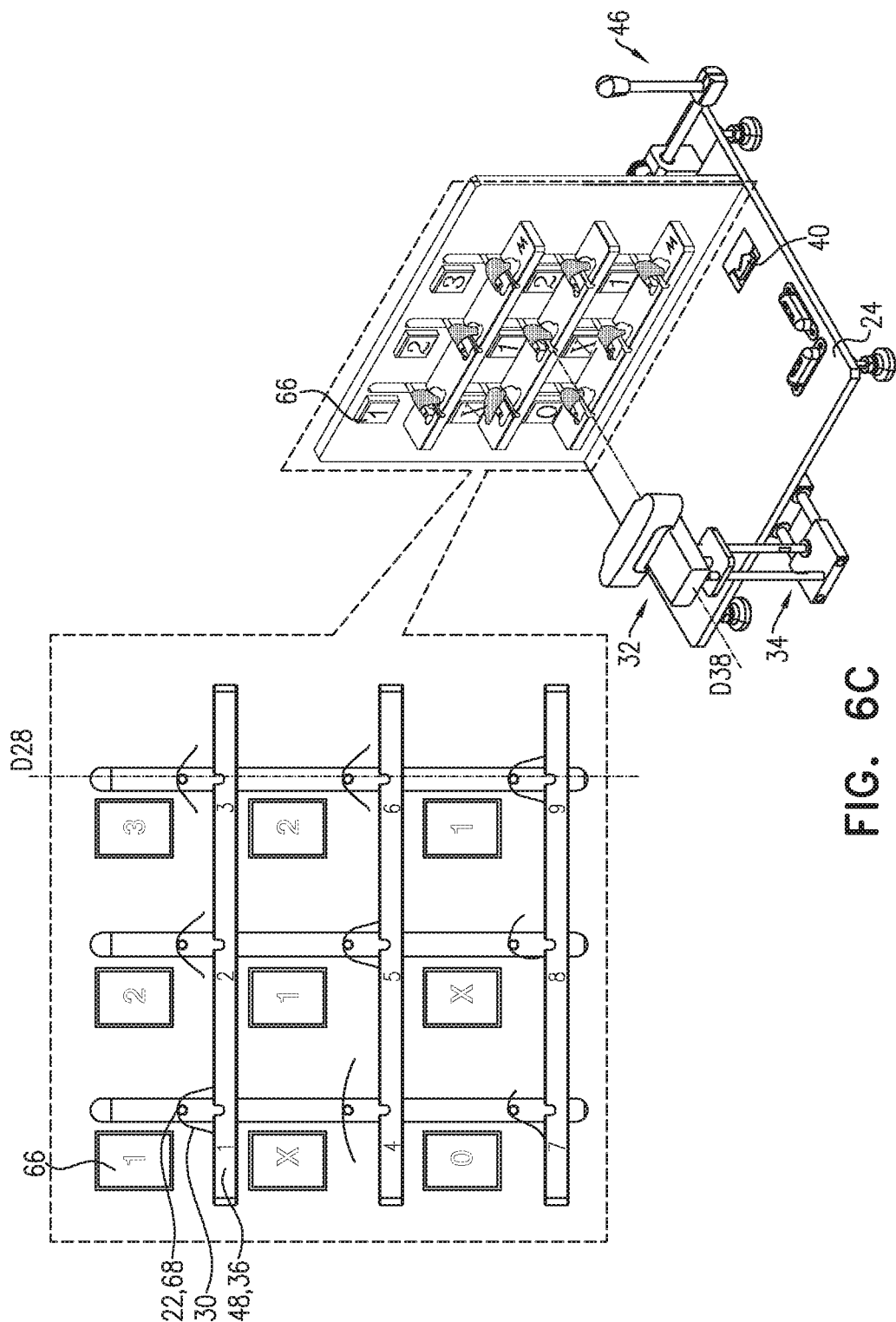

Reference is made to FIGS. 6A-C, which are schematic illustrations showing use of tester 20, in accordance with some applications of the invention.

As described hereinabove, image sensor 32 acquires an image that includes the plurality of leaflets 30 draped over their respective bars.

In some applications (e.g., those shown in FIGS. 6B-C), circuitry 40, configured to receive the image, is coupled to (e.g., mounted on) tester 20. Typically, circuitry 40 is further configured to analyze the image, such that, for each leaflet 30 included in the image, the circuitry derives a corresponding leaflet-flexibility value that is indicative of flexibility of the leaflet. Derivation of the leaflet-flexibility value is described in more detail hereinbelow.

For some applications, circuitry 40 is not mounted on tester 20. For such embodiments, tester 20 may include an image output device (e.g., a port or wireless transceiver) 64 (FIG. 6A). Typically, output device 64 is configured to interface with a distinct computer 100 (e.g., a general-purpose computer), and therefore device 64 typically operates according to a recognized standard, such as USB or Bluetooth. For such applications, software is provided to be run on local or network-connected computer 100, and therefore the circuitry of the computer serves as circuitry 40.

For some applications, and as described in more detail hereinbelow, circuitry 40 is further configured to assign a category to each of the leaflets, in response to the leaflet-flexibility value. Typically, and as shown in FIGS. 6B-C, tester 20 includes at least one indicator 66 that is in communication with circuitry 40, and indicates the respective category assigned to each leaflet 30. For some applications, tester 20 comprises a single indicator (e.g., a display) that indicates the categories of all of the leaflets (e.g., as shown in FIG. 6B). For other applications, tester 20 comprises a respective indicator 66 for each leaflet 30, the indicator configured to indicate the category assigned to the leaflet. For example, indicator 66 may be disposed adjacent to the respective bar 22 that supports the respective leaflet 30 (e.g., as shown in FIG. 6C). For applications in which a distinct computer receives the image and derives the value, the computer (e.g., a display of the computer) also serves as the indicator that indicates the categories (e.g., as shown in FIG. 6A).

For some applications, circuitry 40 is pre-programmed with a calibration routine, such that all leaflets 30 included in the image acquired by sensor 32 are correctly analyzed, e.g., despite each leaflet being disposed at a different position with respect to the image sensor. For some applications, the calibration routine includes acquiring an image that includes one or more (e.g., all) bar-tips 68, and analyzing the image in order to determine a position of sensor 32 with respect to the plurality of bars. For some such applications, the calibration routine is performed automatically, e.g., using the same image that includes the plurality of leaflets, which will be analyzed by circuitry 40 to derive the respective leaflet-flexibility values, as described hereinbelow. Alternatively, the calibration routine may be done separately from (e.g., prior to) placing leaflets over bars 22 of tester 20.

For some applications, sensor-bracket 34 comprises an electronic actuator, with which circuitry 40 may interface in order to move image sensor 32 (e.g., along sensor-axis D38). For some such applications, this movement is used to facilitate the calibration routine. The calibration of image sensor 32 may adjust a field of view of image sensor 32 such that the image sensor acquires an image that includes all leaflets 30.

Reference is made to FIGS. 7A-C, 8A-B and 9A-B, which are schematic illustrations showing image parameters that may be calculated by circuitry 40 in order to derive a leaflet-flexibility value, in accordance with some applications of the invention. Circuitry 40 typically derives leaflet-flexibility values for leaflets 30 by digitally analyzing the image acquired by sensor 32. Circuitry 40 may derive the leaflet-flexibility values in response to a single image parameter, or a combination of image parameters, e.g., as described hereinbelow.

FIG. 7A shows a leaflet 30a that has high flexibility. FIG. 7B shows a leaflet 30b that has moderate flexibility. FIG. 7C shows a leaflet 30c that has low flexibility.

As described hereinabove, bars 22 are configured to support leaflet 30 along bar-axis D26 such that the leaflet drapes over the bar. As shown, a first-leaflet-tip 70 is disposed below the bar on a first side 72 of the bar, and a second-leaflet-tip 74 is disposed below the bar on a second side 76 of the bar. For example, first-leaflet-tip 70 may be a lowest part of leaflet 30 on first side 72, and second-leaflet-tip 74 may be a lowest part of leaflet 30 on second side 76. In some applications, circuitry 40 is configured to identify, in the acquired image, first-leaflet-tip 70 and second-leaflet tip 74, and to derive the leaflet-flexibility value at least in part responsively to a first-leaflet-tip position D96 of first leaflet tip 70 and a second-leaflet-tip position D98 of second leaflet tip 74.

Image parameters that are calculated by circuitry 40 to derive leaflet-flexibility values may include one or more of the following:

(i) A direct distance D82 between first-leaflet-tip position D96 and second-leaflet-tip position D98. It is to be noted that the term "direct distance" (including the specification and the claims) means the length of a shortest line between two positions (e.g. D82 between D96 and D98, D84 between D96 and bar-tip 68, or D86 between D98 and bar-tip 68).

(ii) An Area Under the Curve (AUC) D80 defined by a leaflet draping-contour line 78 and an AUC closure line D102.

(iii) An axial height D88 or D90 along a vertical axis between (a) first-leaflet-tip position D96 and/or second-leaflet-tip position D98, respectively, and (b) bar-tip 68.

(iv) An axial distance D92 or D94 along a horizontal axis between (a) first-leaflet-tip position D96 or second-leaflet-tip position D98, respectively, and (b) bar-tip 68.

(v) An axial distance D95 along a horizontal axis between first-leaflet-tip position D96 and second-leaflet-tip position D98. While D95 may be equal to the sum of D92 and D94, D95 is nonetheless typically derived independently of D92 and D94, in that D95 is independent of identifying the location of bar-tip 68. In some cases (e.g. for symmetrically draping leaflets), D95 may be equal to direct distance D82 between respective leaflet-tips.

(vi) A length of the leaflet draping-contour line 78 (a) between bar-tip 68 and first-leaflet-tip position 96, and (b) between bar-tip 68 and second-leaflet-tip 98.

The use of a plurality of image parameters to derive leaflet-flexibility values is hypothesized by the inventors to more accurately reflect leaflet flexibility than may be derived from a single parameter. For example, a low AUC may alternatively indicate either a highly flexible or highly inflexible leaflet. The integration of AUC with direct distance D82 between first-leaflet-tip position D96 and second-leaflet-tip position D98 may aid in deriving a leaflet-flexibility value that more accurately reflects the leaflet's flexibility.

In some applications, leaflet-flexibility values may be used to facilitate sorting of the leaflets into categories of leaflet flexibility. For example, high-flexibility leaflet 30a may be assigned by tester 20 (e.g., circuitry 40 thereof) to a flexibility category "1", moderate-flexibility leaflet 30b may be assigned to a flexibility category "2", and low-flexibility leaflet 30c may be assigned to a flexibility category "3"- and the operator may sort the leaflets according to the assigned categories. As described hereinabove, the category for each leaflet is typically indicated by indicator 66, e.g., as shown in FIGS. 6A-C.

Leaflets 30 may also be assigned to a "retest" category, or a "discard" category, e.g., as described hereinbelow. Typically, the process is a batch process, in which multiple leaflets are placed on tester 20, tested, and then sorted.

Leaflets that are assigned to the "retest" category may be resituated within the same or a different guide 52 for retesting (e.g., in the subsequent batch). Alternatively, leaflets 30 assigned to a "retest" category may be collected into a "retest" receptacle for subsequent retesting (e.g., in a dedicated retesting batch).

FIGS. 8A-B are schematic illustrations of unsuitable leaflets, in accordance with some applications of the invention. FIG. 8A schematically illustrates a leaflet 30d that is insufficiently flexible for use in a prosthetic heart valve. In response to the derived leaflet-flexibility value, circuitry 40 typically assigns the leaflet to an appropriate category (e.g., an "unsuitable" or "discard" category). This is represented in FIGS. 6A-C as category "x." For example, FIG. 12A shows category "x" spanning a range D162 of leaflet-flexibility values, range D162 being separated from range D144 of leaflet-flexibility values of category "3" by threshold D106. Leaflet-flexibility values within range D162 may characterize leaflets unsuitable for use in a prosthetic heart valve. Although FIGS. 6A-C depict unsuitable category "x" leaflets that are unsuitable for being overly inflexible, this depiction is not meant to exclude the possibility that excessively flexible leaflets may be assigned to an alternate category "y" of excessively flexible leaflets. For example, FIG. 12A shows category "y" spanning a range D164 of leaflet-flexibility values, range D164 being separated from range D148 of leaflet-flexibility values of category "1" by threshold D124. Leaflet-flexibility values within range D164 may characterize leaflets unsuitable for use in a prosthetic heart valve. Typically, unsuitable leaflets 30 assigned to either category "x" or "y" are discarded.

It is to be noted that, although leaflets 30 in FIGS. 7A-C and FIG. 8A drape symmetrically, the scope of the invention includes deriving leaflet-flexibility values and/or assigning categories for a leaflet that drapes asymmetrically, at least up to a certain degree of asymmetry. FIG. 8B shows a non-isotropically-flexible leaflet 30e that drapes asymmetrically as a result of its non-isotropic flexibility.

Circuitry 40 may be configured to categorize non-isotropically-flexible leaflets as described hereinabove, at least up to a threshold degree of asymmetric draping. For example, and as shown in FIG. 8B, non-isotropically-flexible leaflets may drape asymmetrically, such that direct distance D82 is not equal to horizontal distance D95. Circuitry 40 may therefore be used to identify non-isotropically-flexible leaflets by comparing direct distance D82 to horizontal distance D95. For some applications, for a leaflet whose draping asymmetry is greater than a threshold degree of asymmetry, circuitry 40 may assign the leaflet to an appropriate category (e.g., an "unsuitable" or "discard" category), such as category "x" described hereinabove.

For some applications, circuitry 40 identifies non-isotropic flexibility of a leaflet 30 by calculating a difference between axial distance D92 and axial distance D94. Alternatively or additionally, circuitry 40 may identify non-isotropic flexibility of a leaflet 30 by calculating a difference between axial distance D88 axial distance D90. It is hypothesized by the inventors that a difference between D92 and D94, and/or a difference between D88 and D90, will be greater for non-isotropically-flexible leaflets than for isotropically-flexible leaflets, thereby facilitating identification of non-isotropically-flexible leaflets.

As described hereinabove, circuitry 40 may be configured to detect asymmetric draping. In that case, the asymmetric draping is asymmetric draping that is caused by, and is indicative of, non-isotropic flexibility of the leaflet. Circuitry 40 may also be configured to detect asymmetric draping that is caused by, and is indicative of, improper positioning of the leaflet being tested, e.g., caused by the operator improperly positioning the leaflet, and/or by slippage of the leaflet during elevation of the bar. In response to detection of such improper positioning, circuitry 40 typically assigns the leaflet to a "retest" category.

An exemplary reason for a leaflet to be assigned to the "retest" category is measurement error. In this context, the term "measurement error" is used to refer to situations in which image parameters and/or leaflet-flexibility values may not enable circuitry 40 to accurately assign leaflet 30 to a leaflet flexibility category. In such cases, indicator 66 may indicate a need to repeat the measurement and/or to adjust leaflet flexibility measurement conditions. For example, FIGS. 9A-B show two types of measurement error, in which leaflets 30 may be assigned to the "retest" category that indicates a need to retest the leaflets. This is represented by a "0" in FIGS. 6A-C.

FIG. 9A shows measurement error introduced by sub-optimal positioning of leaflet 30 on bar 22. Another potential source of measurement error may be adherence of leaflet 30 to guide 52, shown in FIG. 9B, which may cause slippage of the leaflet over the bar during elevation of the bar. FIG. 9B shows an adhesion site 101 at which leaflet 30 had adhered to platform 48 (e.g., guide 52 thereof), such that when bar 22 was elevated, the leaflet was pulled off of the bar to one side. As described hereinabove regarding asymmetrically draping leaflets, mutatis mutandis, comparison of horizontal distance D95 with direct distance D82 may also be used to indicate measurement error. Measurement error may alternatively or additionally be identified in response to a difference between (i) a direct distance D84 between first-leaflet-tip position D96 and bar-tip 68, and (ii) a direct distance D86 between second-leaflet-tip position D98 and the bar-tip. It is hypothesized by the inventors that the difference between direct distances D84 and D86 may be greater when leaflet 30 is improperly positioned and/or has slipped. It is further hypothesized by the inventors that the difference between direct distances D84 and D86 is more strongly correlated with measurement error than with non-isotropic flexibility of a leaflet, facilitating discrimination between measurement error and proper measurement of leaflet flexibility.

For some applications, measurement error is identified in response to a difference between vertical axial distance d88 and vertical axial distance d90. For some applications, measurement error is identified in response to a difference between horizontal axial distance d92 and horizontal axial distance d94.

For some applications, circuitry 40 may detect instances of measurement error in response to a plurality of image parameters to, e.g., by cross-validation of image parameters. For example, circuitry 40 may compare a difference between D88 and D90, to a difference between D92 and D94. Alternatively or additionally, circuitry 40 may compare a difference between D88 and D92, to a difference between D90 and D94. In addition to one or both of these comparisons, circuitry 40 may also take into account direct distances D84 and D86. It is hypothesized by the inventors that the derivation of leaflet-flexibility values in response to more than one image parameter advantageously facilitates identifying measurement errors, e.g., distinguishing between (i) asymmetric draping caused by measurement error, and (ii) asymmetric draping caused by non-isotropic flexibility.

The use of a plurality of image parameters to derive leaflet-flexibility values is therefore hypothesized by the inventors to increase the validity and clinical utility of the flexibility categories to which leaflets 30 are assigned.

Figure 10:
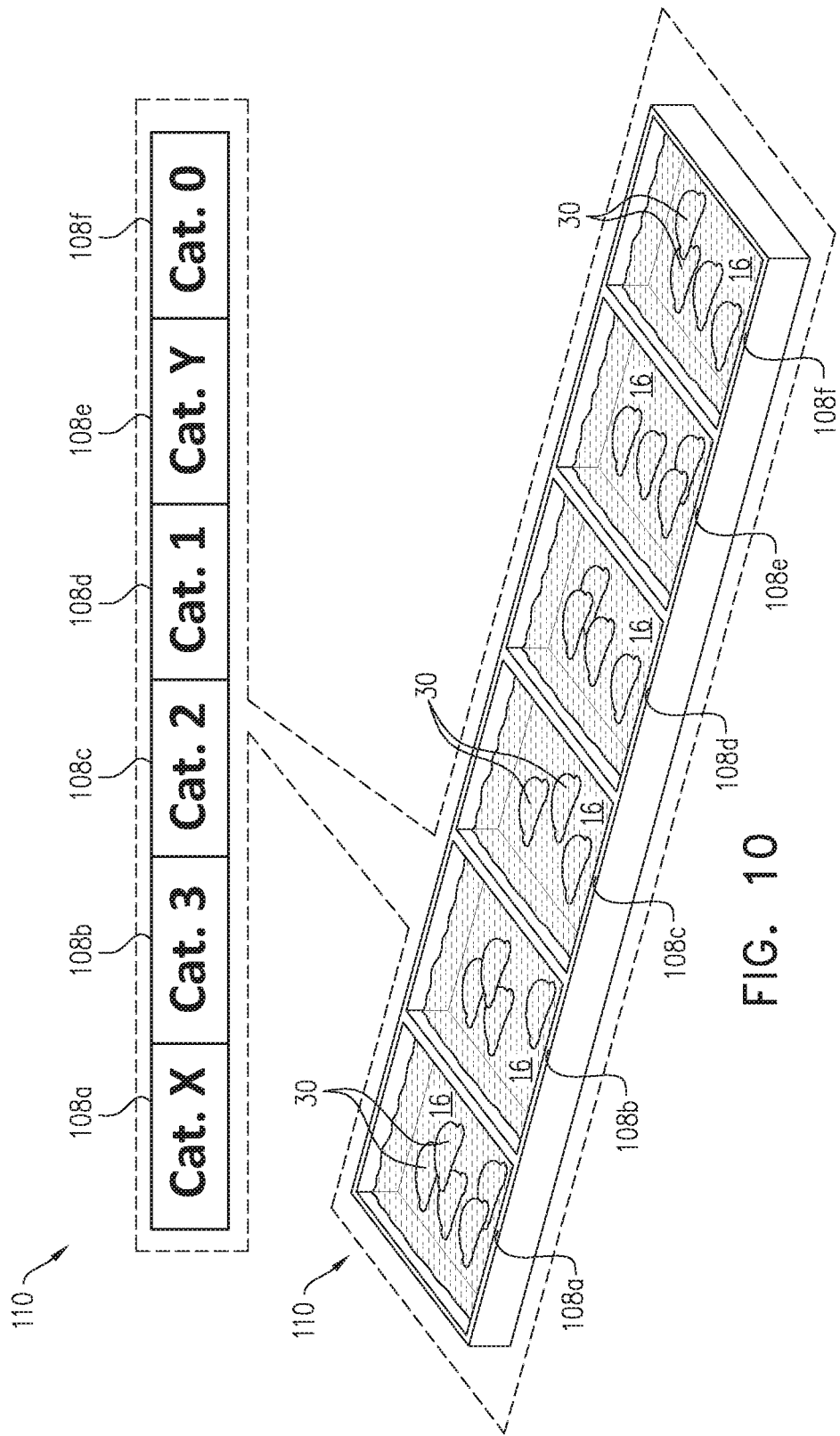
FIG. 10 is a schematic illustration showing a leaflet storage unit comprising a plurality of chambers, in accordance with some applications of the invention.

Reference is also made to FIG. 10, which is a schematic illustration showing a leaflet storage unit 110 comprising a plurality of chambers 108, in accordance with some applications of the invention. For some applications, leaflets 30 are sorted, according to the assigned leaflet-flexibility category, into storage unit 110. In this way, multiple batches of leaflets 30, each batch of leaflets comprising a plurality of leaflets, are typically positioned opposite image sensor 32. Digital images of respective batches of leaflets are acquired, and a leaflet-flexibility value of each leaflet is derived by digital analysis of each image. Leaflets of multiple batches may thereby be sorted, according to leaflet-flexibility category, into storage unit 110. That is, each chamber 108 may contain multiple leaflets 30, having originated from different batches, of the same leaflet flexibility category. Typically, for such applications, for subsequent manufacturing of a prosthetic heart valve, a group of leaflets 30 is subsequently selected from a given chamber 108, the number of leaflets in the group being determined by the number of leaflets required for the prosthetic heart valve.

Typically, storage unit 110 facilitates storing leaflets 30 while maintaining: (i) moisture content of the leaflets, (ii) sterility of the leaflets, and/or (iii) separation of leaflets assigned to different leaflet-flexibility categories. In the example shown, storage unit 110 is divided into five chambers 108, of which chambers 108b, 108c, 108d are respectively dedicated to store leaflets assigned to one of the leaflet-flexibility categories described herein above (e.g. "3", "2", "1"). Chambers 108a and 108e are dedicated to leaflets assigned to discard categories "x" and "y", respectively. Chamber 108f is dedicated to a "retest" category, which in this particular example is named "0". Periodically, any leaflets present in chamber 108f may be retested, e.g., when a sufficient number of leaflets are present in the chamber.

Reference is also made to FIG. 11, which is a schematic illustration showing use of tester 20 to designate leaflets 30 to leaflet groups according to leaflet-flexibility values of the leaflets, in accordance with some applications of the invention.

FIG. 11 shows leaflets 30 draped over bars 22, and indicators 66 indicating a leaflet group designation of leaflets into leaflet groups "A", "B" and "C", according to similarity of their respective leaflet-flexibility values. In the example shown, the simultaneous testing of nine leaflets, and the grouping of nine leaflets into three leaflet groups, may enable the construction of three trileaflet prosthetic heart valves, from each testing session. In the example shown, one trileaflet valve would be constructed from the three leaflets in group A, one trileaflet valve from those in group B, and one trileaflet valve from those in group C. It is hypothesized by the inventors that grouping leaflets 30 with similar leaflet-flexibility values (e.g., to be sewn together in a prosthetic heart valve) may facilitate the preparation of properly functioning prosthetic heart valves.

Reference is also made to FIGS. 12A-B, which are graphs representing a relationship between leaflet-flexibility values of a set of leaflets 30, and the leaflet-flexibility categories or leaflet groups to which the same leaflets are assigned, in accordance with some applications of the invention. As described hereinabove, for some applications leaflets 30 are assigned to leaflet-flexibility categories, based upon leaflet-flexibility values. Leaflet-flexibility categories are typically categorical variables. For example, the categories may be named categories "1", "2" and "3", e.g., as described hereinabove. Leaflet-flexibility values are typically continuous numerical variables. For example, leaflet-flexibility values may span a range from 10 to 40, as shown.

Typically, and as shown, each leaflet flexibility category is defined by threshold leaflet-flexibility values, each threshold leaflet-flexibility value lying at a respective extreme of the category, such that each category includes leaflets with values spanning a range between the upper and lower thresholds of the category. In this way, each leaflet flexibility category spans a range of leaflet-flexibility values, each flexibility category having an upper flexibility-value threshold and a lower flexibility-value threshold. Thus, a given leaflet-flexibility value typically fits within the range defined by the upper flexibility-value threshold and the lower flexibility-value threshold of one of the leaflet-flexibility categories. For example, FIG. 12A shows category 1 spanning a range D148 of leaflet-flexibility values, category 2 spanning a range D146 of leaflet-flexibility values, and category 3 spanning a range D144 of leaflet-flexibility values. Solid vertical lines represent the thresholds dividing between the leaflet-flexibility categories.

For some applications, the same threshold may serve as an upper flexibility-value threshold for a first category, and as a lower flexibility-value threshold for a second category. For example, category "3" spans a range of leaflet-flexibility values between threshold D106 and threshold D112 ranging between 10 and 20, category "2" spans a range of leaflet-flexibility values between threshold D112 and threshold D118 ranging between 20 and 30, and category "1" spans a range of leaflet-flexibility values between threshold D118 and threshold D124 ranging between 30 and 40. In this way, threshold D112 serves as the upper leaflet-flexibility value of category "3", and serves as the lower leaflet-flexibility value of category "2". Similarly, threshold D118 serves as the upper leaflet-flexibility value of category "2", and serves as the lower leaflet-flexibility value of category "1".

It is to be noted that the leaflet-flexibility values and leaflet-flexibility category thresholds shown in FIGS. 12A-B are for illustrative purposes only. The values, ranges, and thresholds are arbitrary, and are not intended to exclude alternate leaflet-flexibility values, ranges, or thresholds.

In FIGS. 12A-B, hollow circles 138, 140 and 142 represent three leaflets that would be assigned to leaflet-flexibility category 1, having leaflet-flexibility values spanning a range from 30 to 40; hollow circles 132, 134 and 136 represent three leaflets that would be assigned to leaflet-flexibility category 2, having leaflet-flexibility values spanning a range from 20 to 30; and hollow circles 126, 128 and 130 represent three leaflets that would be assigned to leaflet-flexibility category 3, having leaflet-flexibility values spanning a range from 10 to 20.

It is hypothesized by the inventors that assigning leaflets 30 to flexibility categories may enable efficient sorting of leaflets by their leaflet-flexibility values. However, for some applications, sorting leaflets purely by such a categorization technique may result in leaflets that do not necessarily have the most similar leaflet-flexibility values, being sorted into the same category. For instance, FIG. 12A shows the leaflet-flexibility value of leaflet 130 (which would be categorized into category "3") to be closest to that of leaflets 132 and 134 (which would be categorized into category "2"). This potential obscuring of the similarity between leaflets in different categories due to their similar leaflet-flexibility values being on different sides of a category threshold value is referred to herein as "threshold artifact." Alternative or complimentary strategies to account for threshold artifact when assigning leaflets to flexibility categories, are described below.

For some applications, flexibility-value thresholds (e.g. the upper flexibility-value threshold and/or the lower flexibility-value threshold) may be adjusted responsively to leaflet-flexibility values of a plurality of leaflets. For example, the flexibility-value thresholds may be adjusted by circuitry 40 (e.g., automatically) before the leaflet-flexibility category of each leaflet is indicated. Alternatively, the flexibility-value thresholds may be manually adjusted by the operator. It is hypothesized by the inventors that adjusting flexibility-value thresholds may increase the likelihood of assigning leaflets 30 of similar flexibility to each respective leaflet flexibility category.

For some applications, circuitry 40 is configured to refer certain leaflets 30 for manual assignment (e.g., by a human specialist) to flexibility categories. For some applications, circuitry 40 may designate leaflets 30 with leaflet-flexibility values that are particularly close to the threshold values, to transition categories. For example, circuitry 40 may be configured such that each threshold has a margin, and leaflets whose leaflet-flexibility values fall within a margin of a threshold are assigned to a transition category. FIG. 12A further shows dotted vertical margin lines demarcating margins of respective thresholds: D108 demarcates an upper margin 150 of threshold D106, D110 demarcates a lower margin of threshold D112, D114 demarcates an upper margin 154 of threshold D106, D116 demarcates a lower margin of threshold D118, D120 demarcates an upper margin of threshold D118, and D122 demarcates a lower margin of threshold D124. For example, in FIG. 12A the leaflets represented by symbols 130, 132, and 134 fall within such margins, and are therefore designated to transition categories. Leaflets designated to transition categories, referred to as "transition category leaflets" (e.g., category "1-2", category "2-3", or category "3-x"), may then be referred to a person (e.g., a specialist) in order to be assigned manually to a flexibility category.

For some applications, and as shown, circuitry 40 is not configured with a lower margin for threshold D106 and/or an upper margin of threshold D124. For some such applications, leaflets whose leaflet-flexibility value falls below threshold D106 or above threshold D124 are referred to a person in order to be manually assessed (e.g., to be manually assigned to a flexibility category). For some such applications, such leaflets are automatically assigned to the corresponding "discard" category "x" or "y", e.g., to increase efficiency by reducing the likelihood of an unsuitable leaflet being referred to a specialist for manual categorization. For some such applications, leaflets whose leaflet-flexibility value falls below threshold D106 are referred to a person in order to be manually assessed, whereas leaflets whose leaflet-flexibility value falls above threshold D124 are automatically assigned to the corresponding "discard" category. For some such applications, leaflets whose leaflet-flexibility value falls above threshold D124 are referred to a person in order to be manually assessed, whereas leaflets whose leaflet-flexibility value falls below threshold D106 are automatically assigned to the corresponding "discard" category.

Alternatively, circuitry 40 is configured with a lower margin for threshold D106 and/or an upper margin of threshold D124, e.g., similarly to the margins of the other thresholds.

For some applications, tester 20 may simply indicate that a particular leaflet requires manual categorization. For some applications, tester 20 may facilitate manual categorization by indicating the categories between which the leaflet's leaflet-flexibility value falls. For example, indicator 66 of tester 20 may display "2-3" for a leaflet whose leaflet-flexibility value falls within margin 152 of the lower threshold of category 2 or within margin 154 of the upper threshold of category 3.

For some applications, transition category leaflets may be designated to be tested a second time. It is hypothesized by the inventors that: 1) manual assignment of transition category leaflets to flexibility categories, and/or 2) retesting of transition category leaflets, may increase the validity and clinical utility of leaflet flexibility categories to which leaflets 30 are assigned.

For some applications, leaflets may be designated to leaflet groups by circuitry 40 and/or by operator according to similarity of leaflet-flexibility values, e.g., without the use of flexibility categories. Leaflets 30 of the same group may then be included together in an individual prosthetic heart valve. Circuitry 40 may therefore group leaflets 30 into leaflet groups of a desirable size (e.g., leaflet groups of two leaflets for a bileaflet valve, or leaflet groups of three leaflets for a trileaflet valve). For example, in FIG. 12B, ovals 166 and 168 indicate such grouping.

That is, for some applications of the invention, tester 20 (e.g., circuitry 40 thereof) is configured to designate leaflets 30 (e.g., all of the leaflets that are on tester 20) into leaflet groups, based on similarity between (i) the leaflet-flexibility value of each leaflet of the plurality of leaflets, and (ii) the leaflet-flexibility value of other leaflets of the plurality of leaflets, each of the leaflet groups including a predetermined number of leaflets. For some such applications, the predetermined number of leaflets is received (e.g. as an input from the operator), using circuitry 40.

Oval 168 indicates a group of three leaflets (138, 140 and 142), which would all have been assigned to the same category (category 1) had the categorization technique had been used (e.g., as shown in FIG. 12A). In this case, grouping these three leaflets 30 according to similarity of their respective leaflet-flexibility values would yield a similar result to that of sorting the leaflets into leaflet-flexibility categories.

In contrast, oval 166 indicates a group of three leaflets (130, 132 and 134), in which two of the leaflets (132 and 134) would have been assigned to one category (category 2), and one of the leaflets (130) would have been assigned to a different category (category 3), had the categorization technique been used (e.g., as shown in FIG. 12A). Grouping these three leaflets 30 to be included together in an individual prosthetic heart valve would yield a prosthetic heart valve with leaflets having more similar leaflet-flexibility values than would a prosthetic heart valve with leaflets sorted into category 3 or into category 2.

Reference is made to FIGS. 13A-B and 14A-B, which are schematic illustrations showing use of leaflet storage arrays 104 and 204, to indicate individual leaflets as being designated to a particular leaflet group, in accordance with some applications of the invention. For some applications, it may be desirable to track individual identities of leaflets belonging to different batches, e.g., so that multiple batches of leaflets may be tested before the leaflets are designated into leaflet groups. It is hypothesized by the inventors that analyzing a larger number of leaflets before leaflet group designation may advantageously increase homogeneity between leaflets within a given group. FIGS. 13A-B and 14A-B show respective storage arrays 104 and 204 being used for storage of leaflets 30 in a manner that facilitates tracking of (i.e., keeping track of) individual identities of the leaflets. In the examples shown, arrays 104 and 204 are grids. However, it is to be understood that the scope of the invention includes arrays of various arrangements. As shown, each array 104 and 204 comprises, respectively, a plurality of storage cells 106 or 206, each cell typically configured to store an individual leaflet 30 (i.e., exactly one leaflet).

Typically, the array is labelled to provide each of its cells with a unique identifier. Array 104 of FIGS. 13A-B uses a particular labelling regime, and array 204 is typically identical to array 104, except that it uses a different labelling regime.

Array 104 has rows 112 of cells 106 labelled with letters, typically corresponding to different batches of tested leaflets 30. (A first row 112a and a second row 112b are labelled.) Within each row, cells 1-9 correspond to the nine individual leaflets 30 of the particular batch, the number signifying the bar over which each leaflet was draped during testing (e.g., according to labels 18 in FIG. 3B). In this illustrative example, nine batches, each batch consisting of nine leaflets 30, may be stored in individual cells 106 of array 104.

The example labelling regime of array 204 is such that each batch of leaflets is stored in a zone 214 having a number of cells 206 equal to a number of leaflets in the batch. (A first zone 214a and a second zone 214b are labelled.) Each cell of a given zone is labelled with (i) a letter that corresponds to a batch of leaflets, and (ii) a number that corresponds to the individual leaflets of that batch—e.g., signifying the bar over which each leaflet was draped during testing (e.g., according to labels 18 in FIG. 3B). As shown, the arrangement of cells 206 within a zone 214 typically corresponds to the arrangement of bars 22 of tester 20. It is hypothesized by the inventors that labelling cells 206 of storage array 204 in such a manner facilitates manual transfer of each leaflet from the tester to the storage array.

It is to be noted that the scope of the invention is not limited to alphanumerical characters, but also includes alternate methods of tracking individual identities of leaflets 30 (e.g. non-alphanumerical characters, symbols, color-coding, etc.).

For some applications, each cell 106 or 206 may be fillable with a sterile liquid (e.g. isotonic saline 16). It is hypothesized by the inventors that storage of leaflets 30 (e.g. an aggregate comprising multiple batches of tested leaflets 30) within respective storage cells 106, 206 of array 104, 204, facilitates maintenance of moisture content of the leaflets and/or sterility of the leaflets.

After multiple batches of leaflets 30 have been placed in storage array 104, 204, the leaflets are typically designated into leaflet groups, and then grouped into the leaflet groups. For some such applications, circuitry 40 designates the aggregate of leaflets into leaflet groups based on similarity between the leaflet-flexibility values of the leaflets (e.g., as described hereinbelow with reference to FIGS. 16-22). For such applications, circuitry 40 typically also indicates, using one or more indicators, which leaflets should be grouped into which group. The one or more indicators are typically electronically coupled (e.g. by cable 124, 224) and/or wirelessly connectable to circuitry 40, and are further typically coupled to and/or mounted on the storage array.

For some applications, a leaflet group designation of each leaflet 30 of the aggregate of leaflets to a leaflet group, is indicated (e.g. to an operator), using at least one indicator 120, 220. For some such applications, indicator 120, 220 is configured to provide a visual cue. For example, and as shown in FIGS. 13A-B and 14A-B, indicators 120, 220 may selectively indicate individual leaflets as being designated to a particular leaflet group.

For some applications, a user-interface connected to circuitry 40 (e.g. computer 100 shown in FIG. 6A) facilitates the operator's use of indicator 120, 220. For example, the user-interface may allow the operator to switch the indicator between indicating the various leaflet groups—e.g., to switch from indicating the leaflets that are designated to a first leaflet group, to indicating the leaflets that are designated to a second leaflet group, etc.

FIGS. 13A and 14A show arrays 104, 204 and indicators 120, 220, while the indicators are not illuminated. FIGS. 13B and 14B show the same arrays and indicators while the indicators selectively indicate three cells (those cells labelled "A4", "E6" and "I8"), indicating that these cells contain leaflets 30 designated to a particular leaflet group (e.g. indicating respective cells from which to group designated leaflets into a designated leaflet group).

For some applications, indicator 120, 220 is an integral component of array 104, 204.

Alternatively, and as shown, the indicator may be a discrete device, and the storage array may be juxtaposed with the indicator (e.g., placed on the indicator) such that the visual cue is visible through the array (e.g. through a floor of the array). For example, array 104, 204 may be: (i) at least partially transparent to the visual cue, and (ii) dimensioned in a manner corresponding to the dimensions of indicator 120, 220 (e.g. the indicator defines a surface upon which the array may be placed). In this way, the operator may receive the visual cue from indicator 120, 220, through array 104, 204, and group leaflets 30 from respective cells 106, 206 without cross-referencing between the storage array and a separate display representing the leaflet group designations.

For some such applications, indicator 120, 220 and array (104, 204) are complimentarily dimensioned (e.g. defining a notch and a groove), in a manner that facilitates integration of the array with the indicator such that the array is in a proper orientation with respect to the indicator. That is, proper orientation of array 104, 204 with respect to indicator 120, 220 assures that the visual cue indicated with respect to each leaflet 30, is visible through cell 106, 206 containing that respective leaflet. It is hypothesized by the inventors that integrating indicators 120, 220 into array 104, 204 reduces a risk of human error when the operator groups leaflets 30 into leaflet groups. At the same time, separability of array 104, 204 from indicator 120, 220 may facilitate successive use of multiple storage arrays (e.g. indicating leaflet group designations of multiple aggregates of leaflets to leaflet groups) with a given indicator. For some applications, the storage arrays are disposable, while the indicator is reusable.

Alternatively or in addition to facilitating step 332 by indicating the leaflets that are designated to the various leaflet groups, indicator 120, 220 may facilitate step 322 by indicating a portion of storage array 104, 204 (e.g. a cell 106, 206) in which to temporarily store leaflet 30 after testing. For example, indicator 120, 220 may be used in conjunction with the unique identifier of each cell 106, 206 described hereinabove in reference to FIGS. 13A-B and 14A-B.

Reference is made to FIG. 15, which is a schematic illustration showing a process wherein leaflets 30 are sorted into categories, and subsequently designated into leaflet groups, in accordance with some applications of the invention.

For some applications, leaflets 30 are first assigned to categories, and are subsequently designated to leaflet groups. For such applications, (i) leaflets 30 are placed onto tester 20, tested according to the categorization technique, and sorted according to their categories—e.g., into collections, and (ii) subsequently, leaflets from a single category are re-placed onto tester 20 and retested according to the grouping technique. It is hypothesized by the inventors that the grouping of leaflets 30 assigned to the same leaflet flexibility category, according to their leaflet-flexibility values, may enable grouping of leaflets into leaflet groups of highly similar flexibility.

For some applications, leaflets assigned to a leaflet-flexibility category (e.g. a first categorized batch of categorized leaflets and a second categorized batch of categorized leaflets sorted into storage unit 110) undergo a second iteration of flexibility testing. In the second iteration of testing, the categorized leaflets are retested, in order to be designated to leaflet groups, as described hereinabove. In this way, assigning leaflets 30 to categories may serve as a preliminary screening of leaflets of an initial stock (see arrows in FIG. 15 representing categorized leaflets of leaflet-flexibility category 2 being designated to leaflet groups "A," "B" and "C"). It is hypothesized by the inventors that designating to groups leaflets that were previously categorized into the same leaflet-flexibility category, may increase the likelihood of identifying closely matched leaflets (leaflets having similar leaflet-flexibility values) that are preferably designated into the same group.

Figure 16:
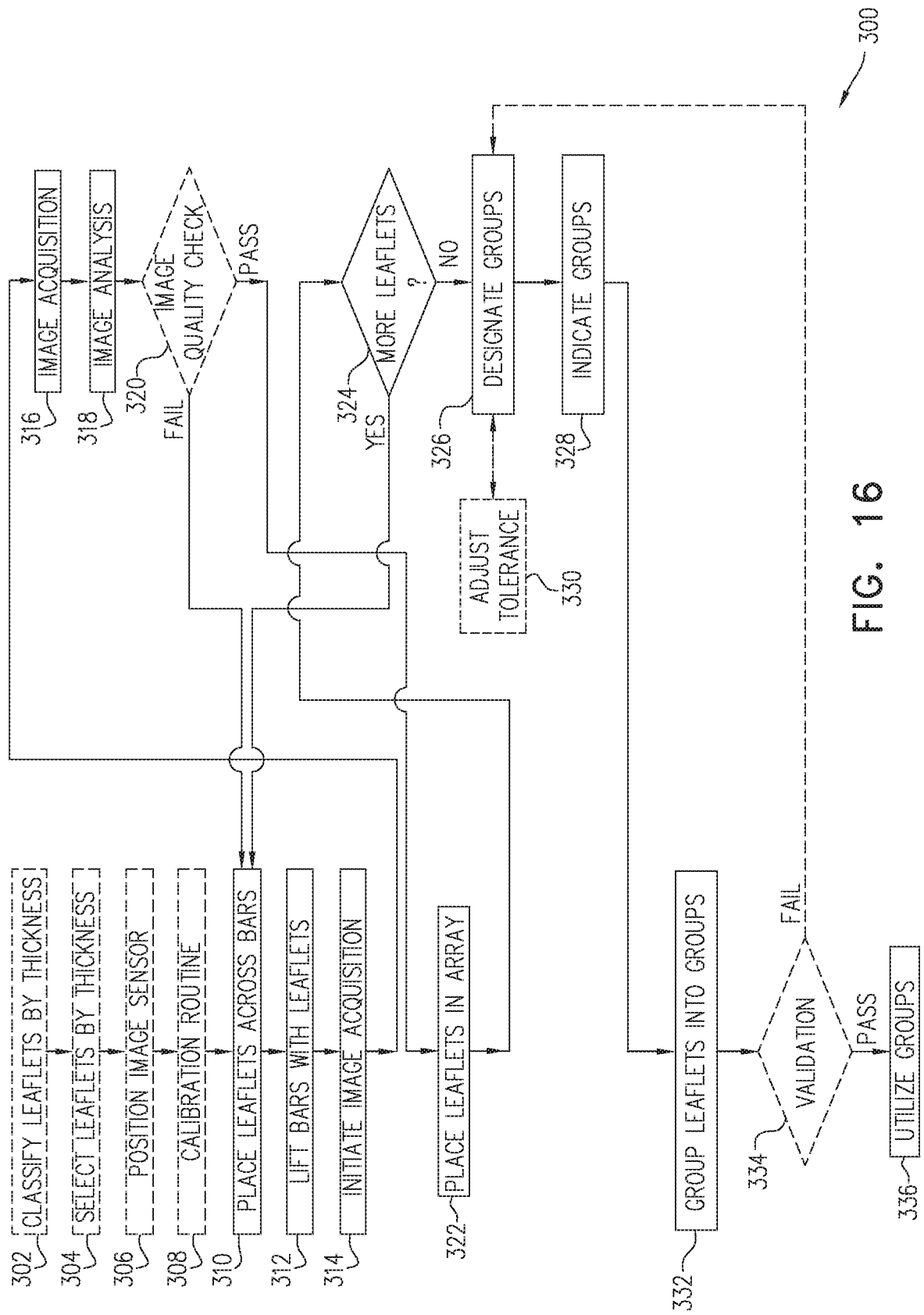
FIG. 16 is a flowchart that schematically illustrates at least some steps of a method for grouping the leaflets into leaflet groups, in accordance with some applications of the invention.

Reference is made to FIG. 16, which is a flowchart that schematically illustrates at least some steps of a method 300 for grouping leaflets 30 into leaflet groups, in accordance with some applications of the invention. Typically, method 300 is performed using tester 20 and/or techniques described hereinabove. For some applications, method 300 is performed using storage array 104, 204. The flowchart of FIG. 16 roughly indicates which steps of method 300 are performed by a human operator (left side of the flowchart) and which are performed by circuitry 40 (right side of the flowchart). However, it is to be understood that the scope of the invention includes certain steps that are indicated as being performed by the operator, being performed by the circuitry (or another component of tester 20), or vice versa, mutatis muandis. It is also to be noted that software may be provided (or made remotely accessible) that performs the steps described herein as being performed by circuitry 40.

In order to use tester 20, multiple leaflets 30 are draped over respective bars 22 of the tester (step 310). However, several optional steps may be performed beforehand (indicated by broken boxes).

In optional steps 302 and 304, leaflets of a stock of leaflets 30 are initially classified according to their thickness (step 302), and are then selected according to their thickness (step 304), such that the leaflets that will be tested using tester 20 are of a single thickness class. For such applications, the testing using tester 20 may represent a second, "fine" classification according to flexibility of leaflets 30, subsequent to an initial "coarse" classification according to their thickness. It is hypothesized by the inventors that performing flexibility testing on leaflets that have already been pre-classified to a single thickness may further improve the matching of leaflets for use in a prosthetic valve.

Alternatively or in addition to initially classifying leaflets 30 according to their thickness, method 300 may be performed using leaflets previously assigned to a leaflet-flexibility category, e.g., as described hereinabove in reference to FIG. 15, mutatis mutandis.

In optional step 306, image sensor 32 may be (re)positioned prior to testing leaflets 30 on tester 20 (e.g., as described hereinabove).

In optional step 308, circuitry 40 is activated to perform a dedicated calibration routine prior to placing leaflets over bars 22 of tester 20 (e.g., as described hereinabove). (For some applications, a calibration is alternatively or additionally performed as part of the subsequent image analysis of step 318.)

After leaflets 30 have been placed across bars 22 (step 310), the bars are lifted with respect to platform 48, such that leaflets 30 drape over the bars (step 312). The operator then initiates acquisition (step 314) of a digital image by image sensor 32 (step 316), the image including the multiple leaflets draped over bars 22.

Typically, at this stage, circuitry 40 performs analysis of the acquired image (step 318), the analysis typically comprising calculating one or more image parameters and deriving, for each leaflet 30, a leaflet-flexibility value, e.g., as described hereinabove.

For some applications, circuitry 40 performs an image-quality check routine (step 320), which may be part of image analysis (step 318), or may be a distinct step. For some such applications, the image-quality check routine is run prior to deriving the leaflet-flexibility value for each leaflet. For some applications, the image-quality check routine comprises calculating, for each leaflet, an image parameter. For example, the parameter derived in the image-quality check routine may be direct distance D82 between a first-leaflet-tip position and a second-leaflet-tip position (FIG. 8B). Alternatively or in addition, horizontal distance D95 may be derived as part of the image-quality check routine. It is hypothesized by the inventors that calculating horizontal distance D95 may facilitate identification of a sub-optimally positioned leaflet 30 (FIGS. 9A-9B), as described hereinabove. For example, a leaflet having a horizontal distance D95 below a predetermined threshold may be identified as being sub-optimally positioned.

For some applications, an image passes the image-quality check routine if the image parameter was successfully calculated for all of the leaflets in the image. Examples of why an image might fail the image-quality check routine include an unclear image, an obstacle obscuring one or more of the leaflets, improperly placed leaflets, failure of circuitry 40 to identify both leaflet-tips of a leaflet, and/or an unexpected or illogical image parameter value.

In the case that the image fails the image-quality check, leaflets 30 are placed again across bars 22 (e.g., placement of the leaflets is adjusted), the bars are re-lifted, and the image is re-acquired. In the case that the image passes the image-quality check, the plurality of leaflets 30 are typically stored in a manner that facilitates tracking of the individual identity of the leaflets, e.g., by placing the leaflets in storage array 104, 204 (step 322).

If additional batches of leaflets 30 are to be tested (step 324), steps 310-322 are repeated for the additional leaflets (e.g. until storage array 104, 204 is full, or until all the leaflets have been tested). Thus, an aggregate of leaflets comprising multiple batches of leaflets is assembled on the array. Typically for such applications, the aggregate comprises at least 9 and/or fewer than 400 leaflets, e.g., 9-400 leaflets (e.g., 9-100 leaflets or 40-400 leaflets), such as 40-100 leaflets. For example, and as shown, the aggregate may comprise eighty-one leaflets. For some applications, the entire aggregate of leaflets is tested before circuitry 40 designates the leaflets into leaflet groups. It is hypothesized by the inventors that testing flexibility of the aggregate of leaflets 30, before designating the batches of leaflets into leaflet groups, increases the likelihood of designating closely matched leaflets to each group.

Although method 300 is described hereinabove (and is shown in FIG. 16) as having image analysis step 318 performed for each batch of leaflets prior to placing the subsequent batch of leaflets across the bars of tester 20, for some applications the images (e.g. a first digital image and a second digital image) acquired during each step 316 are stored (e.g., in memory of circuitry 40), and analysis of multiple such images is performed subsequently to acquisition of all of the images of all of the batches of leaflets.

Typically, while the aggregate of leaflets 30 is stored in storage array 104 or 204, the leaflets are designated to respective leaflet groups (step 326), based on similarity between the respective leaflet-flexibility values of each leaflet of the aggregate of leaflets.

Figure 17:
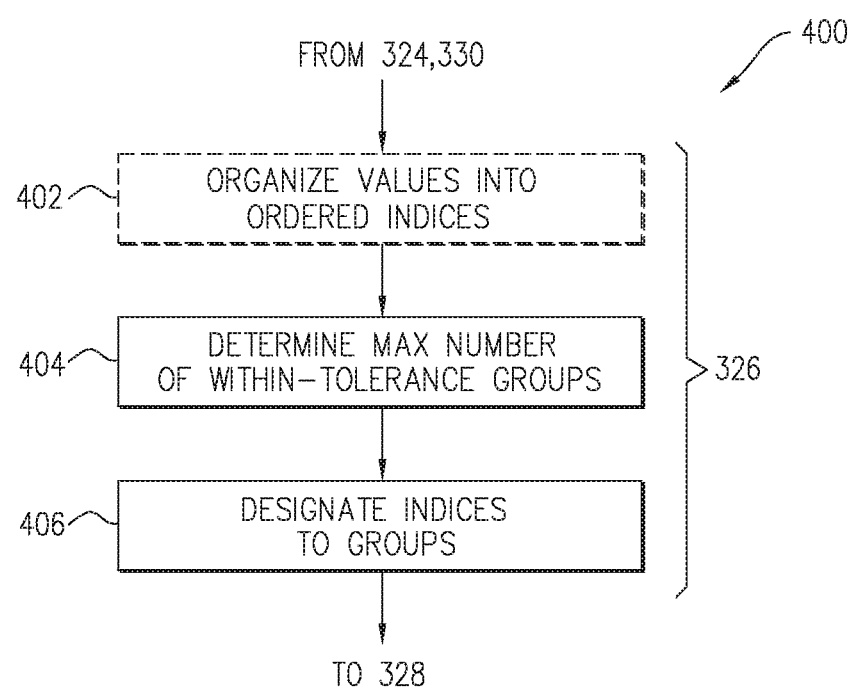
Figure 18:
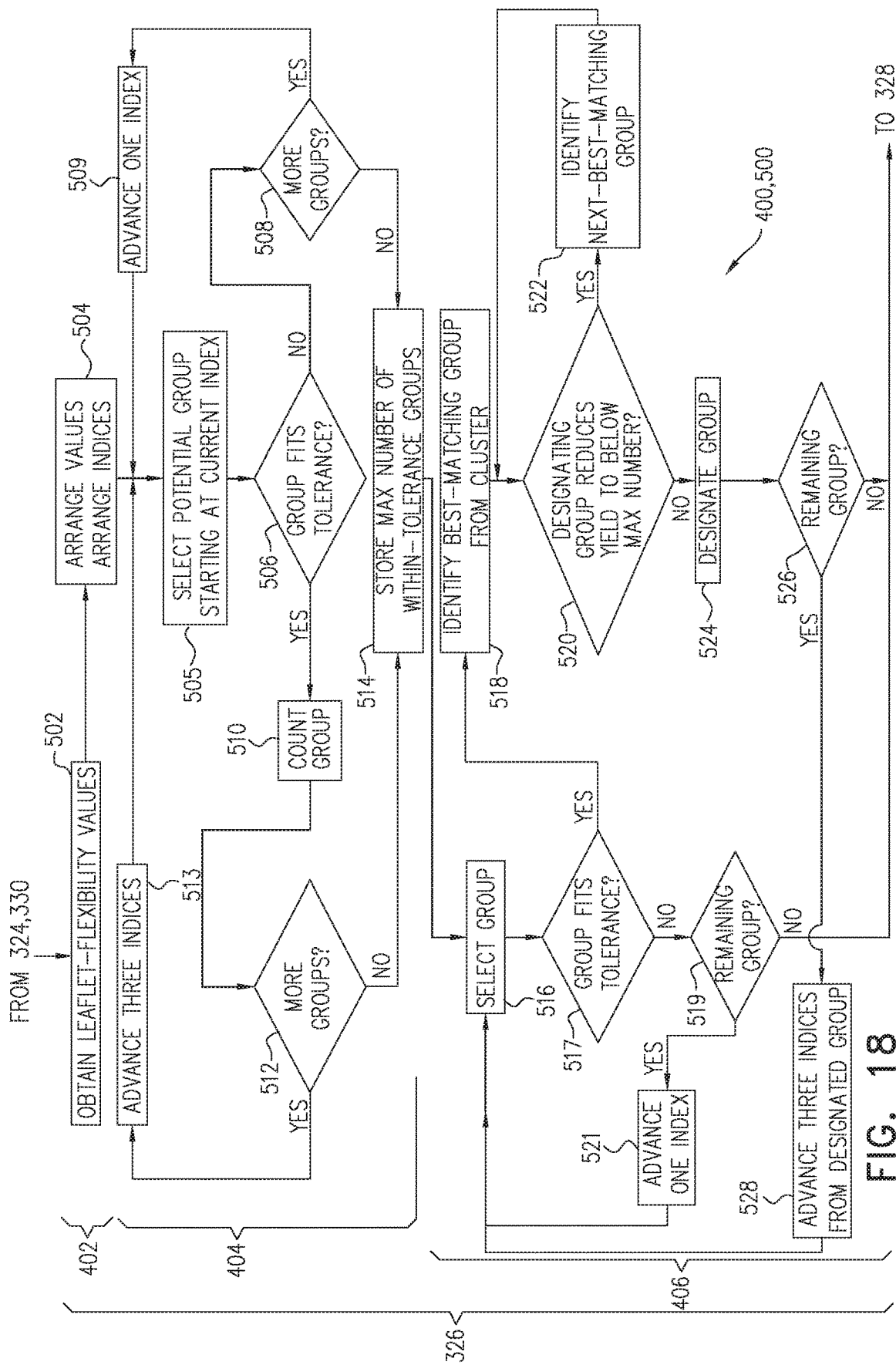

Typically, grouping is optimized responsively to two criteria: (i) As many leaflets as possible from the aggregate of leaflets should be designated to a leaflet group (i.e., maximizing yield and/or minimizing wastage). (ii) Leaflets designated to a leaflet group should have the most similar leaflet-flexibility values attainable (e.g. the leaflets should be "best-matching" leaflets). Thus, ideally, a maximal number of best-matching leaflets is desired. There is typically a trade-off between these criteria. If an intra-group tolerance is very low (e.g., only the very best matched leaflets are designated to a group), a total number of within-tolerance (i.e. a yield of) leaflet groups may be unacceptably low. Similarly, ensuring a maximal yield of complete leaflet groups may require designating, to the same group, leaflets that are insufficiently similar to each other. Described hereinbelow, with reference to FIGS. 17 and 18, are techniques for facilitating optimization of leaflet grouping and/or achieving acceptable trade-offs.

Typically, designating leaflets 30 to leaflet groups is accomplished without further moving or otherwise manipulating the leaflets (e.g. while the leaflets are stored in storage array 104, as described hereinabove in reference to FIGS. 13A-B and 14A-B). Circuitry 40 typically designates the leaflets of the aggregate into leaflet groups (step 326), and indicates the designated leaflet groups to the operator (step 328). For some applications, the leaflet group designations are indicated using indicator 120, 220 as described hereinabove in reference to FIGS. 13A-B and 14A-B.

In response to this indicating, the operator can then group the leaflets (i.e., physically gather the leaflets) into groups (step 332) and utilize the groups of leaflets (step 336), e.g., by assembling the leaflets together in a prosthetic heart valve.

As described hereinabove with respect to step 326, the intra-group tolerance determines which leaflets may be designated into groups with which other leaflets. Typically, this means that the flexibility value of each leaflet within a group must, at a minimum, be within the intra-group tolerance to the flexibility value of each other leaflet within that group. Intra-group tolerances are typically received (e.g. as input from operator), using circuitry 40, and are described in more detail hereinbelow.

Reference is made to FIGS. 17, 18, 19, 20A-D, 21A-J, 22 and 23A-B, which are flowcharts and schematic illustrations that illustrate techniques for designating groups of leaflets, in accordance with some applications of the invention. For some applications, these figures represent step 326 of method 300.

FIG. 17 is a flowchart that schematically illustrates at least some steps of a method 400 that, for some applications, represents step 326 of method 300 in greater detail. FIG. 18 is a flowchart that schematically illustrates at least some steps of a method 500 that, for some applications, represents method 400 (and thereby step 326) in still greater detail. FIGS. 16-18 may therefore be considered to be "nested" relative to each other.

As described hereinbelow in greater detail with respect to FIGS. 18 and 19, first step 402 of method 400 comprises organizing values (e.g. leaflet-flexibility values) into a series of indices. That is, each index represents a leaflet of the aggregate, and has a value that is (or is indicative of) the leaflet-flexibility value of that leaflet, such that a given designated leaflet group is represented by a corresponding designated index group.

Typically, and as shown, indices are arranged according to an order (e.g. according to an order of magnitude of their values). For other applications, it may not be necessary to order the indices. Step 402 is therefore indicated as being optional by the broken box in FIG. 17. However, in the description that follows, ordering the indices facilitates subsequently grouping the indices.

Next, a maximum number of index groups that conform to the intra-group tolerance (henceforth "within-tolerance" index groups), which may be attained from the series of indices, is determined (step 404). For some applications, an index group conforms to the intra-group tolerance if (i) it includes a predetermined number of indices whose values fit within an intra-group tolerance, and (ii) the flexibility value of each index of the index group is within the intra-group tolerance with respect to the leaflet-flexibility value of each other index of index group. That is, the intra-group tolerance defines a maximum allowable difference between values of a within-tolerance index group. Step 404 is also described in greater detail with respect to FIGS. 18, 19 and 20A-D.

Subsequently, the indices are designated to index groups (step 406). As described hereinbelow in greater detail with respect to FIGS. 18, 21A-J and 22, best-matching indices (e.g. indices having most similar values) may be designated into an index group.

However, if doing so would reduce the total number of within-tolerance groups, compared to the maximum number determined in step 404, then an iterative process is performed, testing next-best-matching leaflets until the grouping does not reduce the total number of within-tolerance groups.

FIG. 18 provides still further detail regarding step 326 of method 300 (e.g., further detail regarding steps 402, 404, and 406 of method 400), in accordance with some applications of the invention, by illustrating a method 500.

Leaflet-flexibility values are obtained, e.g. using circuitry 40 (step 502). For example, the leaflet-flexibility values may be retrieved from the memory of circuitry 40, e.g., after having been derived as described hereinabove. Alternatively or in addition, the leaflet-flexibility values may be entered by the operator (e.g. using a user-interface).

The leaflet-flexibility values are then arranged, in order of magnitude, as a series of indices (step 504), which will subsequently be analyzed. Typically, circuitry 40 assigns a respective index number to each of the leaflet-flexibility values. As shown in FIG. 19, leaflet-flexibility values representing the exemplary aggregate of leaflets are arranged into an exemplary series of indices i1-i23, each index having its particular value (e.g., its particular leaflet-flexibility value) (FIG. 19).

Figure 19:
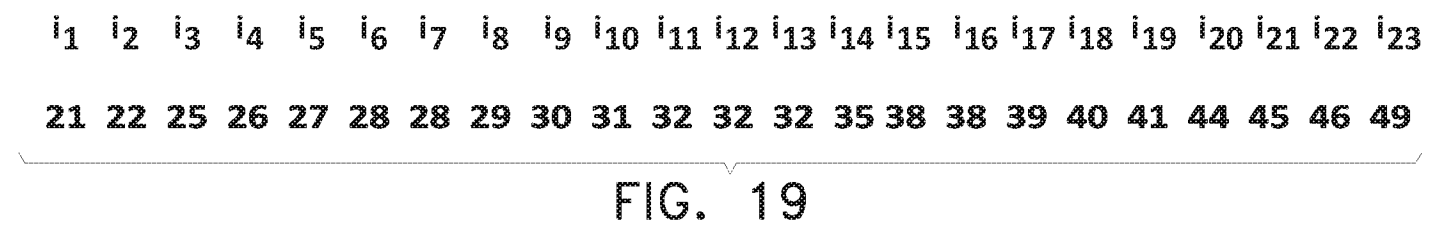

For example, and shown in FIG. 19, the series of indices may be arranged according to an ascending order of magnitude, such that the first index (i1) is assigned the lowest value (in this case, a value of 21), the second index (i2) is assigned the subsequent value (in this case, a value of 22), and the third index (i3) is assigned the following value (in this case, a value of 25), etc. Alternatively, the series of indices may be arranged according to a descending order of magnitude. It is hypothesized by the inventors that initially arranging the indices according to an order of magnitude facilitates subsequently grouping the series of indices to index groups, as described hereinbelow.

Together, steps 502 and 504 of method 500 may correspond to step 402 of method 400. That is, step 402 may comprise steps 502 and 504.

Subsequently, the maximum number of index groups that may be attained from the series of indices is determined (step 404). Each index group comprises a predetermined number of indices. In the description hereinbelow, the predetermined number of indices in an index group is three (corresponding to three leaflets of a leaflet group). Therefore, the term "trio" is used henceforth as a specific example in reference to FIGS. 17-18. Although a trio of leaflets is typically desirable for a prosthetic heart valve implanted at a native mitral valve, this is not meant to exclude cases wherein it may be desirable to designate leaflets 30 into groups comprising fewer (e.g. two leaflets typically desirable for use in a prosthetic heart valve implanted at a native tricuspid valve), or more (e.g., four) leaflets.

Each designated index group conforms to a predetermined intra-group tolerance. That is, all of the indices within an index group must have a value that is within the intra-group tolerance of all of the other indices within the index group. Therefore, each index group must, at a minimum, (i) contain the predetermined number of indices, and (ii) contain only indices that are within the intra-group tolerance of each other.

In the example shown, the intra-group tolerance is defined as 2. Thus, indices having values differing by no more than two may be included in a trio.

Determining the maximum number of within-tolerance trios (step 404) begins with selection of a potential trio (step 505), starting at a first trio T1, which includes indices i1, i2, and i3 (FIG. 20A). Throughout this application, each trio is numbered according to the first index of that trio, such that a trio TN includes index iN and the subsequent two indices. Therefore, trio T2 includes indices i2, i3, and i4; trio T3 includes indices i3, i4, and i5, and so on.

For some applications, an index group-differential (e.g. an index trio-differential), equal to a difference between a highest value of the trio, and a lowest value of the trio, is calculated in order to determine whether the trio conforms to the intra-group tolerance (step 506). If the trio-differential is equal to, or less than the intra-group tolerance, then the trio is considered to conform to the intra-group tolerance, and is therefore counted as a within-tolerance trio. For applications in which the indices are sorted according to ascending order of magnitude, trio-differential "delta_t" value of the trio is calculated by subtracting the first index of the trio from the last index of the trio. FIG. 20A shows calculation of delta_t1 of potential trio T1, which is calculated to be 4. Because delta_t1 is greater than 2, trio T1 does not conform to the intra-group tolerance. That is, since the trio-differential is greater than the intra-group tolerance, trio TI is not counted as a within-tolerance trio.

The next step in determining the maximum number of within-tolerance trios is to determine whether sufficient subsequent indices remain in order for a subsequent potential trio to be evaluated (step 508). If the answer is "yes" (as in this case, since at least), analysis continues by advancing one index (step 509) in the series, and potential trio T2 is selected (step 505, FIG. 20B). (It is to be noted that FIG. 20B shows advancing by one index because, in this particular example, the previous potential trio (T1) did not conform to the intra-group tolerance.) Similarly to trio T1, trio-differential delta_t2 of trio T2 is calculated to be 4. Because delta_t2 is greater than 2, trio T2 also does not conform to the intra-group tolerance (step 506).

Again, sufficient subsequent indices remain in order for a subsequent potential trio to be evaluated (step 508). That is, at least one index has yet to be selected. The analysis therefore continues by advancing one index in the series (step 509), and potential trio T3 is selected (step 505). As shown in FIG. 20C, trio-differential delta_t3 of trio T3 is found to be 2. Thus, trio T3 conforms to the intra-group tolerance (step 506), and is therefore counted (i.e., added to a count of within-tolerance groups, step 510) as a within-tolerance trio. In FIG. 20C, the broken rectangle that indicates trio T3 is bolded in order to represent that this trio is counted.

After within-tolerance trio T3 is counted, sufficient subsequent indices still remain in order for a subsequent potential trio to be evaluated (step 512). The analysis therefore continues by advancing along the indices (step 513).

Since trio T3 was counted as conforming to the intra-group tolerance, the analysis advances by three indices (as opposed to by one index in cases in which the trio did not conform to the intra-group tolerance). That is, because indices i3, i4, and i5 already belong to a within-tolerance trio, no other trios that include any of these three indices are evaluated in step 404. Therefore, method 400 then returns to step 505, as described hereinabove, mutatis mutandis, with the next potential trio to be evaluated being T6. That is, the "current index" of step 505 at this stage will be i6.

Figure 20D:
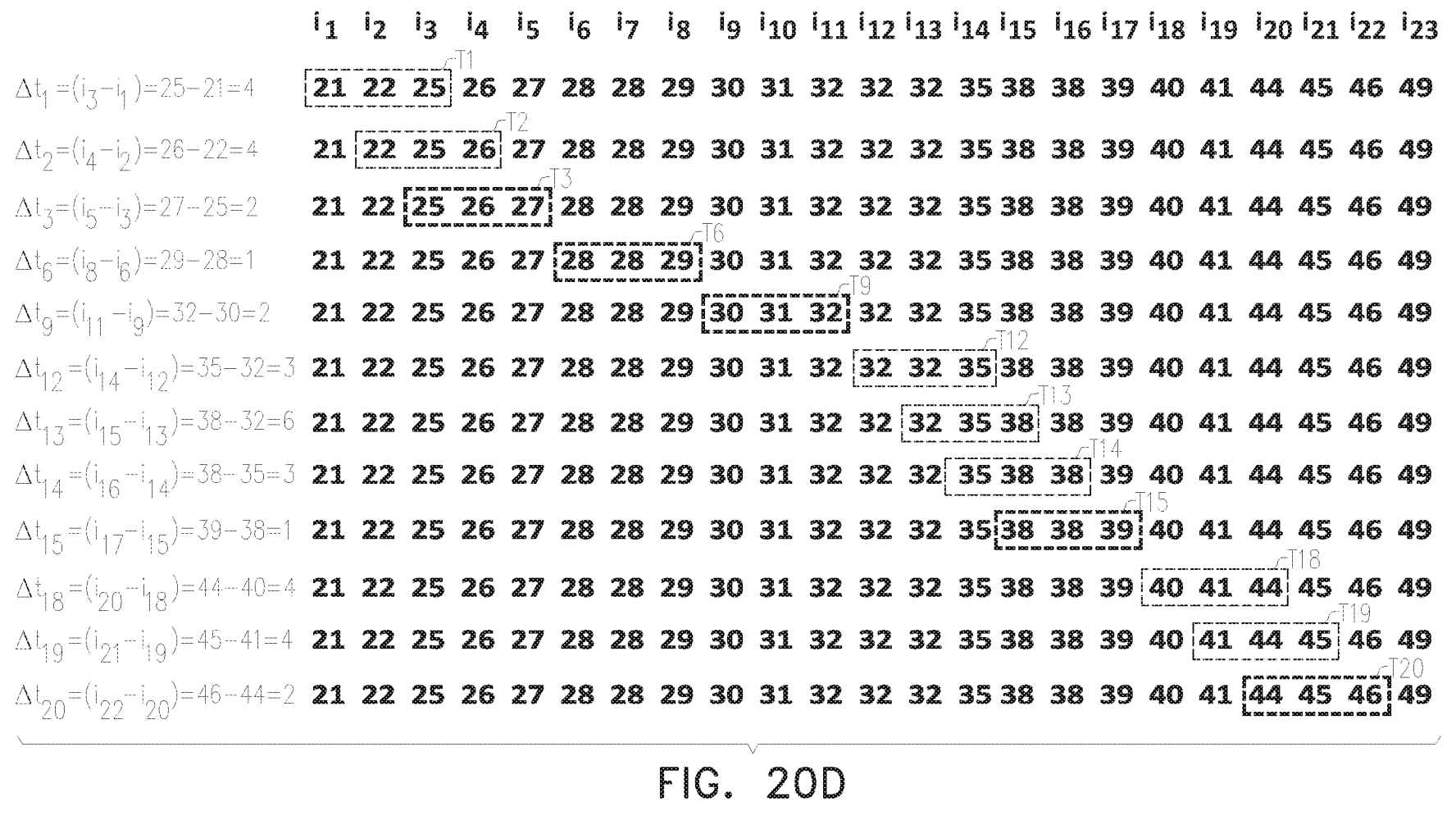

In this way, successive iterations are performed, determining the number of within-tolerance trios, until no trios remain to be evaluated. FIG. 20D schematically illustrates the result that would be obtained by performing step 404 on this exemplary series of indices with an intra-group tolerance of 2, and a group size of 3.

Each of the trios that would have been evaluated are indicated by a broken rectangle. Those of the trios that conformed to the intra-group tolerance are indicated by the broken rectangle being bolded. As shown, in this exemplary series, the maximum number of trios that conform to the intra-group tolerance that it is possible to obtain from the series is found to be five. At this point, this maximum number is stored, hereafter the "stored maximum number," e.g. in the memory of circuitry 40 (step 514).

Together, steps 505, 506, 508, 509, 510, 512, 513, and 514 of method 500 may correspond to step 404 of method 400. That is, step 404 may comprise steps 505, 506, 508, 509, 510, 512, 513, and 514.

After the maximum number of trios that conform to the intra-group tolerance, that are attainable from the series is determined and stored (step 404), the indices are designated to index groups (step 406), as elaborated hereinbelow.

Firstly, a preliminary index group (e.g. first trio T1) is selected for evaluation (step 516). Trio T1 is found to not conform to the intra-group tolerance (step 517, FIG. 21A).

Since there is at least one remaining unevaluated trio (step 519), analysis continues by advancing one index (step 521) to trio T2 (step 516, FIG. 21B). Index i1 is therefore discontinued from analysis of the series of indices. Although discontinued indices therefore represent leaflets that will not be included in leaflet groups with other leaflets from the current aggregate of leaflets, discontinued leaflets may be stored (e.g. in storage array 104) for later use (e.g. as part of another aggregate of leaflets).

The next preliminary index group, trio T2, is also found to not conform to the intra-group tolerance (step 517, FIG. 21B), and index i2 is therefore also discontinued from further evaluation.

Since there is at least one remaining unevaluated trio (step 519), analysis continues by advancing one index (step 521) to the next preliminary index group, trio T3 (step 516, FIG. 21C).

Trio T3 is found to conform to the intra-group tolerance, and is therefore found to be a within-tolerance trio (step 517) labelled with a bolded broken rectangle in FIG. 21C. Evaluation of trio T3 continues by selecting the trio that has, within it, the most similar leaflet-flexibility values (i.e., a "best-matching trio") from among a cluster of indices beginning with within-tolerance trio T3 (i.e., the trio that was found to conform to the tolerance in step 517). Typically, the best-matching trio of a given cluster has a trio-differential that is no greater than the trio-differential of any other trio belonging to that cluster.

The cluster typically comprises the within-tolerance trio (in this case T3) and the subsequent two indices (in this case T4 and T5). This can also be stated as the cluster comprising the within-tolerance trio (in this case T3, which corresponds to index i3), and subsequent trios that correspond to the other indices contained within the within-tolerance trio (in this case T4 and T5). More generally stated (e.g., to encompass group sizes other than 3), the cluster typically comprises the within-tolerance index group (i.e., the index group that was found to conform to the tolerance in step 517) and the index groups that correspond to the other indices contained within the within-tolerance index group. Therefore, the number of index groups in the cluster is equal to the number of indices comprising each index group—e.g., the number of leaflets that will be combined in a prosthetic valve.

Figure 21D:
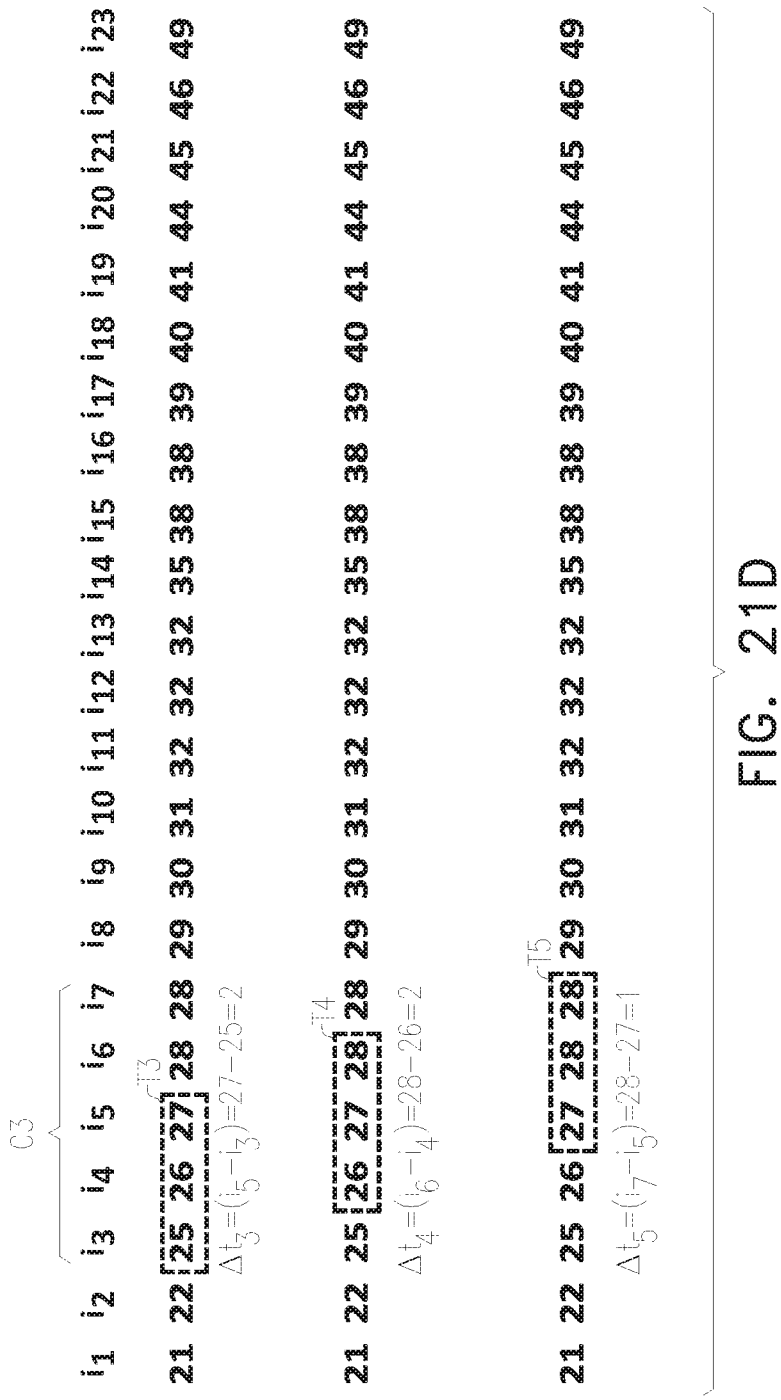
Figure 21F:
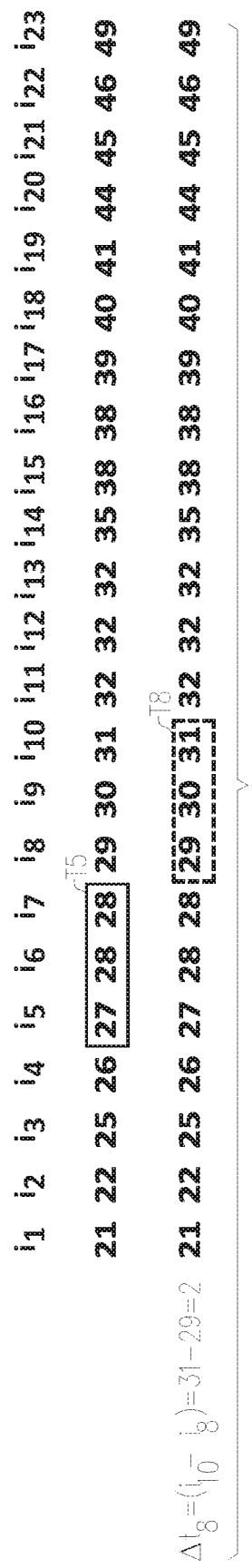

For the purposes of selecting the best-matching trio of cluster C3 (step 518), the delta_t value (as described hereinabove in reference to FIGS. 20A-D, mutatis mutandis) is typically calculated for each trio of the cluster (FIG. 21D). Further typically, the delta_t values of each trio are then compared to identify a best-matching trio having a lowest trio-differential out of the cluster of trios.

For example, and as shown in FIG. 21D, the delta_t values of trio T4 and trio T5 are calculated as 2 and 1, respectively. Therefore, trio T5 has the lowest delta_t value out of the three trios, and is therefore identified as the best-matching trio of cluster C3 (step 518). It is to be understood that this process is applicable to groups of other sizes, mulatis muandis.

For some applications, other parameters may be calculated in order to identify the best-matching trio of a cluster by comparing the closeness of fit between the leaflets comprising each trio of the cluster.

For some such applications, an additive differential value may be calculated. The additive differential ("sum_delta_t") of a particular trio is the sum of the differences between each of the three pairs of indices within that trio. For example, the additive differential of trio T3 (sum_delta_t3) is calculated as (i4−i3)+(i5−i4)+(i5−i3)=(26−25)+(27−26)+(27−25)=1+1+2=4.

For some applications (e.g. if the predetermined index group size is two or three), the sum_delta_t values of index groups may be equal to the delta_t values of those same index groups. For other applications (e.g. if the predetermined index group size is four or greater), the sum_delta_t values of index groups may not equal the delta_t values of those index groups. For some such applications, sum_delta_t values may reflect, more accurately than delta_t values, the degree to which leaflet-flexibility values of leaflets within a given leaflet group match each other. It is therefore hypothesized by the inventors that using sum_delta_t values may be particularly advantageous when identifying the best-matching index group within a of indices, for applications in which the predetermined index group size is four or greater.

Alternatively or in addition, an average differential ("avg_delta_t") of a particular index group may be calculated to compare the closeness of fit between the indices within each index group of the cluster, by averaging the differences between each of the pairs of indices within that index group. For example, avg_delta_t3 may be calculated as (1+1+2)/3=1.33.

Alternatively or in addition, a sum of the squares of the differences between (sum^_delta_t) each of the pairs of indices within that index group may be calculated to compare the closeness of fit between the index within each index group of the cluster. For example, sum^_delta_t3 may be calculated as $1^2+1^2+2^2=6$. It is to be noted that the scope of the present invention also includes the use of other appropriate mathematical functions to represent the respective differentials of the index groups.

Evaluation of cluster C3 continues by determining whether designating the best-matching trio of the cluster (in this case T5) as an index group to be subsequently indicated in step 328 (FIG. 16) would reduce the total number of within-tolerance trios attainable from the series, and thereby the total yield of leaflets from the aggregate (step 520). The number of additional within-tolerance trios that may be attained from the remainder of the series is calculated in the same manner described hereinabove in reference to FIG. 20D, mutatis mutandis, but starting after hypothetically-designated trio T5. This is illustrated in FIG. 21E, in which trio T5 is outlined in by a dot-dash line, to represent that T5 is the trio whose designation is currently being assessed. As shown in FIG. 21E, four potential within-tolerance trios are found to be attainable should trio T5 be actually designated (trios T8, T11, T15 and T20, labelled with bold dotted rectangles). This results in the selection of a total of five trios, which is equal to the stored maximum number determined in step 404 and stored in step 514. (Thus, designating best-matching trio T5 would not reduce the total yield of leaflet groups from the aggregate.) Therefore, trio T5 is actually designated as an index group (step 524).

Since at least another trio of indices remains to be evaluated (step 526), the analysis continues by advancing three indices—i.e., to the trio that corresponds to the first index after previously-designated trio T5 (step 528). Therefore, in this case, trio T8 (which includes indices i8, i9, and i10) is selected for evaluation (step 516). Trio T8 is found to be a within-tolerance trio, (step 517, FIG. 21F). Accordingly, the next step is identifying the best-matching trio from among cluster C8, which includes trios T8, T9 and T10 (FIG. 21G). The delta_t value of trio T10 is found to be the lowest from among the trios of cluster C8, identifying trio T10 to be the best-matching trio of cluster C8 (step 518).

Figure 21H:
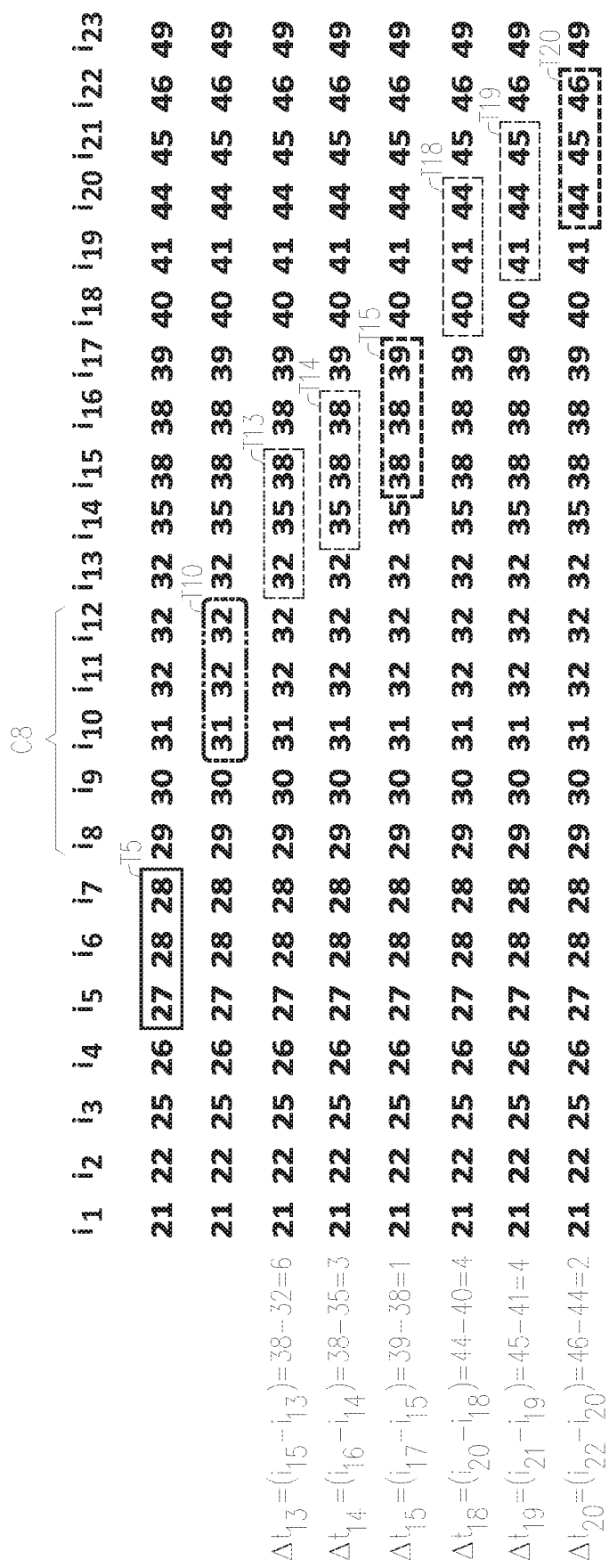

The next step is therefore determining whether designating best-matching trio T10 would reduce the total number of within-tolerance trios to below the maximum number that was determined in step 404 (step 520). Thus, the number of additional within-tolerance trios that may be attained from the remainder of the series is calculated in the same manner described hereinabove, mutatis mutandis, but starting after hypothetically-designated trio T10. As shown in FIG. 21H, two additional within-tolerance trios are found to be attainable should trio T10 be actually designated (trios T15 and T20, labelled with bold dotted rectangles). This results in the selection of a total of four potential trios, which is less than the stored maximum number. (Thus, designating best-matching trio T10 would reduce the total number of within-tolerance leaflet groups attainable from the aggregate.) Therefore, trio T10 is not designated as an index group (step 524). Rather, the analysis continues by selecting a next-best-matching trio (step 522) from within cluster C8.

As shown in FIG. 21G, the remaining trios of cluster C8 are trios T8 and T9, each of which has a trio-differential of four, meaning that in this particular case, there are two next-best-matching trios.

It is worth noting that in this illustrative example using indices i1-i23, the leaflet-flexibility values are integers, which increases the likelihood that two trios of the same cluster may have identical trio-differentials. However, in reality, leaflet-flexibility values typically include decimals or fractions (i.e., leaflet-flexibility values are typically "floats"), reducing the likelihood of two trios having identical trio-differentials.

For some applications in which a next-best-trio must be identified from among two trios having equal trio-differentials, the trio appearing later in the series of indices (e.g. trio T9, FIG. 21I) is identified as the next-best-matching trio. For other applications, the trio appearing earlier in the series is so identified.

Figure 21I:
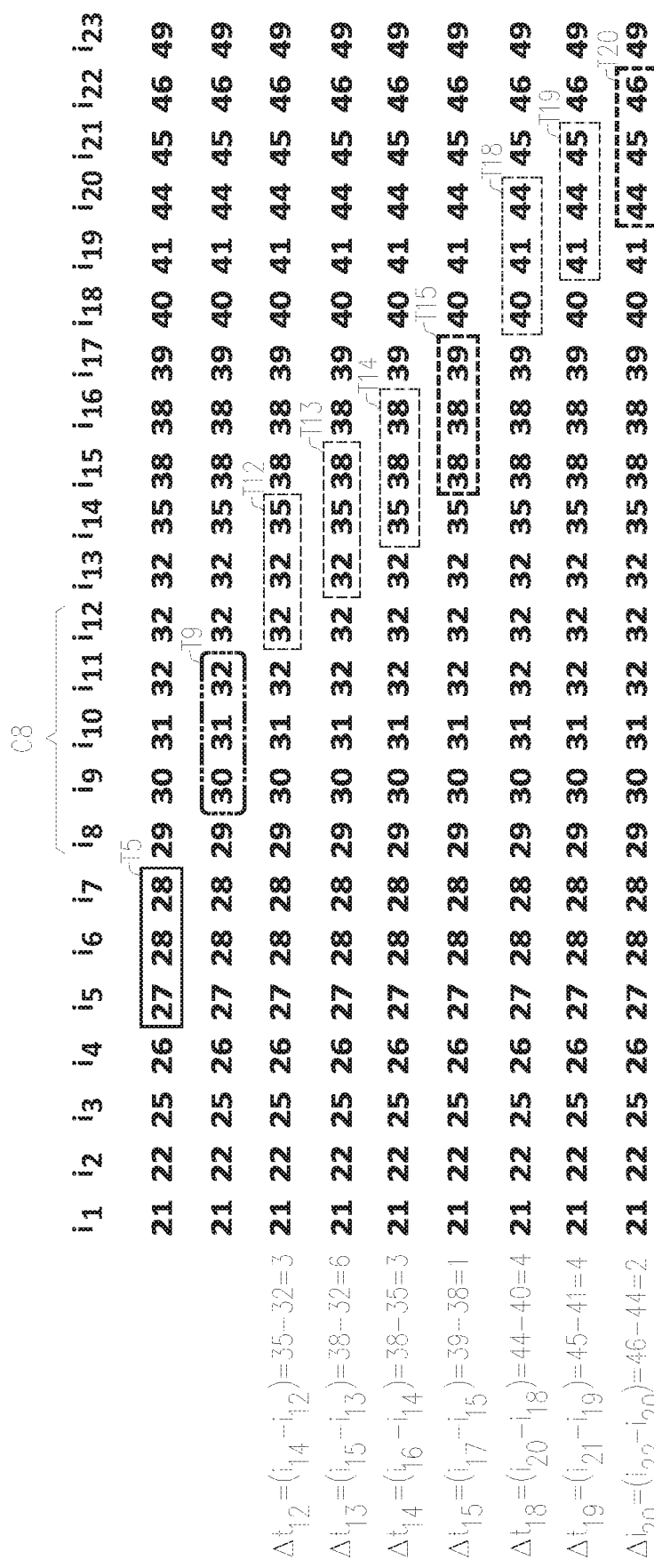

As shown in FIG. 21I, next-best-matching trio T9 is evaluated by determining whether designating trio T9 would reduce the total number of within-tolerance trios (step 520). Similarly to as described hereinabove in reference to trio T10 in FIG. 21H, the number of additional within-tolerance trios that may be attained from the remainder of the series is calculated after hypothetically designating next-best-matching trio T9. As shown in FIG. 21I two additional within-tolerance trios are found to be attainable should trio T9 be actually designated (trios T15 and T20, labelled with bold dotted rectangles). This results in the selection of a total of four potential trios, which is less than the stored maximum number. (Thus, designating next-best-matching trio T9 would reduce the total number of leaflet groups.) Therefore, trio T9 (in this case, a first next-best-matching trio) is not designated as an index group (step 524). Rather, the analysis continues with identification of another (e.g. a second) next-best-matching trio (trio T8) from within cluster C8 (step 522, FIG. 21J).

Figure 21J:
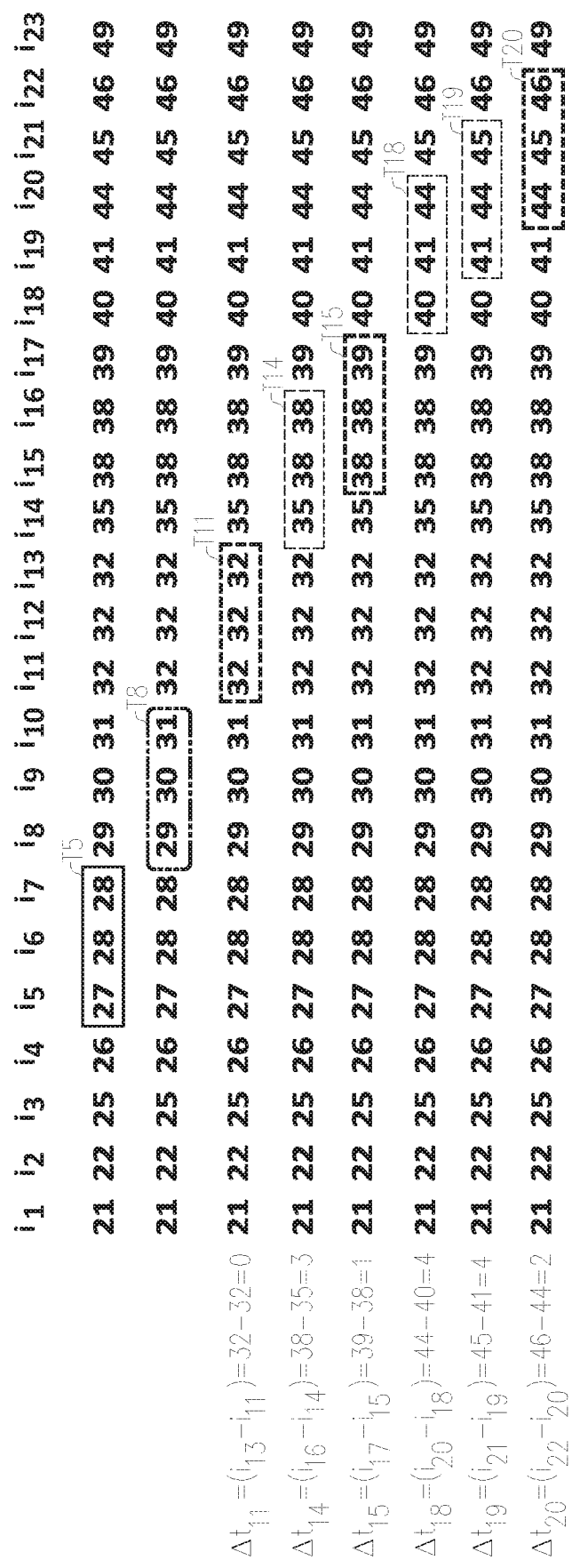

As shown in FIG. 21J, next-best-matching trio T8 is evaluated by determining whether designating trio T8 would reduce the total number of within-tolerance trios (step 520). Similarly to as described hereinabove in reference to trios T10 and T9, the number of additional within-tolerance trios that may be attained from the remainder of the series is calculated after hypothetically designating next-best-matching trio T8. As shown in FIG. 21J, three additional within-tolerance trios are found to be attainable should trio T8 be actually designated (trios T11, T15 and T20, labelled with bold dotted rectangles). This results in the selection of a total of five potential trios, which is equal to the stored maximum number. (Thus, designating best-matching trio T8 would not reduce the total number of leaflet groups.) Therefore, trio T8 is designated as an index group (step 524).

Since at least another trio of indices remains to be evaluated (step 526), the analysis continues by advancing three indices—i.e., to the trio that corresponds to the first index after previously-designated trio T8 (step 528). Therefore, in this case, trio T11 (which includes indices i11, i12, and i13) is selected for evaluation (step 516).

For some applications, remaining indices are identified by advancing along the indices, such that steps 512 and 513 may be combined. That is, whether sufficient subsequent indices remain in order for a subsequent potential trio to be evaluated, is determined (step 512) by attempting to advance three indices (step 513). For example, successful advancement by three indices demonstrates that sufficient indices remain in order for a subsequent potential trio to be evaluated. In contrast, failure to advance by three indices demonstrates that insufficient indices remain in order to evaluate a subsequent potential trio. However, for the sake of clarity, advancing three indices (step 513) and determining if sufficient indices remain in order to do so (step 512) are described as discrete steps. Similarly, additional pairs of steps (e.g., steps 508 and 509, steps 519 and 521, steps 526 and 528) may each respectively be combined. For the sake of clarity, these pairs of steps are described hereinabove as discrete steps.

As described hereinabove in reference to FIGS. 21A-C and 21F, trio T11 is evaluated to determine whether the trio conforms to the tolerance (step 517), and analysis of the indices continues, as described hereinabove, until there are no remaining trios (steps 519, 526).

Together, steps 516, 517, 518, 519, 520, 521, 522, 524, 526, and 528 of method 500 may correspond to step 406 of method 400. That is, step 406 may comprise steps 516, 517, 518, 519, 520, 521, 522, 524, 526, and 528.

In this way, successive iterations of step 406 are performed, until no trios remain to be evaluated. FIG. 22 schematically illustrates results that would be obtained by performing step 406 on this exemplary series of indices with a predetermined intra-group tolerance of 2, and a group size of 3. Each of the trios (T5, T8, T11, T15 and T20) that would be designated are indicated by a solid rectangle. It is to be noted that these five trios that would be designated by performing step 406 are not identical to the five trios (T3, T6, T9, T15 and T20) that were counted to determine the maximum number of within-tolerance trios (step 404, FIG. 20D). It is further to be noted that a cumulative average differential "cumul_avg_delta_t" value of the designated trios, calculated by averaging the avg_delta_t values of each of the designated trios ((2+4+0+2+4)/5=2.4) is lower than the cumul_avg_delta_t value of the five trios that were counted to determine the maximum number (step 404, (4+2+4+2+4)/5=3.2). This illustrates an advantage of this approach to designating groups of leaflets, in accordance with some applications of the invention. Therefore, for some applications, the cumul_avg_delta_t value of the designated trios is lower than the cumul_avg_delta_t value of the within-tolerance index groups that were previously counted to determine the stored maximum number.

It is to be noted that, in some instances (e.g., due to an aggregate of leaflets having leaflets whose leaflet-flexibility values are of a particular similarity and/or order), it may be possible that the cumul_avg_delta_t value of the designated trios is equal to the cumul_avg_delta_t value of the within-tolerance index groups.

The designated index groups are then indicated (step 328 of FIG. 16.) to the operator as representing leaflet group designations, from where method 300 continues, as described hereinabove. This indication (e.g. output from circuitry 40) may occur immediately, or the designated trios may be stored in the memory for subsequent indication.

In the example shown, of the 23 indices visible in FIG. 23, only 15 were designated to index groups. That is, the yield from the 23 visible indices is about 65 percent. For some applications, a typical yield is less than 80 percent (e.g. less than 50 percent, such as fewer than 30 percent) and/or at least 10 percent, (e.g., 10-80 percent, such as 10-50 percent) of the leaflets of a given aggregate being designated into leaflet groups.

For some applications, it may be desirable to adjust the intra-group tolerance used as a basis for designating the index groups, e.g., in order to obtain a desirable (e.g., optimal) compromise between yield and closeness of fit within index groups. This is represented in FIG. 16 by step 330. As shown, step 330 is typically performed prior to the actual (e.g., final) indication of the designated index groups (step 328) that will be used by the operator to group the leaflets into leaflet groups (step 332).

Figure 23A:
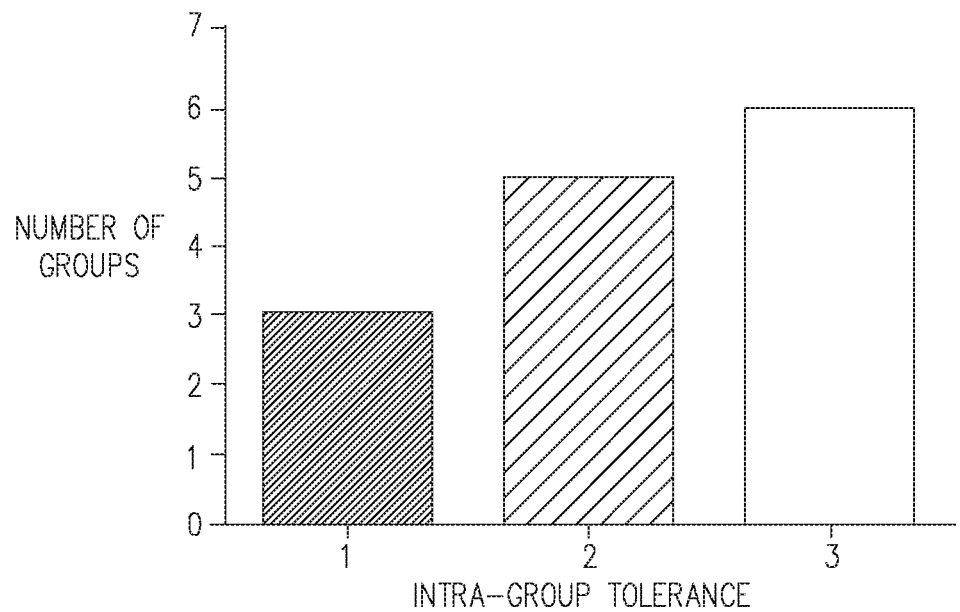
Figure 23B:
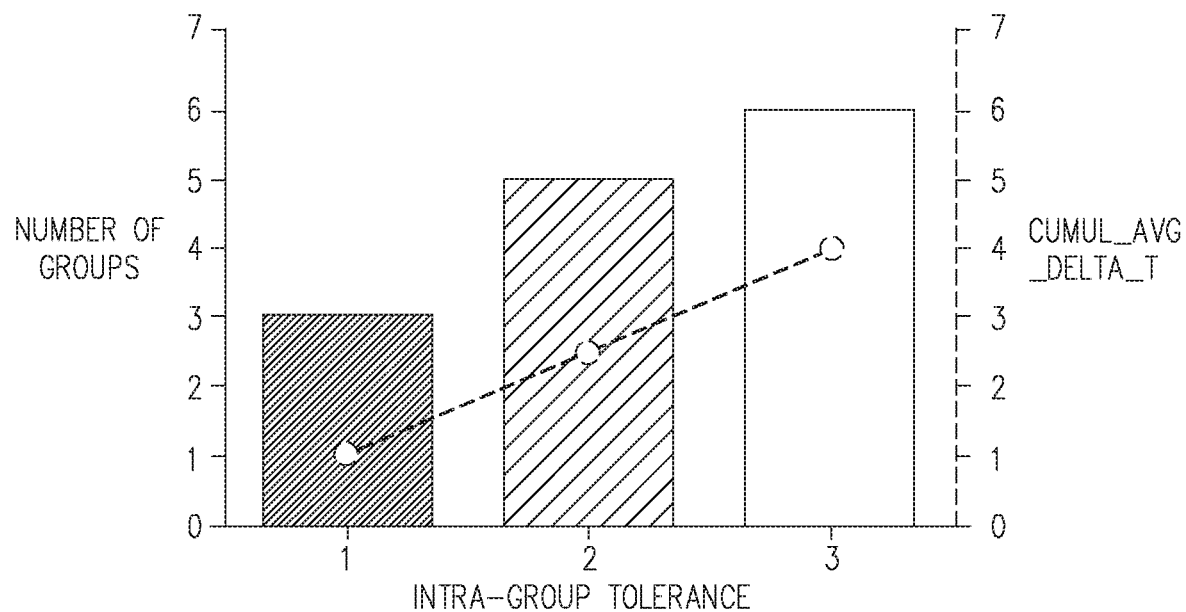

Reference is now also made to FIGS. 23A-B, which each show graphical representations of exemplary alternate leaflet group yields resulting from alternate intra-group tolerances, in accordance with some applications of the invention. Graphical representations such as these may be displayed on a display. For some applications, displaying alternate leaflet group designations, such as those shown in FIGS. 23A-B, advantageously aids the operator in electing whether to adjust tolerances (step 330). For some applications, step 330 is facilitated by circuitry 40 providing a preview (e.g., on a display) relating to the designated leaflet groups (e.g., a yield of preliminary index groups) that would result from the use of different intra-group tolerances. For example, information displayed in the preview may offer the operator an opportunity to exercise judgement (e.g. relative to the trade-off between attaining (i) a larger number of within-tolerance leaflet groups and (ii) a greater closeness of fit of leaflets of each leaflet group, as described hereinabove), based upon specialized medical or technical training, and/or based on current manufacturing or supply considerations.

For some such applications, the operator selects one of the alternate yields, such that the operator has the option of revising the intra-group tolerance by selecting an alternate yield stemming from an intra-group tolerance other than the predetermined tolerance. For example, the intra-group tolerance may be increased responsively to designating an undesirably low yield of within-tolerance leaflet groups stemming from use of the predetermined tolerance with a particular aggregate of leaflets.

FIG. 23A shows that using a predetermined tolerance of 2 would yield a total of five leaflet groups. Alongside this, allowing the inclusion of less closely fitting leaflets within the same leaflet group, by elevating the tolerance to 3, would increase the yield by one leaflet group, to six within-tolerance leaflet groups. On the other hand, requiring leaflet groups to include only more closely fitting leaflets, by reducing the tolerance to 1, would reduce the yield to three leaflet groups. It is hypothesized by the inventors that representing this relationship between intra-group tolerance and the number of within-tolerance leaflet groups advantageously provides the operator with an opportunity to elect whether to adjust the tolerance (step 330).

For some applications, it may be desirable to include, alongside alternate numbers of within-tolerance leaflet groups, a parameter reflecting the average closeness of fit of each alternate leaflet group yield. In addition to the relationship between intra-group tolerance and the yield of leaflet groups shown in FIG. 23A, FIG. 23B further includes cumulative average differential "cumul_avg_delta_t" values of alternate index groups, which represent the average closeness of fit of the alternative leaflet groups. FIG. 23B shows that the five trios attainable using the predetermined tolerance of 2 have a cumul_avg_delta_t value of 2.4 ((2+4+0+2+4)/5=2.4), while the three trios attainable using an intra-group tolerance of 1 would fit more closely, having a cumul_avg_delta_t value of 1.2 ((2+2+2)/3=1.2), and the six trios attainable using an intra-group tolerance of 3, would fit less closely, having a cumul_avg_delta_t value of 3.7 ((4+2+4+6+2+4)/6=3.7). As described hereinabove in reference to FIG. 23A, intra-group tolerances may be adjusted (step 330). It is hypothesized by the inventors that indicating both the number of leaflet groups, as well as the cumul_avg_delta_t values, of alternate leaflet group yields, may further facilitate the exercising of judgement relative to the trade-off between achieving a maximal yield of within-tolerance leaflet groups and each leaflet group including "best-matching" leaflets, as described hereinabove.

Responsively to the operator's election whether to revise the tolerance in step 330, the final designation (e.g. identities of trios of leaflets) are then indicated to the operator (step 328), who then groups the leaflets (step 332), responsively to the final leaflet group designations. Further typically for such applications, if the operator selects the leaflet group designation resultant from the predetermined intra-group tolerance, this designation is indicated to the operator, effectively skipping over optional step 330. For some applications, step 330 is skipped entirely, and the leaflet group designation indicated in step 328 is the designation stemming from the predetermine intra-group tolerance in step 326.

For some applications, grouped leaflets 30 undergo a validation step 334, subsequently to being grouped into their leaflet groups. For example, although leaflets 30 would have already been typically tested for flexibility in a first orientation (e.g. with the rough side facing upwards), it may be desirable to validate the leaflets by testing the leaflets of a leaflet group, in a second orientation that is inverted with respect to the first orientation (e.g. with the smooth side facing upwards).

For example, validation may entail repeating steps 310-322, mutatis mutandis, with leaflets 30 draped across bars 22 in the second orientation. For example, after calculating first-orientation image parameters by digitally analyzing a first-orientation digital image of leaflets 30 in the first orientation, resulting in a first leaflet-flexibility value (steps 310-318), second-orientation image parameters may be calculated by digitally analyzing a second-orientation digital image of leaflets 30 in the second orientation, resulting in a second leaflet-flexibility value.

For example, a leaflet 30 may pass validation if the second leaflet-flexibility value is deemed to be sufficiently similar to the first leaflet-flexibility value. This comparison may be made by a human operator or by circuitry 40. For example, a difference between the first leaflet-flexibility value and the second leaflet-flexibility value may be calculated, such that the leaflet may be counted as validated if the difference is below a predetermined threshold. Alternatively or in addition, the comparison may be facilitated by calculating a symmetry index reflective of the degree to which the first leaflet-flexibility value correlates with the second leaflet-flexibility value.

Leaflets 30 that fail validation are typically discarded. For some applications, the user-interface may be used to indicate to the user which leaflets failed the validation, such that those failed leaflets may be discarded.

If a leaflet of a designated trio of leaflets fails the validation, that leaflet is typically discarded. For some applications, step 326 is then repeated on the entire aggregate but excluding the failed leaflet and its flexibility value. Alternatively, the validated leaflets of the failed leaflet's group (and which are now "orphaned") may be stored for future use (e.g., to be evaluated in another aggregate).

Step 336 represents the utilization of the groups of leaflets, e.g. by assembling the leaflets together in a prosthetic heart valve, or by storing the group of leaflets in a separate container for later use. This step may be performed by the individual who evaluated the leaflets. Alternatively or in addition, step 336 comprises sending the groups of leaflets to a distinct individual, e.g. who assembles the leaflets together in a prosthetic heart valve.

Hereinabove, the group size is described in general as being equal to the number of leaflets that are to be used in (e.g., sewn into) a given prosthetic heart valve (e.g., a group size of three for a trileaflet valve). For some applications, the group size may be larger than the number of leaflets that are to be used in a given prosthetic heart valve, e.g., so as to provide a spare leaflet in case a problem (e.g., damage) occurs to one of the leaflets of a given group, e.g., so that it is not necessary to discard all the leaflets of a group in response to a problem with only one of the leaflets of the group. For example, a group size of four may be used when grouping leaflets for trileaflet valves.

Applications of the invention described herein can take the form of a computer program product accessible from a computer-usable or computer-readable medium (e.g., a non-transitory computer-readable medium) providing program code for use by or in connection with a computer or any instruction execution system, such as circuitry 40.

For some applications, the designating of leaflets 30 to groups is facilitated by an artificial neural network, e.g., with the artificial neural network performing step 326 and/or method 400. For some such applications, training data (e.g. digital images, image parameters, and/or leaflet-flexibility values) are used in conjunction with leaflet group designations described hereinabove.

For some applications in which leaflets 30 are designated to leaflet groups using an artificial neural network, steps 326 and 330 may be performed by the artificial neural network, after which final results are indicated (step 328) to the operator. For some such applications, the trade-off described hereinabove between achieving a maximal number of within-tolerance leaflet groups and each leaflet group including "best-matching" leaflets, is considered by the artificial neural network. It is hypothesized by the inventors that using the artificial neural network to consider the aforementioned trade-off may assist the operator in deciding whether or not to adjust intra-group tolerances (step 330). It is further hypothesized by the inventors that performance of step 330 by the artificial neural network may at least partially obviate specialized medical or technical training of the operator.

For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., circuitry 40) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., circuitry 40) or other programmable data processing apparatus, create means for implementing the functions/acts specified in the methods described in the present application.

These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Circuitry 40 typically comprises a hardware device programmed with computer program instructions to produce a computer processor. For example, when programmed to perform the methods described herein, the computer processor typically acts as a special purpose computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for grouping prosthetic valve leaflets of an aggregate of prosthetic valve leaflets, the method comprising, using a computer processor:
   for each leaflet of the aggregate, in response to an image parameter of the leaflet, deriving a leaflet-flexibility value;
   receiving a group size value;
   designating at least some of the leaflets of the aggregate into designated leaflet groups, (i) based on similarity between the respective leaflet-flexibility value of each leaflet of the aggregate, and (ii) such that each of the designated leaflet groups includes a number of leaflets equal to the group size value; and
   outputting an indication of the designated leaflet groups.

2. The method according to claim 1, wherein:
   the method further comprises receiving an intra-group tolerance, the intra-group tolerance representing a maximum allowable difference between the leaflet-flexibility values of any two leaflets in a given leaflet group; and
   designating at least some of the leaflets of the aggregate into designated leaflet groups comprises designating at least some of the leaflets of the aggregate into designated leaflet groups, such that, for each of the designated leaflet groups, the flexibility value of each leaflet in the designated leaflet group is within the intra-group tolerance with respect to the leaflet-flexibility value of each other leaflet in the designated leaflet group.

3. The method according to claim 1, further comprising, prior to deriving the leaflet-flexibility value for each leaflet of the aggregate of leaflets, calculating the image parameter for each leaflet of the aggregate by digitally analyzing one or more digital images that include the leaflets of the aggregate.

4. The method according to claim 3, further comprising, prior to deriving the leaflet-flexibility value for each leaflet of the aggregate of leaflets, performing an image-quality check routine, wherein performing the image-quality check routine comprises:
   comparing, for each leaflet of the aggregate, the image parameter to a predetermined threshold;

wherein deriving the leaflet-flexibility value for each leaflet of the aggregate of leaflets comprises selectively deriving the leaflet-flexibility value for each leaflet, such that:
   if the image parameter for a given leaflet is found to fit the predetermined threshold, the leaflet-flexibility value is derived for that leaflet, and
   if the image parameter for a given leaflet is found to not fit the predetermined threshold, the leaflet-flexibility value is not derived for that leaflet.

5. The method according to claim 3, wherein calculating the image parameter for each leaflet of the aggregate comprises calculating, for each leaflet of the aggregate, a direct distance between a position of a first leaflet-tip and a position of a second leaflet-tip.

6. The method according to claim 1, further comprising, prior to the step of designating:
   assigning a respective index to each of the leaflet-flexibility values, each of the indices representing a respective one of the leaflets and having the leaflet-flexibility value of the respective one of the leaflets;
   receiving an intra-group tolerance, the intra-group tolerance representing a maximum allowable difference between the leaflet-flexibility values of any two leaflets in a given leaflet group;
   subsequently, determining a maximum number of within-tolerance index groups attainable from the indices, a within-tolerance index group being an index group (i) that includes a number of indices that is equal to the group size value, and (ii) for which the flexibility value of each index in the index group is within the intra-group tolerance with respect to the leaflet-flexibility value of each other index in the index group; and
   subsequently, storing the maximum number,
wherein designating at least some of the leaflets of the aggregate into designated leaflet groups comprises designating at least some of the leaflets of the aggregate into designated leaflet groups, such that:
   for each of the designated leaflet groups, the flexibility value of each index in the designated index group is within the intra-group tolerance with respect to the leaflet-flexibility value of each other index in the designated index group, and
   a total number of the designated index groups is at least half of the stored maximum number.

7. The method according to claim 6, wherein:
assigning the respective index to each of the leaflet-flexibility values comprises arranging the indices in an ordered series in which the indices are ordered according to an order of magnitude of the respective leaflet-flexibility values; and
determining the maximum number comprises iteratively:
   counting a number of successive remaining indices, a successive remaining index being defined as an index that (i) has not yet been counted as an index of a within-tolerance index group, and (ii) being positioned later in the ordered series than any index that has already been counted as an index of a within-tolerance index group
   selecting a potential index group from among the successive remaining indices, such that:
      a lowest index of a potential index group is the index of the potential index group that has a lowest leaflet-flexibility value of the indices of the potential index group, and a highest index of the potential index group is the index of the potential index group that has a highest leaflet-flexibility value of the indices of the potential index group, the potential index group includes a number of successive indices equal to the group size, and the lowest index of the potential index group is the lowest remaining index;

calculating a group-differential of the potential index group, the group-differential being a difference between (i) the leaflet-flexibility value of the highest index of the potential index group, and (ii) the leaflet-flexibility value of the lowest index of the potential index group;

determining whether the group-differential of the potential index group is greater than, or no greater than, the intra-group tolerance, and responsively:

if the group-differential of the potential index group is no greater than the intra-group tolerance, counting the potential index group as a within-tolerance index group, and if the group-differential of the potential index group is greater than the intra-group tolerance, not counting the potential index group as a within-tolerance index group;

responsively to (i) the step of counting the potential index group, and (ii) the identifying the number of successive remaining indices, selectively selecting a successive potential index group including a remaining index, wherein selectively selecting the successive potential index group comprises:

if a preceding potential index group is counted as a within-tolerance index group, and the number of successive remaining indices is at least equal to the group size value, selecting the successive potential index group, wherein the lowest index of the successive potential index group is immediately succeeding the highest index of the preceding potential index group, if the preceding potential index group is counted as a within-tolerance index group, and the number of successive remaining indices is less than the group size value, concluding the determining the maximum number, if the preceding potential index group is not counted as a within-tolerance index group, and the number of successive remaining indices is at least equal to the group size value, selecting the successive potential index group, wherein the lowest index of the successive potential index group is immediately succeeding the lowest index of the preceding potential index group, if the preceding potential index group is not counted as a within-tolerance index group, and no remaining index is identified, concluding the determining the maximum number, until the number of successive remaining indices is less than the group size value.

8. The method according to claim 6, wherein:

assigning the respective index to each of the leaflet-flexibility values comprises arranging the indices in an ordered series in which the indices are ordered according to an order of magnitude of the respective leaflet-flexibility values; and designating at least some of the leaflets of the aggregate into designated leaflet groups comprises, starting at the beginning of the ordered series, iteratively:

(a) selecting a preliminary index group from among remaining indices, a remaining index being defined as an index that is positioned later, in the ordered series, than any index that has previously been selected as an index of a preliminary index group, wherein selecting of the preliminary index group is such that:

a lowest index of the preliminary index group is the index of the preliminary index group that has a lowest leaflet-flexibility value of the indices of the preliminary index group, and a highest index of the preliminary index group is the index of the preliminary index group that has a highest leaflet-flexibility value of the indices of the preliminary index group, the preliminary index group includes a number of successive indices equal to the group size, and the lowest index of the preliminary index group is the lowest remaining index;

(b) determining if the leaflet-flexibility value of each index of the preliminary index group is within the intra-group tolerance with respect to the leaflet-flexibility value of each other index of the preliminary index group;

(c) counting a number of remaining indices;

(d) responsively to the step of the determining, and to the step of the counting, selectively selecting an index group from a cluster of indices, the cluster of indices comprising the preliminary index group and a predetermined number of successive indices, wherein the lowest index of the preliminary index group is the lowest index of the cluster, and selectively selecting the index group from the cluster of indices comprises:

if the flexibility value of each index of the preliminary index group is determined to be within the intra-group tolerance with respect to the leaflet-flexibility value of each other index of the preliminary index group, iteratively:

(1) selecting, from the indices of the cluster, an index group that (i) has not previously been selected from the indices of the cluster, and (ii) has a group-differential that is no greater than the group-differential of any other index group that has not previously been selected from the cluster, a group-differential being a value that represents a difference between the leaflet-flexibility values of the indices of the index group, (2) determining whether designating the selected index group would reduce a total number of within-tolerance index groups that may be attained from the indices, compared to the maximum number;

(3) in response to the determining whether designating the selected index group would reduce the total number of within-tolerance index groups attainable from the indices, selectively designating the selected index group, wherein selectively designating the selected index group comprises:

if designating the selected index group is determined to not reduce the total number of within-tolerance index groups attainable from the indices, designating the selected index group, and if designating the selected index group is determined to reduce the total number of within-tolerance index groups attainable from the indices, not designating the selected index group, until the selected index group of a given iteration of step (d) is designated, and if the flexibility value of each index of the preliminary index group is determined to not be within the intra-group tolerance with respect to the leaflet-flexibility value of each other index of the preliminary index group, repeating steps a-d;

until the counted number of remaining indices is less than the group size value.

9. The method according to claim 8, wherein determining whether designating the selected index group would reduce the total number of within-tolerance index groups that may be attained from the indices, compared to the maximum number, comprises:

calculating a number of within-tolerance index groups that may be attained from the indices, should the selected index group be designated, by:

(a) selecting a first potential index group from among successive indices, such that:
the first potential index group includes a number of indices equal to the group size, and
the lowest index of the first potential index group is the lowest remaining index;

with regard to the first potential index group:

(b) calculating the group-differential, the group-differential being a difference between (i) the leaflet-flexibility value of the highest index, and (ii) the leaflet-flexibility value of the lowest index;

(c) determining whether the group-differential is greater than, or no greater than, the intra-group tolerance, and responsively:

(d) if the group-differential is no greater than the intra-group tolerance, counting the potential index group as a within-tolerance index group that may be attained from the indices, and (e) if the group-differential is greater than the intra-group tolerance, not counting the potential index group as a within-tolerance index group that may be attained from the indices;

(f) responsively to the counting the number of successive remaining indices, iteratively:
selectively selecting a successive potential index group including a remaining index, such that:
the successive potential index group includes a number of indices equal to the group size, and
the lowest index of the successive potential index group is the lowest remaining index,
wherein selectively selecting the successive potential index group comprises:
if a preceding potential index group is counted as a within-tolerance index group that may be attained from the indices should the best-matching index group be designated, and the number of successive remaining indices is at least equal to the group size value:
selecting the successive potential index group, wherein the lowest index of the successive potential index group is immediately succeeding the highest index of the preceding potential index group, and
repeating, with respect to the successive potential index group, steps b-e,
if the preceding potential index group is not counted as a within-tolerance index group that may be attained from the indices, should the best-matching index group be designated, and the number of successive remaining indices is at least equal to the group size value:
selecting the successive potential index group, wherein the lowest index of the successive potential index group is immediately succeeding the lowest index of the preceding potential index group, and
repeating, with respect to the successive potential index group, steps b-e,
until the number of successive remaining indices is less than the group size value;

comparing the number of within-tolerance index groups that may be attained from the indices, should the best-matching index group be designated, to the maximum number of within-tolerance groups; and responsively to the step of comparing:
if the number of within-tolerance index groups that may be attained from the indices, should the best-matching index group be designated, is no less than the maximum number of within-tolerance groups, determining that the selected index group would not reduce the total number of within-tolerance index groups attainable from the indices, and
if the number of within-tolerance index groups that may be attained from the indices, should the best-matching index group be designated, is less than the maximum number of within-tolerance groups, determining that the selected index group would reduce the total number of within-tolerance index groups attainable from the indices.

10. The method according to claim 8, wherein identifying the best-matching index group from the cluster of indices comprises:
calculating, for each index group including a number of indices equal to the group size value, attainable from the cluster of indices, a parameter,
identifying the one index group of the index groups having a lowest parameter value as the best-matching index group.

11. A system for use with a plurality of prosthetic heart valve leaflets, the system comprising:
a storage array, the storage array comprising:
a plurality of cells, each cell configured to contain exactly one of the leaflets; and
a plurality of indicators, each of the indicators associated with a corresponding one of the cells; and
circuitry, in communication with the plurality of indicators, and configured to:
receive a group size value,
using one or more leaflet-flexibility values that each corresponds to a respective one of the leaflets, designate at least some of the leaflets into leaflet groups, each of the leaflet groups including a number of leaflets equal to the group size value, and
for each of the leaflet groups, drive the indicators to indicate which of the cells contain leaflets designated the leaflet group.

12. The system according to claim 11, wherein the circuitry is configured to, for each respective one of the leaflets:
receive a digital image,
by digitally analyzing the digital image, calculate an image parameter for the leaflet, and
from the image parameter, derive the one or more leaflet-flexibility values that corresponds to the leaflet.

13. The system according to claim 11, further comprising an image sensor in communication with the circuitry, the image sensor configured to acquire, for each respective one of the leaflets, the digital image, and to communicate the digital image to the circuitry.

14. The system according to claim 11, wherein the plurality of indicators comprise a user-interface, the user-interface configured to facilitate switching from indicating which of the cells contain leaflets designated to a first leaflet group, to indicating which of the cells contain leaflets designated to a second leaflet group.

15. The system according to 11, wherein the plurality of indicators comprise a user-interface, the user-interface configured to facilitate switching from indicating the designation of at least some of the leaflets into a first leaflet group, to indicating the designation of at least some of the leaflets into a second leaflet group.

16. A method for grouping leaflets for use in prosthetic heart valves, the method comprising:
   positioning each leaflet of a first batch of leaflets opposite an image sensor;
   subsequently, initiating acquisition, by the image sensor, of a first digital image that includes all of the leaflets of the first batch;
   subsequently, removing each leaflet of the first batch to a storage array in a manner that facilitates tracking of an individual identity of each leaflet of the first batch;
   positioning each leaflet of a second batch of leaflets opposite the image sensor;
   subsequently, initiating acquisition, by the image sensor, of a second digital image that includes all of the leaflets of the second batch;
   subsequently, removing the leaflets of the second batch to the storage array in a manner that facilitates tracking of the individual identity of each leaflet of the second batch, thereby assembling the leaflets of the first batch and the leaflets of the second batch into an aggregate of leaflets;
   subsequently, operating software to:
      receive the first digital image and the second digital image,
      by digitally analyzing the first digital image and the second digital image, for each of the leaflets included in the first digital image and the second digital image:
         calculate an image parameter for the leaflet, and
         from the image parameter, derive a leaflet-flexibility value for the leaflet,
      receive a group size value,
      designate at least some of the leaflets of the aggregate of leaflets into one or more designated leaflet groups:
         based on similarity between the respective leaflet-flexibility values of each of the leaflets of the aggregate, and
         such that each of the leaflet groups includes a number of leaflets equal to the group size value, and
      output an indication of the one or more designated leaflet groups; and
   in response to the indication, grouping the at least some leaflets of the aggregate of leaflets into the one or more designated leaflet groups.

17. The method according to claim 16, further comprising, subsequently to grouping the at least some leaflets of the aggregate of leaflets into the one or more designated leaflet groups, sewing the leaflets of each designated leaflet group into a respective prosthetic heart valve.

18. The method according to claim 16, wherein:
   operating the software to designate the at least some of the leaflets of the aggregate of leaflets into one or more designated leaflet groups, based on similarity between the respective leaflet-flexibility values of each of the leaflets of the aggregate, comprises operating the software to designate the at least some of the leaflets of the aggregate of leaflets into one or more designated leaflet groups, based on an intra-group tolerance that represents a maximum allowable difference between leaflet-flexibility values of indices of a leaflet group; and
   operating the software further comprises operating the software to, prior to outputting the indication of the one or more designated leaflet groups, display a preview relating to the one or more designated leaflet groups, and
   the method further comprises, prior to grouping the at least some leaflets of the aggregate of leaflets into the one or more designated leaflet groups, adjusting the intra-group tolerance responsively to the preview relating to the one or more designated leaflet groups.

19. The method according to claim 16, wherein assembling the leaflets of the first batch and the leaflets of the second batch into the aggregate of leaflets comprises temporarily storing each leaflet of the aggregate in the storage array in a manner that facilitates maintenance of one or more attributes selected from the group consisting of: moisture content of the leaflets, and sterility of each leaflet.

20. The method according to claim 19, further comprising operating the software to indicate, on at least one indicator, a respective portion of the storage array in which each leaflet of the aggregate is to be temporarily stored; and
   temporarily storing each leaflet of the aggregate in the storage array comprises temporarily storing the leaflet in the respective portion of the storage array.

21. The method according to claim 20, wherein:
   the storage array includes a plurality of storage cells,
   operating the software to indicate, on at least one indicator, the respective portion of the storage array in which each leaflet of the aggregate is to be temporarily stored comprises operating the software to indicate a respective storage cell of the plurality of storage cells in which each leaflet of the aggregate is to be temporarily stored; and
   temporarily storing each leaflet of the aggregate in the respective portion of the storage array comprises temporarily storing each leaflet of the aggregate in the respective storage cell.

\* \* \* \* \*